US012338485B2

(12) United States Patent
Stengel et al.

(10) Patent No.: US 12,338,485 B2
(45) Date of Patent: *Jun. 24, 2025

(54) MULTIPLEXED PROFILING OF RNA AND DNA MODIFICATIONS

(71) Applicant: Alida Biosciences Inc., San Diego, CA (US)

(72) Inventors: Gudrun Stengel, San Diego, CA (US); Byron Purse, San Diego, CA (US); Yu-Hsien Hwang-Fu, San Diego, CA (US); Jerome Santos, San Diego, CA (US)

(73) Assignee: Alida Biosciences Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/479,622

(22) Filed: Oct. 2, 2023

(65) Prior Publication Data

US 2024/0110222 A1 Apr. 4, 2024

Related U.S. Application Data

(63) Continuation of application No. 17/706,493, filed on Mar. 28, 2022, now Pat. No. 11,773,425, which is a continuation of application No. PCT/US2021/060829, filed on Nov. 24, 2021.

(60) Provisional application No. 63/193,402, filed on May 26, 2021, provisional application No. 63/118,409, filed on Nov. 25, 2020.

(51) Int. Cl.
*C12Q 1/6804* (2018.01)

(52) U.S. Cl.
CPC .................................. *C12Q 1/6804* (2013.01)

(58) Field of Classification Search
CPC .................................. C12Q 1/68; C12Q 1/6804
See application file for complete search history.

(56) References Cited

U.S. PATENT DOCUMENTS

| | | | |
|---|---|---|---|
| 5,648,213 A | 7/1997 | Reddy et al. | |
| 5,683,874 A * | 11/1997 | Kool | C12N 15/1135 536/23.1 |
| 5,731,171 A * | 3/1998 | Bohlander | C12Q 1/686 435/6.14 |
| 11,773,425 B2 * | 10/2023 | Stengel | C12Q 1/6804 435/6.1 |
| 2001/0000078 A1 | 3/2001 | Moskal et al. | |
| 2003/0039967 A1 | 2/2003 | Kris et al. | |
| 2003/0186344 A1 * | 10/2003 | Holmes | G01N 33/5308 435/7.92 |
| 2003/0235852 A1 | 12/2003 | Roberts et al. | |
| 2005/0136414 A1 | 6/2005 | Gunderson et al. | |
| 2006/0008807 A1 * | 1/2006 | O'Hara | C12N 15/1003 435/6.14 |
| 2006/0204988 A1 * | 9/2006 | Fassbender | C12Q 1/6827 435/6.12 |
| 2006/0276426 A1 * | 12/2006 | Auwerx | G01N 33/74 435/254.2 |
| 2008/0076156 A1 * | 3/2008 | Inouye | C07K 14/31 435/69.7 |
| 2008/0241818 A1 * | 10/2008 | Lappalainen | C12Q 1/705 435/5 |
| 2009/0018029 A1 | 1/2009 | Miao et al. | |
| 2009/0181373 A1 * | 7/2009 | Li | C12Q 1/6853 435/6.12 |
| 2010/0081134 A1 * | 4/2010 | Mirkin | C12Q 1/6816 435/7.1 |
| 2013/0115272 A1 * | 5/2013 | de Fougerolles | A61K 48/0066 424/490 |
| 2014/0004569 A1 * | 1/2014 | Lambowitz | C12P 19/34 435/91.21 |
| 2015/0299784 A1 * | 10/2015 | Fan | C12N 15/1075 506/4 |

(Continued)

FOREIGN PATENT DOCUMENTS

WO 2018204854 A1 11/2018

OTHER PUBLICATIONS

Kando et al.Journal of Nucleic Acids Article ID 543531 (7 pgs. ) (Year: 2010).*
Reddington et al., Secrets of a covalent interaction for biomaterials and biotechnology: SpyTag and SpyCatcher. Current Opinions in Chemical Biology (Year: 2012).*
Mora et al., Next generation ligand binding assays—review of emerging technologies' capabilities to enhance throughput and multiplexing. The AAPS Journal 16(6) :1175 (Year: 2014).*
Xu et al. Structural basis for selective binding of m6A RNA by the YTHDC1 YTH domain. Nature Chemical Biology 10:927 (Year: 2014).*
Luo et al., DNA N6-methyladenine: a new epigenetic mark in eukaryotes? Nature Review | Molecular Cell Biology 16 : 705 (Year: 2015).*

(Continued)

*Primary Examiner* — Ethan C Whisenant
(74) *Attorney, Agent, or Firm* — Rothwell, Figg, Ernst and Manbeck, P.C.

(57) ABSTRACT

Provided herein are compositions and methods for the multiplexed profiling of RNA and DNA modifications across transcriptomes and genomes, respectively. The methods combine molecular recognition of non-canonical features (e.g., base modifications, backbone modifications, lesions, and/or structural elements) of a target nucleic acid with a step of writing the information from this recognition event into the neighboring genetic sequence of the target nucleic acid using a barcode. The resultant barcoded nucleic acids are then converted into sequencing libraries and read by DNA/RNA sequencing methods. This step reveals the sequence of the barcode, which is correlated with the non-canonical feature in the target nucleic acid(s). The high throughput profiling methods described herein allow for localization of one or more modifications in a target nucleic acid. The methods also allow for identification of the nature and location of several or all DNA/RNA modifications in parallel.

15 Claims, 44 Drawing Sheets

Specification includes a Sequence Listing.

(56) References Cited

U.S. PATENT DOCUMENTS

| | | | |
|---|---|---|---|
| 2015/0376608 A1* | 12/2015 | Kaper | C12N 15/1093 |
| | | | 506/26 |
| 2016/0024160 A1* | 1/2016 | Tota | C07K 14/43595 |
| | | | 536/23.5 |
| 2017/0067905 A1 | 3/2017 | Wang | |
| 2018/0044724 A1* | 2/2018 | Fan | C12Q 1/6855 |
| 2018/0360950 A1 | 12/2018 | Chene et al. | |
| 2019/0376929 A1 | 12/2019 | Adelman et al. | |
| 2020/0102604 A1 | 4/2020 | Tosato et al. | |
| 2020/0131567 A1* | 4/2020 | Kennedy | C12N 15/10 |
| 2020/0377875 A1* | 12/2020 | Ares | C12Y 207/07052 |
| 2020/0399679 A1* | 12/2020 | Ellington | C12N 11/12 |
| 2021/0024977 A1* | 1/2021 | Song | C12N 9/22 |
| 2021/0054018 A1* | 2/2021 | Murray | C12P 19/30 |
| 2021/0164021 A1* | 6/2021 | Hogers | C12Q 1/6806 |
| 2021/0164992 A1* | 6/2021 | Mohr | G01N 33/6866 |
| 2021/0340596 A1* | 11/2021 | Meltzer | G01N 33/54313 |
| 2021/0355483 A1* | 11/2021 | Chee | G01N 33/68 |
| 2022/0064631 A1* | 3/2022 | Barna | C12N 15/1093 |
| 2022/0111019 A1 | 4/2022 | Kelly et al. | |
| 2023/0133188 A1* | 5/2023 | Frischmuth | A61K 39/12 |
| | | | 424/185.1 |
| 2023/0265484 A1* | 8/2023 | Kirschner | C40B 20/04 |
| | | | 435/6.1 |
| 2023/0295723 A1* | 9/2023 | Fan | C12Q 1/6806 |
| 2023/0332213 A1 | 10/2023 | Henikoff | |
| 2023/0348910 A1* | 11/2023 | Yang | C12N 15/11 |

OTHER PUBLICATIONS

Feederle et al., Antibodies specific for nucleic acid modifications. RNA Biology14(9):1089-1098 (Year: 2017).*

Loomis et al., In Vitro Transcribed mRNA Vaccines with Programmable Stimulation of Innate Immunity. Bioconjugate Chemistry 29:3072 (Year: 2018).*

Arul et al., Sample multiplexing strategies in quantitative proteomics. Analytical Chemistry 91:178-189 (Year: 2019).*

Chiu et al.Antibody structure and function: the basis for engineering therapeutics Antibodies 8, 55 antib8040055 (Year: 2019).*

Matsuzawa et al., Development and validation of monoclonal antibodies against N6-methyladenosine for the detection of RNA modifications. PLOS one (Oct. 2019) 0223197, 15 pgs (Year: 2019).*

Meyer, KD., Meyer DART-seq. Nature Methods 16:1275-1280 (Year: 2019).*

Shendure et al., DNA sequencing at 40 : past, present and future. Nature 550:345-353 (Year: 2019).*

Shao et al., NAD tagSeq for transcriptome-wide identification and characterization of NAD+-capped RNAs. Nature Protocols 15 :2813-2836 (Year: 2020).*

Office Action issued in U.S. Appl. No. 17/706,470 dated Dec. 15, 2022, 13 pgs.

Meyer et al., "Comprehensive Analysis of mRNA Methylation Reveals Enrichment in 3' UTRs and near Stop Codons", Cell, 149 (7), 2012, 1635-1646.

Kumar, et al. "Quantitative Multiplexed ChIP Reveals Global Alterations that Shape Promoter Bivalency in Ground State Embryonic Stem Cells", (2019), Cell Reports 28, 3274-3284.

Ilyer et al., bioRxiv preprint posted online on Mar. 20, 2018 (Year: 2018).

Jin et al., Nucleic Acids Research 44(13) : e116 (Year: 2016).

Kingsmore, SF. Nature Reviews Drug Discovery 5: 310-321 (Year: 2006).

Kubo et al. Biochemistry 31: 3703-3708 (Year: 1992).

Saini et al., Biochimie 95: 117-123 (Year: 2013).

Suseela et al., Chem. Soc. Rev. 47:1098-1131 (Year: 2018).

Albanese et al., Chemical Biology 15: 103-111 (Year: 2019).

Nam et al., Science 301: 1884-1886 (Year: 2003).

Safarik et al., Biomagnetic Research and Technology 2:7 pp. 1-17 (Year: 2004).

Office Action dated Feb. 14, 2025 issued in U.S. Appl. No. 18/792,527. (18 pages).

Ahern, H.; "Biochemical, Reagents Kits Offer Scientists Good Return on Investment"; The Scientist 9(15):20; Jul. 24, 1995; 7 pages.

Li et al.; "Flexible Binding of m6A Reader Protein YTHDC1 to Its Preferred RNA Motif"; J. Chem.Comput.; 15; 2019; 11 pages.

Noren et al.; "A General Method for Site-Specific Incorporation of Unnatural Amino Acids into Proteins"; Science; 1989; 7 pages.

Skerra, A.; "Engineered protein scaffolds for molecular recognition"; J. of Molecular Recognition; 2000; 21 pages.

Song et al.; "An all-to-all approach to the identification of sequence-specific readers for epigenetic DNA modifications on cytosine"; Nature Communications; 2021; 16 pages.

Stahl et al.; "Affibody Molecules in Biotechnological and Medical Applications"; Trends in Biotechnology; 2017; 22 pages.

Zhao et al.; "Mapping the epigenetic modifications of DNA and RNA"; Protein Cell; 2020; 17 pages.

Notice of Allowance dated Nov. 21, 2024 issued in U.S. Appl. No. 18/343,028. (8 pages).

Kaya-Okur et al., "CUT&Tag for efficient epigenomic profiling of small samples and single cells", Nature Communications, 12:795 (Year: 2019). (10 pages).

* cited by examiner

Double-stranded nucleic acid with modification

Single-stranded nucleic acid with modification

Single-stranded nucleic acid with structural element

Binding domain conjugated to an adapter (Nucleic Acid-Binding Molecule)

Barcoding complexes with different types of targets:

FIG. 2A Type A: Universal cap

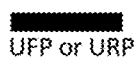

UFP or URP

Legend
- Universal Forward Primer (UFP)
- Universal Reverse Primer (URP)
- Modification encoding barcode (MBC)
- Unique Molecular Identifier (UMI)
- Cleavage Site (CLS)
- Spacer (SP)

FIG. 2B Type B: Adapter for library preparation by circularization

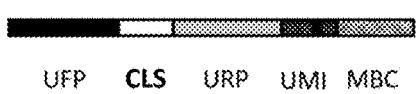

UFP  CLS  URP  UMI  MBC

FIG. 2C Type C: Adapter for barcode transfer by ligation reactions

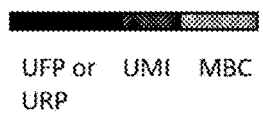

UFP or   UMI   MBC
URP

FIG. 2E Type E: Adapter for internal priming and long read construction

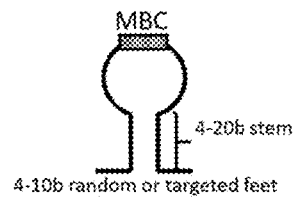

MBC
4-20b stem
4-10b random or targeted feet

FIG. 2D Type D: Adapter for barcode transfer by primer extension

For a single barcoding event

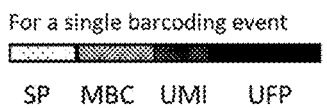

SP   MBC   UMI   UFP

For multiple barcoding events

SP1   MBC   UMI   SP2

FIG. 2F Type F: Adapter for internal priming and short read construction

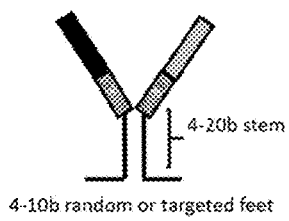

4-20b stem
4-10b random or targeted feet

FIG. 2G Type G: Adapter for barcode transfer by primer extension with DNA address

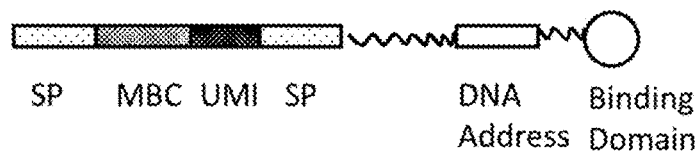

SP   MBC  UMI   SP         DNA         Binding
                           Address     Domain (A) Surface-immobilized recognition elements (B) RNA capture via poly-A tail (C) DNA or RNA capture via hybridization probes (D) Covalently tethered nucleic acid target

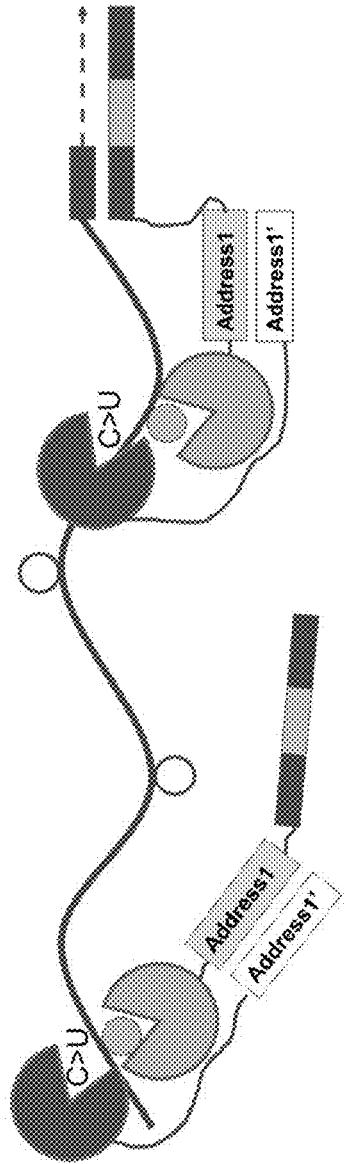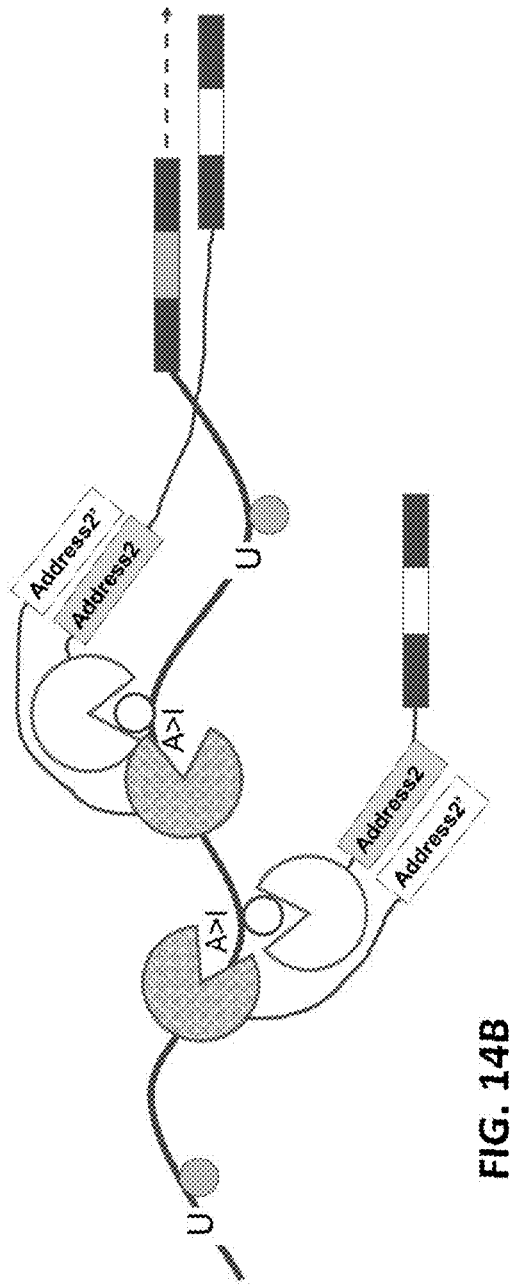
FIG. 14B

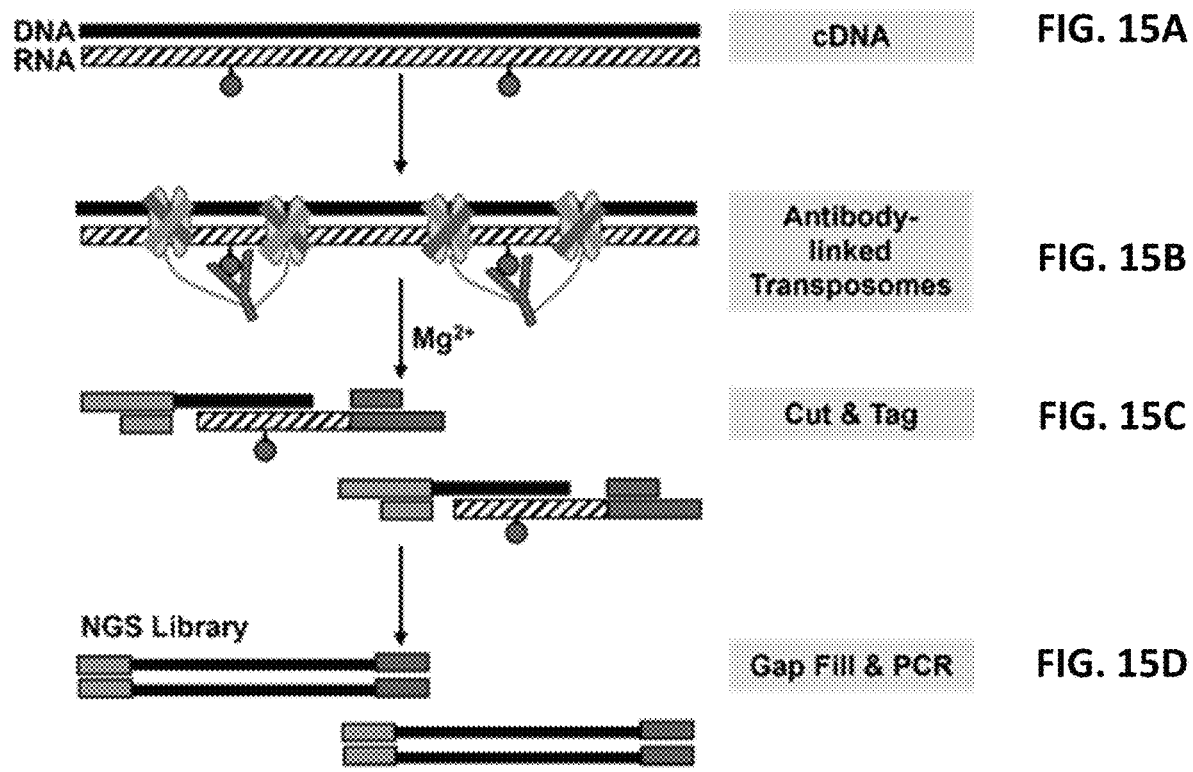
FIG. 15A
FIG. 15B
FIG. 15C
FIG. 15D

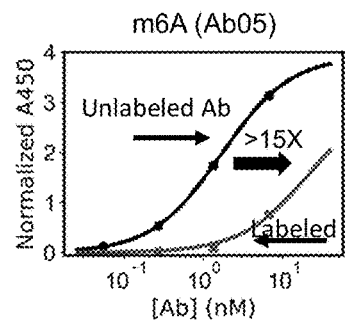 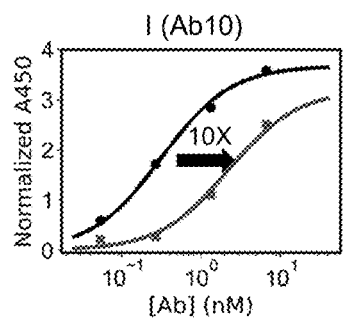 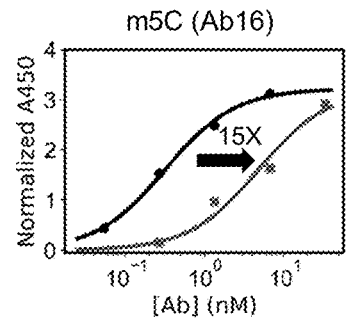
FIG. 21A  FIG. 21B  FIG. 21C
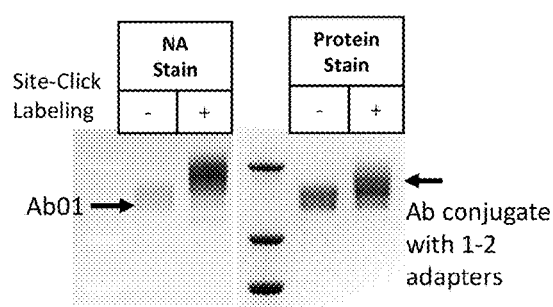 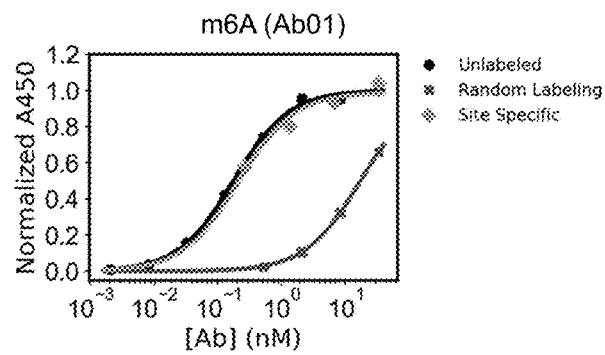
FIG. 21D  FIG. 21E

Activation of target nucleic acids for barcoding by primer extension
(A) Tailing with one type of NTP (e. g. ATP)
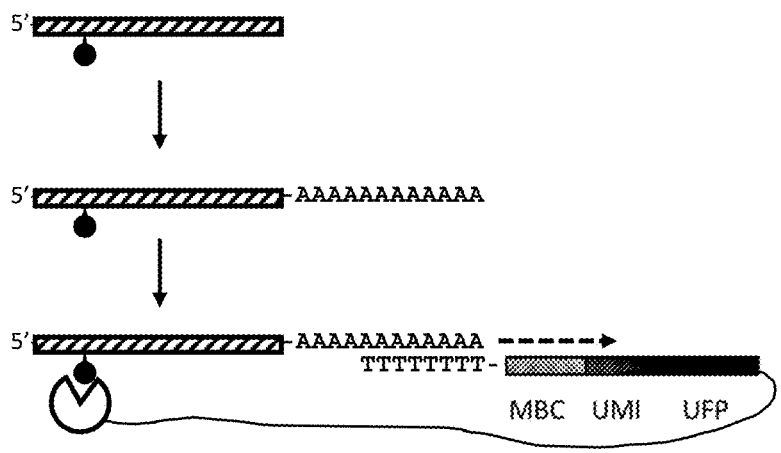
(B) Ligation of a spacer sequence (e. g. GATGATGT)
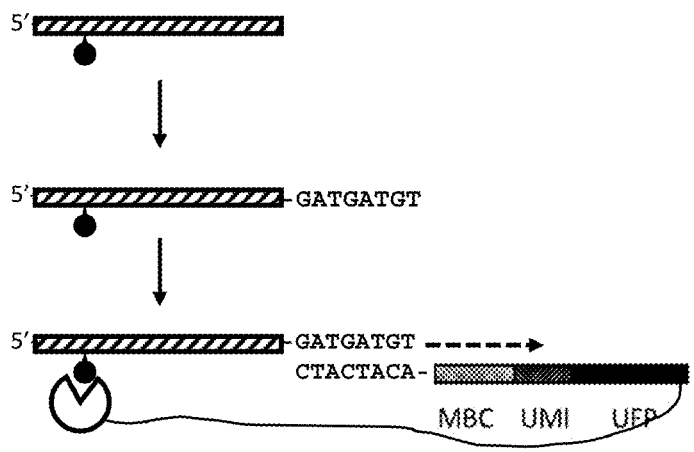
FIG 23A

Size-controlled 3' A-tailing of RNA

Target pull-down on protein G beads and barcode transfer by ligation

Preparation of passivated beads with tunable capture probe density
Capture probe density is determined by grafting ratio
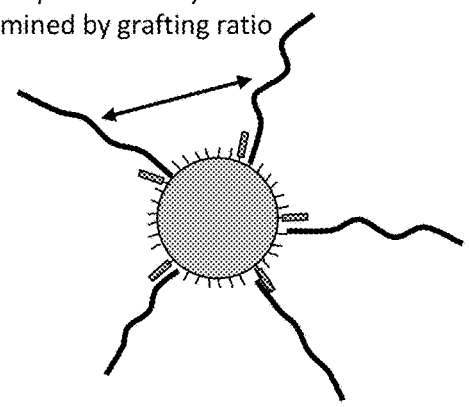
Passivation molecule: COOH-PEG4-Amine
Grafting moiety attached to bead: Methyltetrazine(mTet)-PEG4-amine
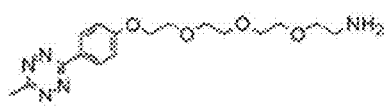
Grafting moiety attached to hybridization probe: TCO-PEG4-NHS ester
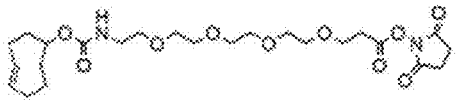
Hybridization probe: CATCTGACGCTGCCGACGATTTTTT/3AmMO/
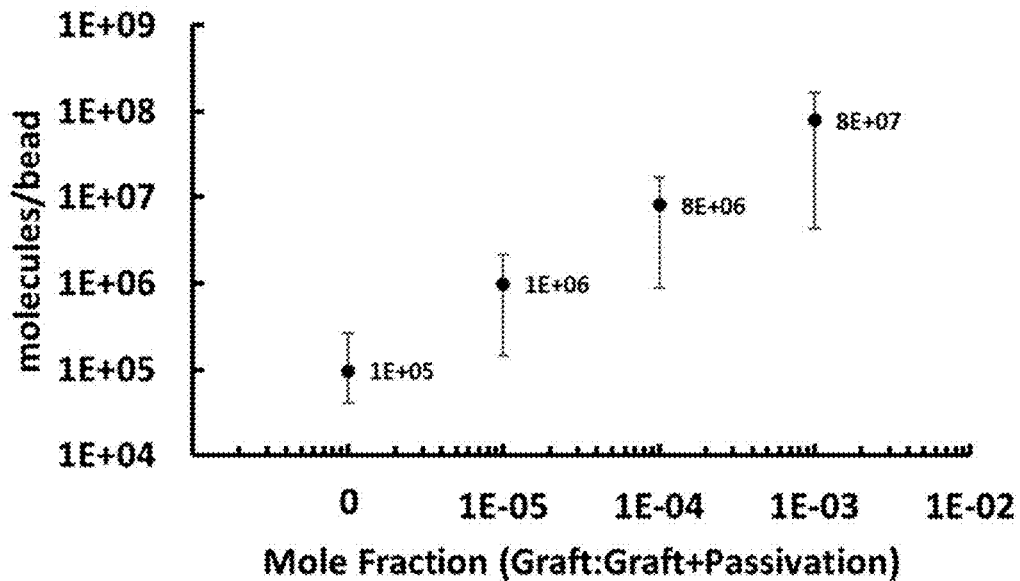
FIG. 25

Preparation of a streptavidin-derived nucleic acid binding molecule
Strepatvidin:
adapter ratio    1:1      1:2      1:3      1:4
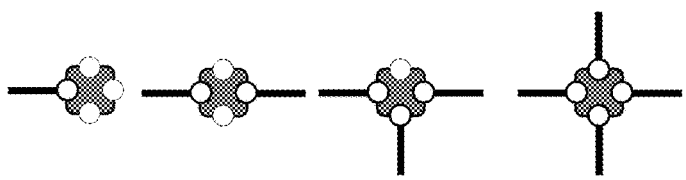
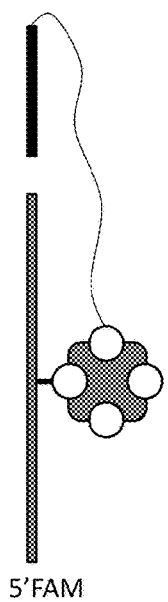
Barcoding of biotinylated RNA by a streptavidin-adapter conjugate
FIG 26A

Biotin-specific barcoding in solution

Biotin-specific barcoding on 1:1000 mTet:carboxy PEG beads

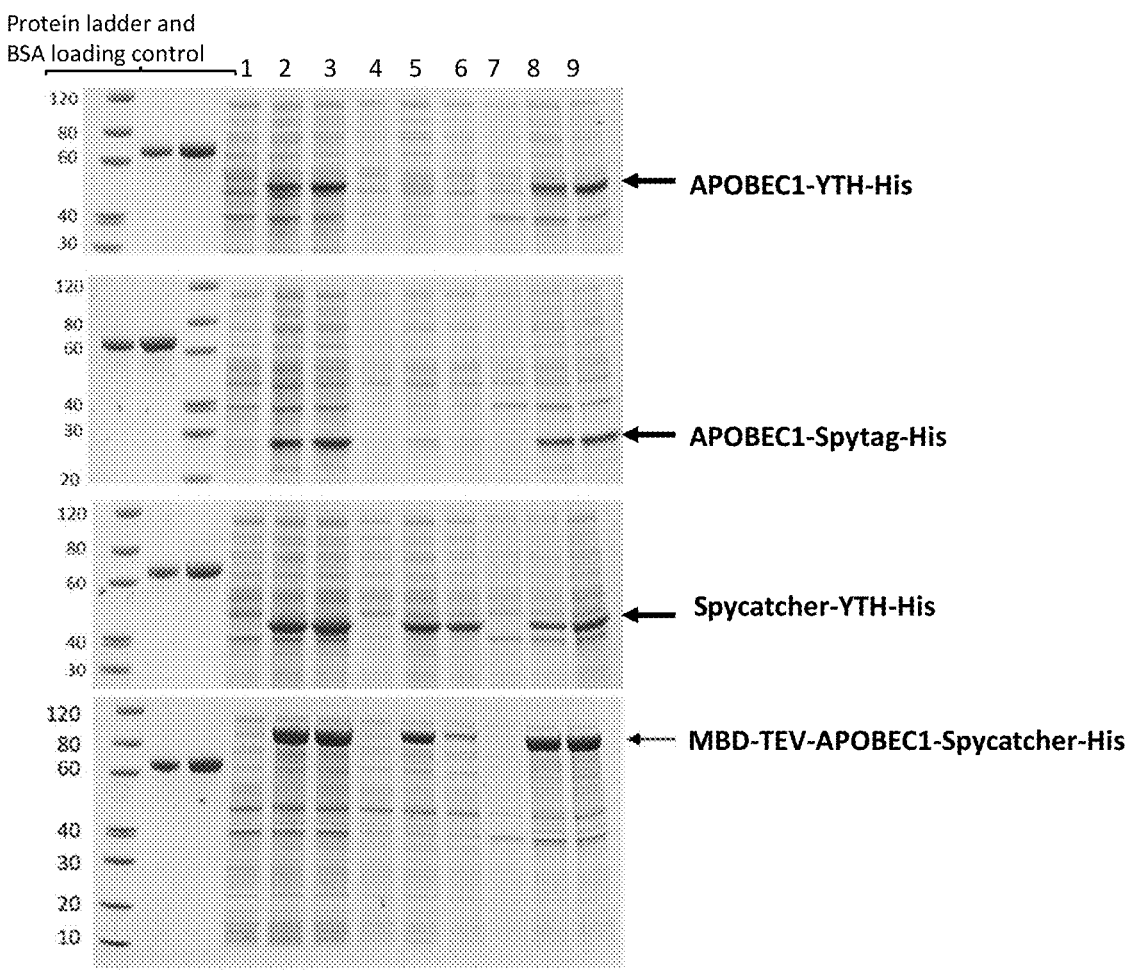

1) Cell lysate without induction
2) Cell lysate with induction for 16 h at 15 °C
3) Cell lysate with induction for 4 h at 37 °C
4) Supernatant of cell lysate non-induced
5) Supernatant of cell lysate with induction for 16 h at 15 °C
6) Supernatant of cell lysate with induction for 4 h at 37 °C
7) Pellet of cell lysate non-induced
8) Pellet of cell lysate with induction for 16 h at 15 °C
9) Pellet of cell lysate with induction for 4 h at 37 °C

FIG 28

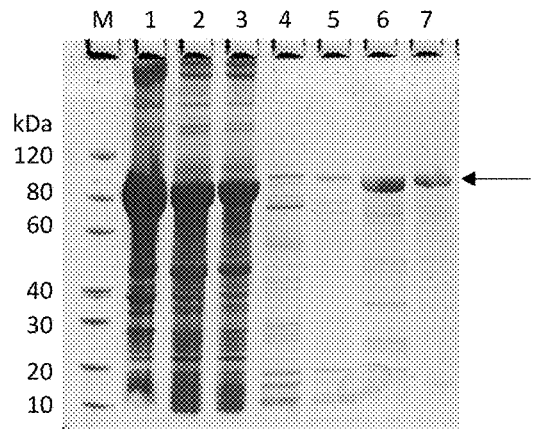

Purification of MBD-TEV-APOBEC1-Spycatcher-His by Ni-column
Lane M: Protein marker
Lane 1: Pellet of cell lysate after centrifugation
Lane 2: Supernatant of cell lysate after centrifugation (Loading)
Lane 3: Flow through
Lane 4: Elute with 50 mM Tris, 500 mM NaCl, 1mM TCEP, 20 mM imidazole, pH 8.0
Lane 5: Elute with 50 mM Tris, 500 mM NaCl, 1mM TCEP, 50 mM imidazole, pH 8.0
Lane 6: Elute with 50 mM Tris, 500 mM NaCl, 1mM TCEP, 500 mM imidazole, pH 8.0
Lane 7: Ni column after elution

FIG. 29A

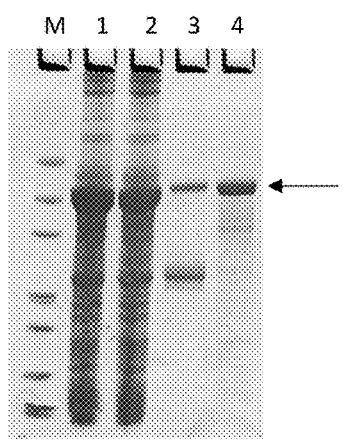

Purification of MBD-TEV-APOBEC1-Spycatcher-His by MBD-column
Lane M: Protein marker
Lane 1: Loading (Fractions of Lane 3 from Ni Column )
Lane 2: Flow through
Lane 3: Elute with 50 mM Tris-HCl, 500 mM NaCl, 1 mM TCEP, 20 mM Maltose monohydrate, pH 8.0
Lane 4: MBP column after elution

FIG. 29B

Amino acid sequence and domain organization of *in vitro* translated APOBEC enzymes rAPOBEC1-XTEN-Spycatcher

MSSETGPVAVDPTLRRRIEPHEFEVFFDPRELRKETCLLYEINWGGRHSIWRHTSQNTNK
HVEVNFIEKFTTERYFCPNTRCSITWFLSWSPCGECSRAITEFLSRYPHVTLFIYIARLY
HHADPRNRQGLRDLISSGVTIQIMTEQESGYCWRNFVNYSPSNEAHWPRYPHLWVRLYVL
ELYCIILGLPPCLNILRRKQPQLTFFTIALQSCHYQRLPPHILWATGLK*SGSETPGTSES*
*ATPES*<u>MVTTLSGLSGEQGPSGDMTTEEDSATHIKFSKRDEDGRELAGATMELRDSSGKTI</u>
<u>STWISDGHVKDFYLYPGKYTFVETAAPDGYEVATPIEFTVNEDGQVTVDGEATEGDAHT</u> hAPOBEC3A(E109Q)-XTEN-Spycatcher

MEASPASGPRHLMDPHIFTSNFNNGIGRHKTYLCYEVERLDNGTSVKMDQHRGFLHNQAK
NLLCGFYGRHAELRFLDLVPSLQLDPAQIYRVTWFISWSPCFSWGCAGQVRAFLQENTHV
RLRIFAARIYDYDPLYKEALQMLRDAGAQVSIMTYDEFKHCWDTFVDHQGCPFQPWDGLD
EHSQALSGRLRAILQNQGN*SGSETPGTSESATPES*<u>MVTTLSGLSGEQGPSGDMTTEEDSA</u>
<u>THIKFSKRDEDGRELAGATMELRDSSGKTISTWISDGHVKDFYLYPGKYTFVETAAPDGY</u>
<u>EVATPIEFTVNEDGQVTVDGEATEGDAHT</u>

Bold = r(rat) APOBEC1 or h(human) APOBEC3A(E109Q)
Cursive = XTEN linker
Underlined = Spycatcher

FIG. 30

Solution activity of *in vitro* translated APOBEC enzymes
3'FAM labeled DNA oligo containing single editing site
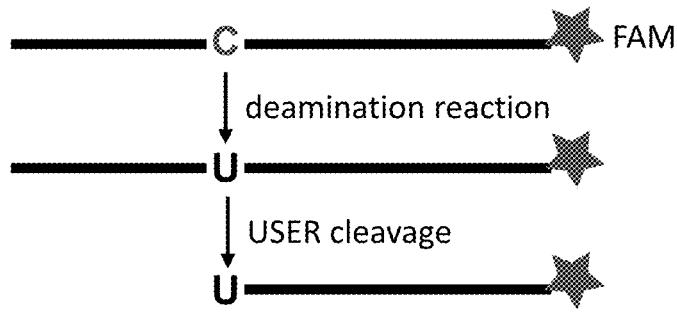
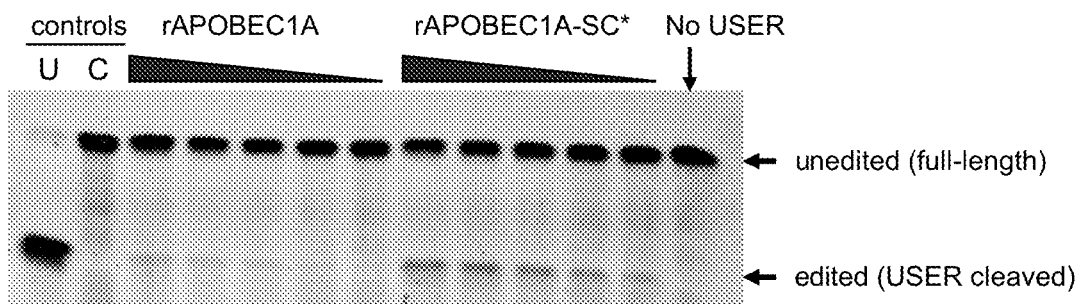
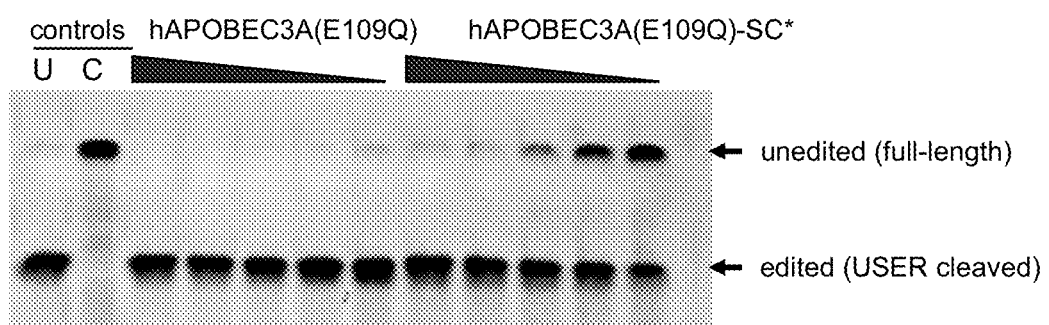
*SC = Spycatcher
FIG. 31

PPA assay activity of commercial APOBEC3A

Short single-editing site targets

| Type | Editing Site | Sequences (*primer hyb region in bold*) |
|---|---|---|
| RNA | U | rArGrArArCrArGrArArCrArGrArArUrAr*GrArUrGrAr UrArGrGrArArGrGrArUrGrArArGrGrUrGrArGrU* |
| RNA | C | rArGrArArCrArGrArArCrArGrArArCrAr*GrArUrGrAr UrArGrGrArArGrGrArUrGrArArGrGrUrGrArGrU* |
| DNA | U | AGAACAGAACAGAAUA*GATGATAGGAAGGATGAAGGTGAGT* |
| DNA | C | AGAAGAGAAGAGAACA*GATGATAGGAAGGATGAAGGTGAGT* |

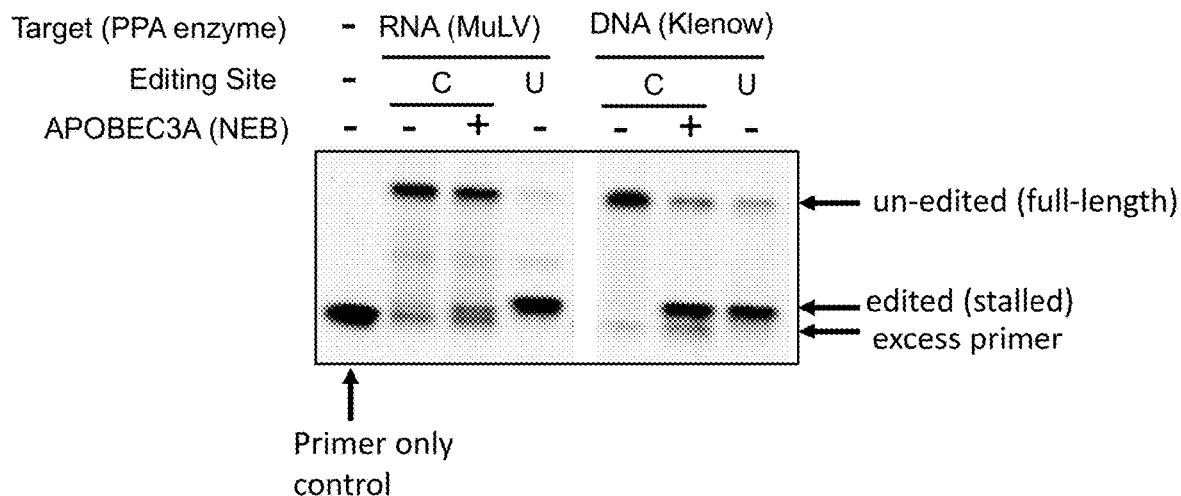

FIG. 33

Poisoned primer assay (PPA) for probing targeted deamination

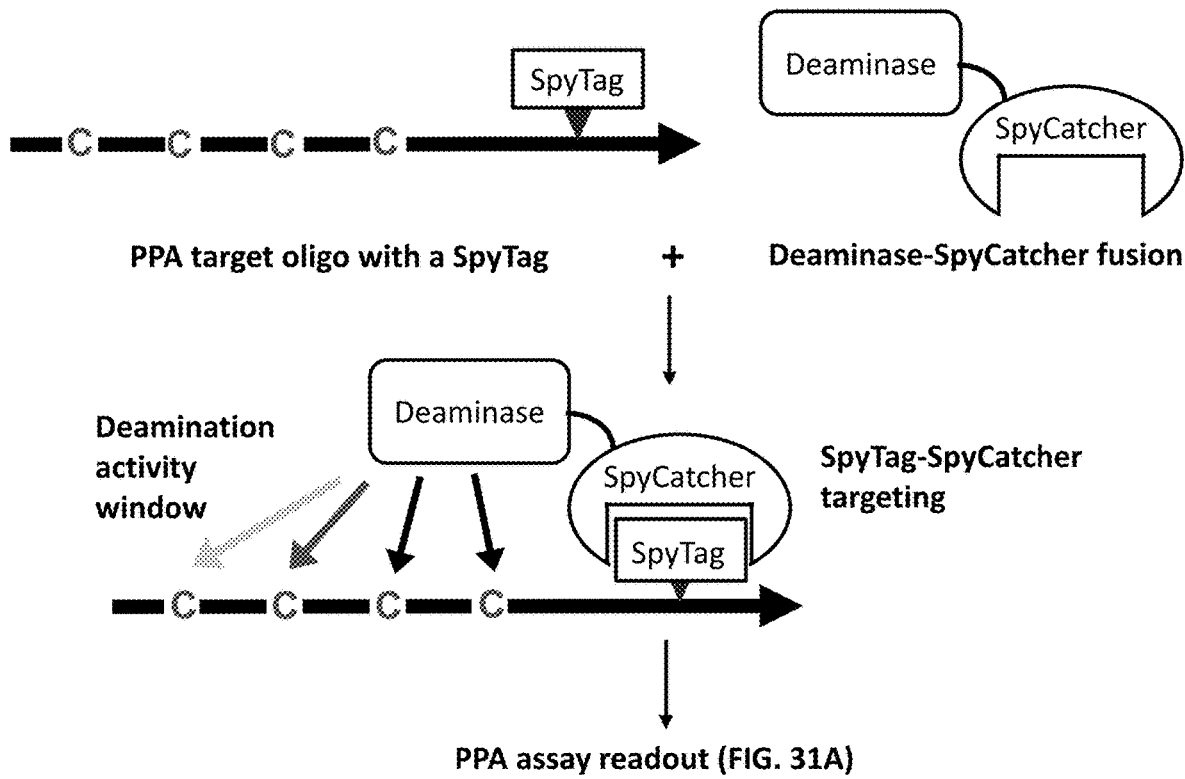

Editing window probe region | PPA priming region

GAACAGAACAGAACAGAACAGAACAGAACAGAACAGATGATAGGAAGGATGAAGGTGAGT
                                            CTACTATCCTTCCTACTTCCACTCA-FAM

Distal site probe                                          SpyTag

GAACAGAACAGAACAGAACAGAACAGAACAGAACAGATGATAGGAAGGATGAAGGTGAGT
SEQ ID NO: 48

Proximal site probe                    SpyTag

GAACAGAACAGAACAGAACAGAACAGAACAGAACAGATGATAGGAAGGATGAAGGTGAGT
SEQ ID NO: 49

FIG. 34

Demonstration of targeted base editing by *in vitro* translated APOBEC-Spycatcher fusion proteins
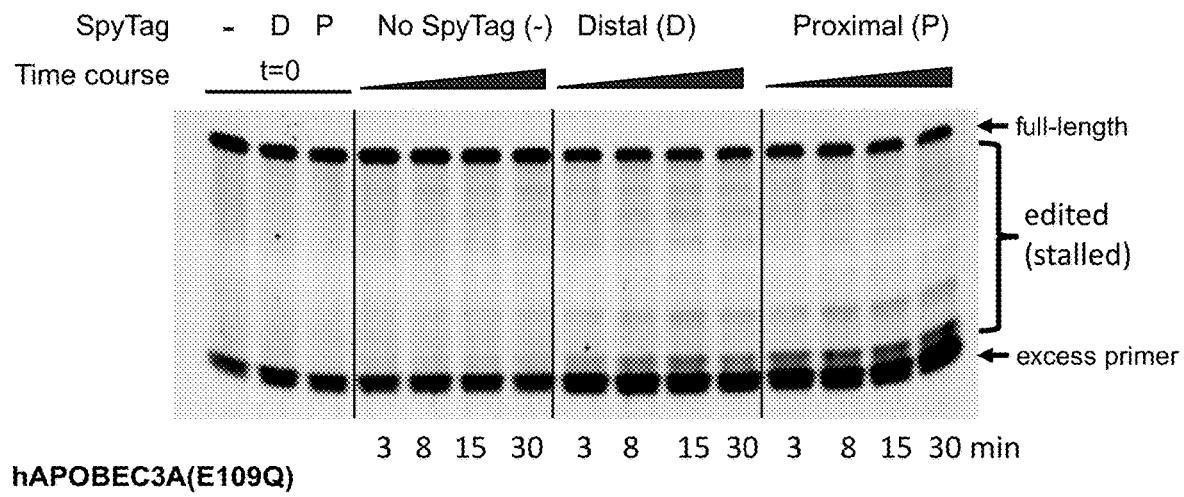
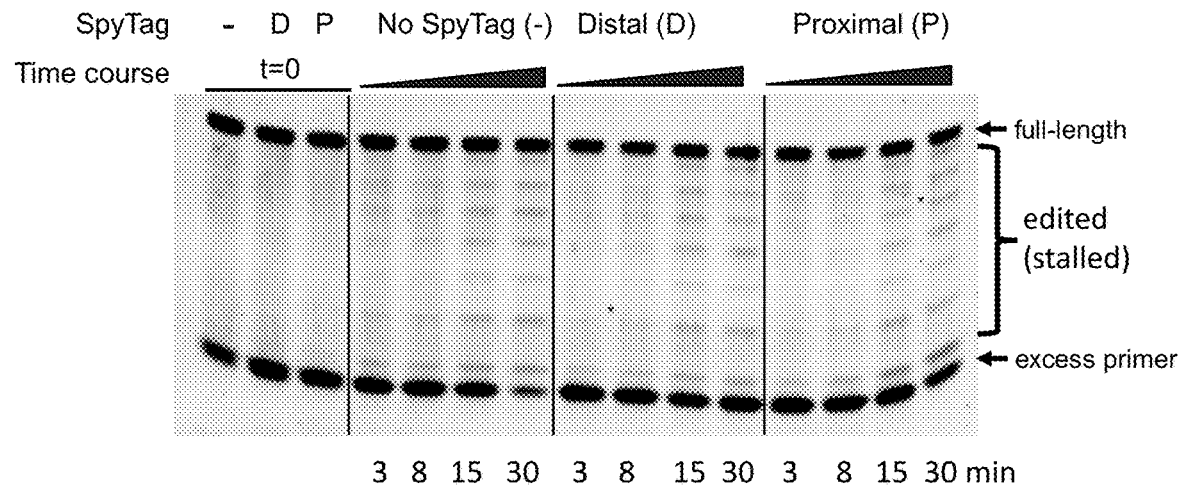
FIG. 35

MULTIPLEXED PROFILING OF RNA AND DNA MODIFICATIONS

CROSS REFERENCE TO RELATED APPLICATIONS

This application is a continuation of U.S. Ser. No. 17/706,493 filed Mar. 28, 2022, which is a continuation of PCT International Patent Application Serial No. PCT/US2021/060829, filed on Nov. 24, 2021, which claims priority to, and the benefit of, U.S. Provisional Application No. 63/193,402, filed on May 26, 2021, and U.S. Provisional Application No. 63/118,409, filed on Nov. 25, 2020, each of which is incorporated by reference herein in its entirety for all purposes.

FEDERAL FUNDING SUPPORT CLAUSE

This invention was made with US government support from grant number 1R43HG012170-01 awarded by the National Human Genome Research Institute. The US government has certain rights in the invention.

FIELD

The instant disclosure relates generally to the identification and analysis of epitranscriptomic, epigenetic and other modifications to the structures or noncanonical features of nucleic acids, including RNA and DNA.

SEQUENCE LISTING

The instant application contains a Sequence Listing which has been submitted electronically in XML format and is hereby incorporated by reference in its entirety. Said XML copy, created on Dec. 12, 2023, is named "5371-101US5.xml" and is 77,824 bytes in size.

BACKGROUND

Epigenetic changes, including chemical alterations of nucleotides, are widespread and play a major role in biological processes such as gene expression, gene silencing, and response to DNA damage. Likewise, chemical modifications of RNA, known as epitranscriptomic modifications, frequently occur within cells during or after transcription.

A wide variety of illnesses, behaviors, and other health indicators have been correlated with epigenetic changes in DNA, including cancers of almost all types, cognitive dysfunction, and respiratory, cardiovascular, reproductive, autoimmune, and neurobehavioral illnesses. However, little is known about the distribution of epigenetic changes throughout the genome, particularly in relation to health and disease. Some functions for epitranscriptomic modifications are known, but many are not, owing substantially to a lack of analytical methods for locating and quantifying these modifications in the entirety of cellular RNA. Currently, almost nothing is known about correlative levels of epitranscriptomic RNA modifications and their changes in cells because of a lack of robust, accessible methods for profiling a substantial number of these modifications simultaneously.

Combinations of chemical derivatization methods, molecular recognition (typically using antibodies, both for enrichment and detection), and sequencing by reverse transcription have provided profiling methods for a limited number of DNA and RNA modifications. However, these methods lack high sensitivity, cause some nucleic acid degradation/fragmentation, and often cannot be used to identify the location of the modifications at a single-base resolution. Moreover, these methods are not amenable to multiplexing. Existing methods for sequencing common epitranscriptomic RNA modifications often give conflicting findings both in terms of the number of detected modifications (different by more than an order of magnitude) and the location of the modifications.

Accordingly, there is a need in the art for improved compositions and methods for identifying, analyzing, quantifying, and locating DNA and RNA modifications. Such advancements would pave the way for discovery of key regulatory mechanisms of biology in health and disease, and the development of new treatment paradigms in medicine.

BRIEF SUMMARY

Provided herein are compositions and methods for the identification and analysis of epitranscriptomic, epigenetic and other chemical modifications to the structures of nucleic acids, including RNA and DNA. The instant disclosure provides highly parallelized, sensitive, accurate, and high-throughput methods for profiling a potentially unlimited number of DNA and/or RNA modifications simultaneously at the single molecule level.

In some embodiments, the disclosure provides a nucleic acid-binding molecule comprising a binding domain and an adapter, wherein the binding domain binds specifically to a non-canonical feature of a DNA or an RNA, and wherein the adapter comprises a nucleic acid barcode sequence unique to the non-canonical feature bound specifically by the binding domain.

In some embodiments, the disclosure provides a method for making a nucleic acid-binding molecule, the method comprising coupling an adapter to a binding domain, to form an adapter-binding domain conjugate.

In some embodiments, the disclosure provides a method for analyzing a plurality of target nucleic acids, the method comprising: contacting the target nucleic acids with a nucleic acid-binding molecule as described herein; either (i) transferring a nucleic acid barcode to the target nucleic acids to generate barcoded target nucleic acids, in an environment that substantially prevents off-target generation of barcoded nucleic acids, or (ii) generating barcoded copies of the target nucleic acids; modifying the barcoded target nucleic acids or the barcoded copies thereof, such that the position of the non-canonical feature is identifiable based on the primary nucleic acid sequence of the barcoded target nucleic acids, or the barcoded copies thereof; and sequencing the barcoded target nucleic acids.

In some embodiments, the disclosure provides a method for detecting and/or quantifying two or more non-canonical features in plurality of target nucleic acids, the method comprising: contacting the target nucleic acids with at least two nucleic acid-binding molecules, wherein each nucleic acid-binding molecule comprises a binding domain and an adapter, wherein the binding domain of each nucleic acid-binding molecule binds to a different non-canonical feature of a DNA or an RNA, wherein the adapter comprises a nucleic acid barcode sequence unique to the non-canonical feature bound specifically by each binding domain; either (i) transferring the nucleic acid barcode to the target nucleic acids to generate barcoded target nucleic acids, in an environment that substantially prevents off-target generation of barcoded nucleic acids, or (ii) generating barcoded copies of the target nucleic acids; modifying the barcoded target nucleic acids or the barcoded copies thereof, such that the position of the non-canonical feature is identifiable based on the primary nucleic acid sequence of the barcoded target nucleic acids, or the barcoded copies thereof; and sequencing the barcoded target nucleic acids.

In some embodiments, the disclosure provides a method for detecting a non-canonical feature in a target nucleic acid, the method comprising: contacting the target nucleic acid with a nucleic acid-binding molecule as described herein; either (i) transferring the nucleic acid barcode to the target nucleic acid to generated a barcoded target nucleic acid, in an environment that substantially prevents off-target generation of barcoded nucleic acids, or (ii) generating a barcoded copy of the target nucleic acid; and detecting the presence of the barcode in the target nucleic acid or copy thereof.

In some embodiments, the disclosure provides a method for determining the location of a non-canonical feature in a target nucleic acid at a single base resolution, the method comprising: contacting the target nucleic acid with a nucleic acid-binding molecule as described herein; either (i) transferring the nucleic acid barcode to the target nucleic acids to generate barcoded target nucleic acid, in an environment that substantially prevents off-target generation of barcoded nucleic acids, or (ii) generating a barcoded copy of the target nucleic acid; and detecting the presence of the barcode in the target nucleic acid or copy thereof; wherein the nucleic acid-binding molecule comprises a binding domain capable of one or more of the following: inducing a mutation in the target nucleic acid, or preventing polymerase bypass and therefore causing truncation during copying of the target nucleic acid.

In some embodiments, the disclosure provides nucleic acid-binding molecules comprising a base editing enzyme, wherein the base editing enzyme is a deaminase.

Also provided herein is a complex comprising a nucleic acid-binding molecule bound to a target nucleic acid.

Also provided herein is a substrate coupled to a nucleic acid-binding molecule as described herein.

Also provided herein is a polymer coupled to a nucleic acid-binding molecule as described herein.

These and other aspects of the invention will be apparent upon reference to the following detailed description, claims, embodiments, procedures, compounds, and/or compositions and associated background information and references, which are hereby incorporated in their entirety.

BRIEF DESCRIPTION OF THE DRAWINGS

FIG. 1A shows a double-stranded nucleic acid plus a base modification (i.e., a non-canonical feature). FIG. 1B shows a single-stranded nucleic acid with a base modification. FIG. 1C shows a single-stranded nucleic acid with a structural element (i.e., a non-canonical feature). FIG. 1D shows a binding domain conjugated to an adapter (e.g., an adapter comprising or consisting of a barcode sequence).

FIG. 1E shows the binding of a nucleic acid-binding molecule comprising a double-stranded barcode to a double-stranded nucleic acid with a modification. FIG. 1F shows the binding of a nucleic acid-binding molecule comprising a single-stranded barcode to a single-stranded nucleic acid with a modification. FIG. 1G shows the binding of a structure-specific nucleic acid-binding molecule to a single-stranded nucleic acid with a non-canonical structural element.

FIGS. 2A-2G are schematics showing the architecture of various DNA adapters. FIG. 2A shows an adapter comprising either a UFP or a URP. FIG. 2B shows an adapter which may be used for library preparation by circularization. FIG. 2C shows an adapter which may be used for barcode transfer by ligation. FIG. 2D shows adapters which may be used for single or multiple barcode transfer by primer extension. FIG. 2E shows an adapter comprising random or targeted feet and a stem region for internal priming and long read construction. FIG. 2F shows an adapter which may be used for internal priming and short read construction. FIG. 2G shows an adapter that may be used for barcoding by primer extension and targeting a DNA editing enzyme to the binding domain via hybridization to an DNA address. As shown in the legend, "UFP" is an abbreviation for universal forward primer, "URP" is an abbreviation for universal reverse primer, "MBC" is an abbreviation for modification-encoding barcode, "UMI" is an abbreviation for unique molecular identifier, and "CLS" is an abbreviation for cleavage site. "SP" is an abbreviation for spacer.

FIG. 14B also shows an illustrative method for cyclic profiling using differential base editing directed by different DNA addresses (Address 1, Address 1', Address 2, Address 2').

FIGS. 15A-15D is a series of schematics showing an illustrative method for RNA profiling by tagmentation.

In FIG. 20A, an exemplary antibody is labeled at a 10 to 50-fold molar excess of HyNic over antibody. Analysis by non-reducing SDS gel electrophoresis shows the associated labeling stoichiometries. FIG. 20B shows the result for labeling several RNA modification-specific antibodies with the same DNA adapter at a 20-fold excess of HyNic. The obtained labeling stoichiometries depended on the isotype of the antibody.

FIGS. 21A-21E illustrates the functional impact of different antibody labeling methods and labeling stoichiometries. FIG. 21A-21C show ELISA binding curves before or after random labeling of antibodies with HyNic chemistry. The affinity of the nucleic acid binding molecules is 10-15- fold reduced compared to the unlabeled antibodies. FIG. 21D-21E compares labeling of an anti-m6A antibody either by random HyNic chemistry or by site-selective glycan chemistry. FIG. 21D shows the SDS gel of the nucleic acids binding molecule demonstrating the attachment of 1 or 2 adapters to the antibody. FIG. 21E illustrates retention of the binding activity with glycan labeling, as measured by ELISA.

FIGS. 23A-23D shows experimental approaches for preparing an RNA library for barcoding by primer extension by attaching a universal sequence to the 3' end. FIG. 23A provides an overview of methods for introducing a spacer of known sequence (e.g. SEQ ID NO: 55) by homopolymer tailing or by ligation. FIG. 23B-23C provides experimental results for the enzymatic A-tailing of RNA targets. FIG. 23B demonstrates the concept of controlling the size of the A-tail by adding a poly-dT competitor oligonucleotide (($dT)_{20}$) to the reaction. Without poly-dT competitor, the A-tail has a broad size distribution between 100 and 200b. With poly-dT competitor, the A-tail is about 25b long. FIG. 23C shows experimental results for A-tailing at different temperatures and with poly-dT competitors of different lengths (($dT)_{10}$=10b, ($dT)_{20}$=20b, ($dT)_{30}$=30b). FIG. 23D shows data for attaching a universal sequence to the 3' end of RNA by single-stranded ligation. A 30b degenerate RNA library is ligated to a 10b, 20b, 30b and 50b universal sequence. The formation of ligation products is plotted as a function of time, revealing faster reaction rates for universal sequences of intermediate length (20 and 30b).

FIG. 23E compares the barcoding yields using DNA adapters with an 8b (adap-SP8), 10b (adap-SP10) or 12b (adap-SP12) spacers. While the barcoding yield is low for a 50b RNA target (long RNA) regardless of spacer length, a 50b DNA target and 15b RNA target are readily extended with an 8b spacer (adap-SP8). This finding suggests that the barcoding yield is dictated by the accessibility of the target spacer and that stable secondary structures as typical for longer RNA may obstruct access. Increasing the spacer length from 8 to 12b is not sufficient to compete with intramolecular secondary structure. FIG. 23F shows generally improved barcoding yields at higher reaction temperature and time, and with the addition of DMSO. Nearly complete barcoding is obtained with an 18b spacer adapter (adap-18SP).

In FIG. 24A-24B the nucleic acid binding molecules pull down their cognate targets, and the addition of the primer extension mix triggers barcode transfer. The results demonstrate that barcoding is more efficient with the nucleic acid binding molecule than with free adapters. FIG. 24A emphasizes the importance of the appropriate spacer length. Because Ab05 and Ab10 are functionally impacted by labeling, a 12b spacer is required to restore their binding activity. For random labeled m6A antibody (Ab05) the 12b spacer supports barcoding of the correct target, whereas the wrong target is barcoded by the anti-inosine antibody (Ab10). FIG. 24B shows that both antibodies are capable of on-target barcoding via a 8b spacer when labeled site-selectively. FIG. 24C provides an example for barcoding by ligation using the protein G bead assay format. An m6A antibody (Ab01) is site-specifically labeled with adapter yielding the nucleic acid binding molecule (BAC01). Barcoding with BAC01 is more efficient than the ligation of free adapter.

FIG. 25 describes the preparation of beads with adjustable capture molecule (e.g. Capture probe) density. Beads with capture molecules at single molecule distance provide an assay format for barcoding with freely diffusing nucleic acid binding molecules. The nucleic acid hybridization probe (capture molecule)(SEQ ID NO: 20) is co-immobilized together with the passivating molecule. The graph shows the number of molecules per bead obtained for different ratios of grafting to passivation molecules, as determined by qPCR.

FIGS. 26A-26C provide results for barcoding in solution and on single molecule beads (c.f. FIG. 25) and highlights the importance of controlling the intermolecular distance. FIG. 26A illustrates the preparation of a nucleic acid binding molecule composed of streptavidin and biotinylated DNA adapters. Depending on the ratio of streptavidin to adapters, a nucleic acid binding molecule with 1, 2, 3 or 4 adapters forms, as identified by native gel electrophoresis. The nucleic acid molecule with a 1:2 ratio of streptavidin:adapter is selected for barcoding experiments. FIG. 26B depicts the results for barcoding in solution. The biotin-specific nucleic acid binding molecule is incubated with a mix of biotin and m6A-modified RNA. Barcoding by ligation is initiated by adding T4 RNA ligase I (T4 Rnl1). The intermolecular spacing is gradually decreased by adding 0-25% polyethylene glycol (PEG8k). Barcoding is specific at low concentrations of PEG8k, whereas it becomes increasingly non-specific at higher concentrations due to crosstalk between molecules. FIG. 26C shows the reaction of the same assay components but with the RNA targets being immobilized on beads by sequence specific hybridization. In this experiment, the intermolecular distance is varied by using beads with a different ratio of grafting:passivating molecules (c.f. FIG. 25). The data indicate cross-talk with beads with a 1:100 ratio of grating:passivating molecule, whereas barcoding is specific for biotin at a 1:1,000 ratio.

FIG. 28 shows the size, quantity and cellular localization of expression products of different fusion proteins, analyzed by SDS gel electrophoresis.

FIGS. 29A-29B shows the success of purifying the MBD-TEV-APOBEC1-Spycatcher fusion protein by Ni-column (FIG. 29A) and by MBD-column (FIG. 29B).

FIG. 30 is a schematic of the protein domain organization and the amino acid sequences of fusion proteins designed for position marking of nucleic acid modifications by targeted deamination (SEQ ID NOs: 42 and 43).

FIG. 31 shows deamination activity of APOBEC fusion proteins expressed by in vitro translation. TOP: a schematic of the USER assay used for APOBEC activity testing. BOTTOM: data of deamination activity from serial dilutions (1:1, 1:2, 1:4, 1:8, 1:16) of cell-free extracts containing APOBEC enzymes. The first two lanes are controls showing 100% cytidine or 100% uracil detection by USER cleavage.

FIG. 33 shows an example of using the PPA assay to measure the activity of a commercial APOBEC3A enzyme. The PPA experiment was performed on both RNA and DNA targets, using reverse transcriptase (MuLV) and DNA polymerase (Klenow exo-), respectively, as the PPA enzyme. APOBEC3A is highly active on DNA but has weak activity on RNA.

FIG. 34 illustrates the PPA assay that was used to measure the size of the deaminase activity window after targeting the enzyme by Spytag peptide. Spytag reacts rapidly with Spycatcher, thus tethering the APOBEC3A-Spycatcher fusion protein to particular sites of the DNA template (e.g. SEQ ID NO:50). TOP: a schematic of the assay design. "C"=cytidine as editing sites. Arrows=deamination activity towards different sites. The darker color represents stronger deamination activity, the lighter color represents weaker deamination activity. BOTTOM: Target oligo sequences used in the assay and FAM labeled primer used for analysis (SEQ ID NO:51). SpyTag labeling sites (distal and proximal, SEQ ID NOs: 48 and 49, respectively) are indicated.

FIG. 35 shows targeted deamination by hAPOBEC3A (E109Q)-SpyCatcher. In the presence of Spytag, the cytidine that is closest to Spytag is preferably edited, indicating successful targeting. hAPOBEC3A(E109Q) alone or hAPOBEC3A(E109Q)-SpyCatcher with no SpyTag control show non-specific editing at all available sites. D: oligo with SpyTag at distal site from the first cytidine. P: oligo with SpyTag at the proximal site from the first cytidine. Bands which appear near the bottom of the gel (i.e., smaller bands) represent editing at the first cytidine, and bands appearing higher up in the gel (i.e., larger bands) represent editing at later cytidines.

DETAILED DESCRIPTION

Figure 1A:
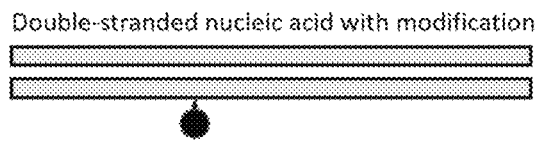
FIGS. 1A-1D are schematics showing functional elements of various molecules described herein.

Provided herein are compositions and methods for the multiplexed profiling of RNA and DNA modifications across transcriptomes and genomes, respectively. The methods combine molecular recognition of non-canonical features (e.g., base modifications, backbone modifications, lesions, and/or structural elements) of a target nucleic acid with a step of writing the information from this recognition event into the neighboring genetic sequence of the target nucleic acid using a barcode. The resultant barcoded nucleic acids are then converted into sequencing libraries and read by, for example, DNA/RNA sequencing methods or other methods. This step reveals the sequence of the barcode, which is correlated with the non-canonical feature in the target nucleic acid(s). Sequencing may also allow for localization of the non-canonical feature in the target nucleic acid(s). The high throughput profiling methods described herein allow for identification of the nature and location of several or all DNA/RNA modifications in parallel. These methods also allow for determination of abundance and stoichiometry of the DNA/RNA modifications.

In some embodiments, the disclosed methods are used to not only identify the modification on the target nucleic acid, but also to localize the modification on the target nucleic acid with a resolution as high as 1 base.

The present invention is described more fully hereinafter using illustrative, non-limiting embodiments, and references to the accompanying figures. This invention may, however, be embodied in many different forms and should not be construed as to be limited to the embodiments set forth below. Rather, these embodiments are provided so that this disclosure is thorough and conveys the scope described herein to those skilled in the art.

Unless otherwise defined, all technical and scientific terms used herein have the same meaning as commonly understood by one of ordinary skill in the art to which this disclosure belongs. The terminology used in the detailed description herein is for the purpose of describing particular embodiments only and is not intended to be limiting.

All publications, patent applications, patents, GenBank/Uniprot or other accession numbers and other references mentioned herein are incorporated by reference in their entirety for all purposes.

Definitions

The following terms are used in the description herein and the appended claims.

The singular forms "a," "an" and "the" are intended to include the plural forms as well, unless the context clearly indicates otherwise.

Furthermore, the term "about" as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features described herein can be used in any combination. Moreover, in some embodiments, any feature or combination of features set forth herein can be excluded or omitted. To illustrate further, if, for example, the specification indicates that a particular DNA base can be selected from A, T, G and/or C, this language also indicates that the base can be selected from any subset of these base(s) for example A, T, G, or C; A, T, or C; T or G; only C; etc., as if each such subcombination is expressly set forth herein. Moreover, such language also indicates that one or more of the specified bases can be disclaimed. For example, in some embodiments the nucleic acid is not A, T or G; is not A; is not G or C; etc., as if each such possible disclaimer is expressly set forth herein.

As used herein, the terms "reduce," "reduces," "reduction" and similar terms mean a decrease of at least about 10%, about 15%, about 20%, about 25%, about 35%, about 50%, about 75%, about 80%, about 85%, about 90%, about 95%, about 97% or more.

As used herein, the terms "increase," "improve," "enhance," "enhances," "enhancement" and similar terms indicate an increase of at least about 10%, about 15%, about 20%, about 25%, about 50%, about 75%, about 100%, about 150%, about 200%, about 300%, about 400%, about 500% or more.

The term "epigenetic change" is used herein to refer to a phenotypic change in a living cell, organism, etc., that is not encoded in the primary sequence (i.e., A, T, C, and G) of that cell's or organism's DNA. Epigenetic changes may include, for example, chemical alterations of nucleotides and/or histones (i.e., the proteins involved in coiling and packaging DNA in the nucleus). Illustrative DNA nucleotide modifications include the common epigenetic marker 5-methylcytidine (5mC) and its oxidation products 5-hydroxymethylcytidine (5hmC), 5-formylcytidine (5fC), 5-carboxymethylcytidine (5caC). 5mC is well known for its role in gene silencing, and a growing body of evidence suggests metabolic function for the oxidized intermediates 5hmC, 5fC, and 5caC on the pathway for demethylation of 5mC. Additional metabolically relevant DNA modifications include oxidized, alkylated, dimerized, cross-linked, and other chemically modified nucleotides associated with DNA damage. Such DNA modifications are relevant to understanding toxicity, but their distribution across the genome when damage occurs is not well understood. DNA modifications may have additional regulatory roles, for example as participants in G-quadruplex dynamics in promoter and other regions of the genome.

The term "epitranscriptomic change" is used herein to refer to a chemical modification of RNA that occurs during or after transcription. More than 170 distinct RNA modifications are known, including chemical changes to the nucleobases and to ribose and the phosphodiester backbone. RNA modifications are found in all types of RNA, including mRNA, tRNA, rRNA, lncRNA, miRNA, and they may alter cellular phenotypes by changing RNA structure and dynamics and/or by changing the molecular recognition of the RNA by other biological molecules such as proteins. Naturally occurring chemical RNA modifications of the epitranscriptome regulate a broad spectrum of functions in RNA metabolism, including RNA processing, splicing, polyadenylation, editing, structure, stability, localization, translation initiation, and gene expression. The epitranscriptome differs across cell types, metabolic conditions, and states of health, playing vital (but poorly understood) roles in the differentiation of cellular phenotype and function and helping to explain the dramatic phenotypic differences between cells of the same organism that possess an identical primary genetic sequence. Changes in the epitranscriptome are correlated with disease. For example, mRNA and ncRNA modifications are known to regulate spatiotemporal gene expression changes during cancer stem cell differentiation, thereby playing an orchestrating role in disease progression. Additionally, RNA modifications are strongly suspected of being a key mechanism by which RNA viruses (e.g. Coronaviridae and Flaviviridae) subvert the host and evade the innate immune system.

The term "genome" refers to all the DNA in a cell or population of cells, or a selection of specific types of DNA molecules (e.g., coding DNA, noncoding DNA, mitochondrial DNA, or chloroplast DNA.) The term "transcriptome" refers to all RNA molecules produced in one or a population of cells, or a selection of specific types of RNA molecules (e.g., mRNA vs. ncRNA, or specific mRNAs within an mRNA transcriptome) contained in a complete transcriptome. In some embodiments, a transcriptome comprises multiple different types of RNA, such as coding RNA (i.e., RNA that is translated into a protein, e.g., mRNA) and non-coding RNA. A non-limiting list of various types of RNA molecules found in a transcriptome, all of which may contain modified nucleosides, includes: 7SK RNA, signal recognition particle RNA, antisense RNA, CRISPR RNA, Guide RNA, long non-coding RNA, microRNA, messenger RNA, piwi-interacting RNA, repeat-associated siRNA, retrotransposon, ribonuclease MRP, ribonuclease P, ribosomal RNA, small Cajal body-specific RNA, small interfering RNA, smY RNA, small nucleolar RNA, small nuclear RNA, and trans-acting siRNA.

As used herein, the term "non-canonical feature" of a nucleic acid means a feature of a nucleic acid that is separate and distinct from its primary sequence. For example, a non-canonical feature may be a chemical modification to a DNA or RNA base, or to a DNA or RNA backbone. In some embodiments, a non-canonical feature may be a structural sequence, such as a hairpin or a loop. In some embodiments, a non-canonical feature may be a nucleic acid lesion, such as a DNA or RNA lesion. Other illustrative non-canonical structures include, but are not limited to, Z-DNA structures, G-quadruplexes, triplexes, i-motifs, bulges, abasic sites, triplexes, three-way junctions, cruciform structures, tetraloops, ribose zippers, pseudoknots, etc. Nucleic acids, including DNAs and RNAs, may comprise numerous non-canonical features. The frequency of these modifications varies widely depending on RNA and type of feature, although clusters of modifications may occur. In some embodiments, non-canonical features may result from DNA and/or RNA damage. The terms "non-canonical feature" and "modification" may be used interchangeably herein, as will be understood in context by a person of ordinary skill in the art.

As used herein, the term "target nucleic acid" refers to a nucleic acid comprising one or more non-canonical features. The nucleic acid-binding molecules described herein may bind to a target nucleic acid when the binding domain of the molecule recognizes the non-canonical feature.

As used herein, the term "substrate" will be used to refer to any solid support. For example, a substrate may be a bead, chip, plate, slide, dish, or 3-dimensional matrix. As described herein, the nucleic acid-binding molecules described herein may be coupled to one or more substrates, and a substrate may be coupled to one or more nucleic acid-binding molecules. Substrates may be formed from a variety of materials. In some embodiments, the substrate is a resin, a membrane, a fiber, or a polymer. In some embodiments, the substrate comprises sepharose, agarose, cellulose, polystyrene, polymethacrylate, and/or polyacrylamide. In some embodiments, the substrate comprises a polymer, such as a synthetic polymer. A non-limiting list of synthetic polymers includes: poly(ethylene)glycol, polyisocyanopeptide polymers, polylactic-co-glycolic acid, poly(ε-caprolactone) (PCL), polylactic acid, poly(3-hydroxybutyrate-co-3-hydroxyvalerate) (PHBV), chitosan and cellulose.

As used herein, the term "barcode" refers to a synthetically produced nucleic acid. Unique barcodes may be assigned to specific nucleic acid modifications, to allow for specific identification of those modifications in the methods described herein. Accordingly, a barcode is "unique" to a non-canonical modification if it is used specifically to identify that modification in one or more of the methods described herein. Barcodes may be produced using methods known in the art, such as solid phase oligonucleotide synthesis. In some embodiments, a barcode may be a DNA barcode (i.e., it may comprise a DNA sequence). In some embodiments, a barcode may comprise a synthetic DNA structure, such as a peptide nucleic acid (PNA) or a locked nucleic acid (LNA). In some embodiments, the synthetic DNA structure may comprise one or more modified bases. In some embodiments, a barcode may be an RNA barcode (i.e., it may comprise an RNA sequence). Barcodes may be any length, such as a length in the range of about 4 to about 150 nucleotides. In some embodiments, a barcode is about 4 to about 20 nucleotides in length, such as about 4, about 5, about 6, about 7, about 8, about 9, about 10, about 11, about 12, about 13, about 14, about 15, about 16, about 17, about 18, about 19, or about 20 nucleotides in length. Typically, a barcode will comprise a rationally designed sequence that is not found in the genome of any known organism. However, in some embodiments, a barcode may comprise a known sequence. For example, the sequence of the barcode may comprise a signature associated with a pathogen or other biological material. In some embodiments, a barcode may comprise a sequence configured to facilitate a sequencing reaction. The terms "barcode" and "adapter" may sometimes be used interchangeably herein. As will be understood in the art, an adapter may, in some embodiments, consist of a barcode. In some embodiments, an adapter may comprise a barcode and one or more additional elements as described below and as shown in FIGS. 2A-2G.

The term "amplify," when used in reference to a nucleic acid, means producing copies of that nucleic acid. Nucleic acids may be amplified using, for example, polymerase chain reaction (PCR). Alternative methods for nucleic acid amplification include helicase-dependent amplification (HAD), recombinase polymerase amplification (RPA), loop mediated isothermal amplification (LAMP), nucleic acid sequence-based amplification (NASBA), self-sustained sequence replication (3SR), and rolling circle amplification (RCA).

As used herein the term "intra-complex adapter transfer" or "intra-complex barcode transfer" refers to transfer of an adapter and/or barcode to a target nucleic acid (e.g., a DNA or an RNA), while a nucleic acid-binding molecule is bound thereto. Thus, in this context, the term "complex" refers to a complex formed between the target nucleic acid and its cognate nucleic acid-binding protein.

As used herein, the terms "crosstalk", "barcode crosstalk", and similar terms refer to the off-target transfer of a nucleic acid barcode. For example, barcode crosstalk may occur when the barcode of a nucleic acid-binding molecule is transferred to a nucleic acid that is not bound to the binding domain of the nucleic acid binding molecule.

The term "DNA address" refers to a DNA or RNA sequence and/or its complement that is used as a programmable binding element, to facilitate a specific binding event. For example, a deaminase may be coupled to a DNA or RNA sequence (i.e., a first DNA address) that binds to a target DNA or RNA sequence (e.g., a second DNA address), directing the deaminase thereto. Binding of a first DNA address to a second DNA address is shown, for example in FIG. 14B (e.g., address 1 and address 1').

A "nucleic acid lesion" such as a "DNA lesion" or a "RNA lesion" is a chemical modification of the nucleic acid that may occur as a result of endogenous processes and/or exogenous agents. For example, DNA lesions may be caused by oxidative damage (e.g. 8-oxoguanine), reaction with electrophiles and alkylating agents including those present in charred meats and in tobacco smoke (benzo[a]pyrene adducts and alkylated nucleobases), UV damage (cyclobutane pyrimidine dimers and 6-4 pyrimidine-pyrimidine photoproducts), metal complexation (mercury complexes and platinated crosslinks). DNA lesions occurring due to endogenous processes occur frequently—it is estimated that they occur around 50,000 times per day in each cell. DNA lesions are typically repaired by a variety of repair enzymes or bypassed by lesion bypass polymerases during replication of the genetic code, the latter process causing mutation. Mutations that confer unnatural cell growth and proliferation are drivers of cancer. Mutations are readily detected by conventional DNA sequencing, but the lesions themselves cannot be detected using standard DNA sequencing workflows. Lesions are not distributed uniformly throughout the genome, and the efficacy of repair is tied to DNA locus and cell state. Moreover, the most common cancer chemotherapeutics (cisplatin, gemcitabine, etc.) induce DNA damage, so mapping DNA damage across the human genome offers enormous potential to understand aging and cancer etiology and to improve the effectiveness and lower the toxicity of cancer chemotherapeutics.

Nucleic Acid-Binding Molecules and Methods for Making the Same

Provided herein are nucleic acid-binding molecules comprising a binding domain and an adapter, each of which are described in greater detail below.

Adapters

As used herein, the term "adapter" refers to any short nucleic acid sequence that can be coupled to the end of a DNA or RNA molecule and that confers some functionality. For example, in some embodiments, an adapter may facilitate sequencing and/or identification of a DNA or RNA molecule.

In some embodiments, the adapter comprises a 5' phosphate. In some embodiments, the adapter comprises a 3' phosphate. In some embodiments, the adapter comprises a 5' phosphate and a 3' phosphate. In some embodiments, an adapter is single-stranded. In some embodiments, an adapter is double-stranded. In some embodiments, a double-stranded adapter may comprise a single-stranded adapter hybridized to a complementary oligonucleotide.

In some embodiments, an adapter may be cleavable. For example, the adapter may comprise one or more cleavage sites. The cleavage site may comprise, for example, one or several uracil bases, a sequence recognized by an enzyme (e.g., a restriction enzyme or other nuclease), or a synthetic chemical moiety.

In some embodiments, an adapter comprises a universal forward primer (UFP). In some embodiments, an adapter comprises a universal reverse primer (URP). In some embodiments, an adapter comprises a UFP and a URP. In some embodiments, an adapter consists of a UFP or a URP. The UFP and URP sequences are DNA sequences that do not occur naturally, and allow for selective amplification of only those sequences that were introduced into a target nucleic acid (or copy thereof). During sequencing, the UFP and/or URP are annealed to the DNA target, to provide an initiation site for the elongation of a new DNA molecule (i.e., a copy thereof). A list of illustrative UFPs and URPs can be found at the world wide web address lslabs.com/resources/universal-primer-list. In some embodiments, universal primer sequences used in the adapters (and transferred to the target nucleic acid) are compatible with established DNA sequencing platforms and may be used to introduce surface adapters such as Illumina P5 and P7 in downstream PCR reactions.

In some embodiments, an adapter may comprise a barcode, such as a modification encoding barcode (MBC). An MBC is a short, unique nucleic acid sequence. Each MBC is used in connection with a specific epigenetic or epitranscriptomic modification, to help with the identification and/or analysis thereof. For example, an MBC may be used in an adapter that is conjugated to a binding domain that is specific for a particular non-canonical feature. In some embodiments, an adapter may consist of a barcode. In some embodiments, an adapter may consist of an MBC.

In some embodiments, an adapter may comprise a unique molecular identifier (UMI). A UMI consists of a short, random sequence that has $4^{[UMI\ Length]}$ unique variants. For example, a 10-base long UMI can encode 1,048,576 ($4^{10}$) unique molecules. UMIs are used for the absolute quantification of sequencing reads in order to correct for PCR amplification bias and errors. For example, an RNA sample may contain 100 copies of transcript A and 100 copies of transcript B. After PCR amplification, 1M copies of transcript A and 2M of transcript B may be detected, because transcript B amplifies more efficiently. UMI tagging, however, links 100 unique UMIs to A and 100 unique UMIs to B. When using a UMI for transcript A, 10,000 copies of 100 UMI variants will be detected, and for transcript B 20,000 copies of 100 UMI variants will be detected. Counting the number of UMI variants instead of counting the number of reads provides the absolute number of molecules.

Typically, a UMI length is chosen to avoid UMI collisions, defined as the event of observing two reads with the same sequence and same UMI but originating from two different genomic molecules. UMI collision is a function of the number of UMIs used, the number of unique alleles and the frequency of each allele in the population. The ideal length of UMIs also depends on the error rate of the sequencing platform and on the sequencing depth. Sequencing platforms with higher error rates require longer UMIs because errors in the UMI may cause accidental UMI collision. Targeted sequencing, where the sequencing depth for selected loci is greater than in whole genome sequencing, also uses longer UMIs because many alleles from different genomic molecules will share the same sequence. Excessively long UMIs are avoided because they require a greater number of sequencing cycles, thus shortening the read of the actual target sequence. Long UMIs may also cause mispriming in PCR reactions and produce sequencing artifacts. UMIs are typically in the range of about 3 to about 25 nucleotides. In some embodiments, a UMI is about 3 to about 20 nucleotides in length, such as about 3, about 4, about 5, about 6, about 7, about 8, about 9, about 10, about 11, about 12, about 13, about 14, about 15, about 16, about 17, about 18, about 19, or about 20 nucleotides in length. In some embodiments, the UMI may be 8 nucleotides in length. In some embodiments, the UMI may be 10 nucleotides in length.

FIGS. 2A-2G illustrate exemplary nucleic acid adapter architectures, and the legend provides a description of each element used therein. These adapters are labeled Type A, Type B, Type C, Type D, Type E, Type F, and Type G for ease of reference.

The adapters shown in FIG. 2A (Type A) represent minimal adapters that may comprise either a UFP or a URP sequence. Type A adapters do not contain any sequence that can be used for identification or analysis of a non-canonical nucleic acid feature, but are instead used for library construction. In some embodiments, Type A adapters are coupled to nucleic acid molecules that do not comprise a non-canonical feature. In some embodiments, Type A adapters are coupled to nucleic acid molecules that do contain a non-canonical feature after introducing a barcoded adapter to the other end of the target nucleic acid. For example, Type A adapters may be used to cap and prepare a nucleic acid for PCR amplification after one or more barcodes have been added.

The adapters shown in FIG. 2B-2G each comprise an MBC, which is specific for one non-canonical DNA/RNA feature (e.g., a modified base). As shown in FIG. 2B, Type B adapters may be used for library preparation workflows that involve circularization of cDNA. They comprise a cleavage site (CLS). Cleavage of Type B adapters may be performed prior to PCR amplification. As shown in FIG. 2C, Type C adapters lack the CLS and contain only one universal primer region. Type C adapters may be used, for example, in barcode transfer by ligation reactions. They may be combined with methods for second strand synthesis, such as template switching oligonucleotides according to Smart-Seq technology or another adapter ligation. As shown in FIG. 2D, Type D adapters are specifically designed for encoding by primer extension. Type D adapters may comprise one 3'-terminal spacer (SP) or two spacer regions (e.g. SP1, SP2) at either ends. The reaction is initiated by ligating a short spacer region (SP) onto the 3' end of the target nucleic acid and binding of a Type D adapter with complementary spacer. The spacer may be universal across all nucleic acid-binding molecules and cycles, unique to each type of nucleic acid-binding molecule, or unique to each cycle of barcoding. In some embodiments, an adapter comprises one, two, three, or four spacers. In some embodiments, an adapter comprises one spacer. In some embodiments, an adapter comprises two spacers. In some embodiments, a spacer is 3, 4, 5, 6, 7, 8, 9, 10, 11, 12, 13, 14, 15, 16, 17, 18, 19, or 20 nucleotides in length. In some embodiments, a spacer is 6 nucleotides in length. In some embodiments, a spacer is 7 nucleotides in length. In some embodiments, a spacer is 8 nucleotides in length. In some embodiments, the spacer comprises SEQ ID NO: 19. Type D adapters may be used, for example, in a single barcode transfer by primer extension reactions, or for multiple, sequential barcode transfers. Multiple cycles of barcoding may be used to interrogate only one, or a subset of non-canonical features in each cycle. For example, the first encoding cycle may employ nucleic acid binding molecules specific for m5C. The second encoding cycle may employ nucleic acid binding molecules specific for m6A. The third encoding cycle may employ nucleic acid binding molecules specific to inosine, etc. In another embodiment, the first cycle may interrogate m5C and m6A, and the second cycle may interrogate inosine. In another embodiment, the first encoding cycle may interrogate all non-canonical features, and the second encoding cycle may interrogate all non-canonical features for a second time. As shown in FIG. 2E, Type E adapters take the form of a hairpin with random feet that bind to the target nucleic acid near a modification if positioned via a nucleic acid-binding molecule comprising an adapter. The feet may be random sequences or target regions of interest. Furthermore, they may contain modified bases that increase the melting temperature of nucleic acid duplexes and counteract strand displacement by reverse transcriptases and DNA polymerases. In some embodiments, the stem region of the hairpin anneals stably and is as short as possible to minimize redundant sequencing content. Like spacers, stems can be universal or diverse across all nucleic acid-binding molecules. In some embodiments, the loop region is cleavable. Type E adapters may be used, for example, for internal priming and long read construction. As shown in FIG. 2F, Type F is a modified version of a Type E adapter that comprises a disconnected loop. The overall architecture of the Type F adapter may be Y-shaped, L-shaped, or some combination thereof. As shown in FIG. 2G, Type G adapters are derived from Type D adapters by including a DNA address. A DNA address may be included in any of the adapter architectures.

In some embodiments, an adapter comprises a UFP, a URP, or a UFP and a URP. In some embodiments, an adapter comprises a UFP and/or a URP, and also comprises an MBC. In some embodiments, an adapter comprises a UFP and/or a URP, an MBC, and a UMI. In some embodiments, and adapter comprises a UFP and/or a URP, a MBC, a UMI, and a CLS. In some embodiments, an adapter comprises a UFP and/or a URP, a MBC, a UMI, a CLS, and a SP. In some embodiments, an adapter comprises a UFP, a CLS, a URP, a UMI, and an MBC. In some embodiments, an adapter comprises a UFP, a UMI, and an MBC. In some embodiments, an adapter comprises a URP, a UMI, and an MBC. In some embodiments, an adapter comprises a first SP, an MBC, a UMI, and a second SP.

In some embodiments, an adapter has a hairpin shape. In some embodiments, an adapter comprising an MBC has a hairpin shape. In some embodiments, an adapter comprising an MBC has a hairpin shape, wherein the hairpin comprises a stem region that is 4-20 base pairs in length, and two random or targeted feet, wherein each foot is about 4-10 base pairs in length.

In some embodiments, an adapter has an L shape, a Y shape, or some combination thereof. In some embodiments, an adapter having an L shape or a Y shape comprises a UFP, an MBC, and an URP. In some embodiments, an adapter having an L shape or a Y shape comprises a UFP, an MBC, and a URP, wherein the adapter comprises a stem region having a length of about 4 to about 20 base pairs, and further comprises random or targeted feet, wherein each foot has a length of about 4-10 base pairs.

The adapters described herein may, in some embodiments, comprise one or more linkers, such as linkers which help link the binding domain to the adapter. The linkers may comprise polyethylene glycol, hydrocarbons, peptides, DNA, or RNA. The linkers may vary in length. Longer linkers may be used in situations where a non-canonical feature of a DNA or RNA is located far from the 5' or 3' end of a nucleic acid sequence. Shorter linkers may be used in situations where a non-canonical feature of a DNA or RNA is located relatively close to a 5' or a 3' end of a nucleic acid sequence.

In some embodiments, the adapters, or a linker sequence contained therein, are cleavable. For example, the adapters may comprise one or more cleavage sites. The adapter may be chemically, photochemically or enzymatically cleavable. The cleavage sites may comprise, for example, one or several uracil bases, a sequence recognized by an enzyme (e.g., a restriction enzyme or other nuclease), or a synthetic chemical moiety, for example disulfides, carbonate ester, hydrazones, cis-aconityl, or β-glucuronide.

As described in further detail below, adapters may be fused to a single- or double-stranded target nucleic acid (e.g., a DNA or RNA) using a barcode transfer reaction.

In some embodiments, primer extension comprises appending a 3'poly-rA tail to an RNA target. In some embodiments, primer extension comprises appending a 3'poly-rA tail to an RNA target as depicted in FIG. 23A. The 3'poly-rA tail is appended by polyadenylation using any known poly (A) polymerase (e.g. *E. coli* poly (A) polymerase). In some embodiments, the RNA target is incubated with poly (A) polymerase and a competitor poly-dT oligonucleotide. Co-treatment with a poly (A) polymerase and a competing poly-dT oligonucleotide controls the length of the appended 3'poly-rA tail. Typically, polyadenylation yields a mean 3'poly-rA tail length of about 150 bases. In some embodiments, the length of the 3'poly-rA tail is about 5, about 10, about 15, about 20, about 25, about 30, about 35, about 40, about 45, about 50, about 55, or about 60 bases in length.

In some embodiments, primer extension comprises appending a 3'poly-U tail, a 3'poly-G tail, a 3'poly-A tail or a 3'poly-G tail to an RNA target. The homopolymer tail is appended using any known poly (U) polymerase (e.g. *Schizosaccharomyces pombe* Cid1). In some embodiments, the RNA target is incubated with poly (U) polymerase, GTP and a competitor poly-dC oligonucleotide. Co-treatment with a poly (U) polymerase and a competing poly-dC oligonucleotide controls the length of the appended 3'poly-G tail. In some embodiments, the length of the 3'poly-G tail is about 5, about 10, about 15, about 20, about 25, about 30, about 35, about 40, about 45, about 50, about 55, or about 60 bases in length.

In some embodiments, the adapter comprises SEQ ID NO: 56. In some embodiments, the adapter comprises SEQ ID NO: 57. In some embodiments, the adapter comprises SEQ ID NO: 6. In some embodiments, an adapter comprising a spacer comprises SEQ ID NO: 25. In some embodiments, an adapter comprising a spacer comprises SEQ ID NO: 26. In some embodiments, an adapter comprising a spacer comprises SEQ ID NO: 27. In some embodiments, an adapter comprising a spacer comprises SEQ ID NO: 38. In some embodiments, a biotin adapter comprises SEQ ID NO: 33. In some embodiments, a DBCO labeled adapter comprises SEQ ID NO: 22. In some embodiments, a site-clicked adapter comprises SEQ ID NO: 39.

Binding Domains

As used herein, the term "binding domain" refers to any nucleic acid, polypeptide, etc. that binds to a non-canonical feature of a target nucleic acid, such as a modified nucleoside. The term "binding domain" may be used interchangeably herein with the terms "binder," "recognition element," "antibody," etc., as will be understood from context by those of skill in the art. In some embodiments, a binding domain binds to a non-canonical feature of a target nucleic acid. In some embodiments, the binding domain does not bind to any nucleic acid features flanking the non-canonical feature. In some embodiments, a binding domain binds to both (i) a non-canonical feature of a target nucleic acid, and (ii) one or more nucleic acid features flanking the non-canonical feature (e.g., a nucleobase, a sugar, a phosphate, or a combination thereof). In some embodiments, the binding domain may bind a conserved sequence motif. For example, $m^6A$ often occurs in the following motif: $GG(m^6A)CT$. Accordingly, when a binding domain binds to $m^6A$, it may also bind to one or more of the nucleic acids (e.g., GG or CT) that are adjacent thereto. As another example, a binding domain may bind to all or part of the anticodon loop of tRNA. In some embodiments, the binding domain binds a tRNA wherein the binding domain binds a modification and a known sequence on the tRNA.

The nucleic acid-binding molecules described herein comprise one or more binding domains, wherein the binding domains bind specifically to a non-canonical feature of a DNA or an RNA. The binding domains described herein may be any protein, nucleic acid, or fragment or derivative thereof that is capable of recognizing and binding to a non-canonical feature of a target nucleic acid. For example, in some embodiments, the binding domain comprises an antibody, an aptamer, a reader protein, a writer protein, an eraser protein, an engineered macromolecule scaffold, an engineered protein scaffold, or a selective covalent capture reagent, or a fragment or derivative thereof. In some embodiments, the binding domain comprises an IgG antibody, an antigen-binding fragment (Fab), a single chain variable fragment (scFv), or a heavy or light chain single domain ($V_H$ and $V_L$). In some embodiments, the binding domain comprises a heavy-chain antibody (hcAb) or the $V_H H$ domain of a hcAb (nanobody). In some embodiments, the binding domain comprises an engineered protein scaffold such as an adnectin, an affibody, an affilin, an anticalin, an atrimer, an avimer, a bicyclic peptide, a centyrin, a cys-knot, a darpin, a fynomer, a kunitz domain, an obody or a pronectin.

IgG antibodies are the predominant isotype of immunoglobulins. IgGs comprise two identical heavy chains and two identical light chains that are covalently linked and stabilized through disulfide bonds. IgGs recognize an antigen via the variable N-terminal domains of the heavy ($V_H$) and the light ($V_L$) chain and six complementarity determining regions (CDRs). Antibodies that bind to some modified DNA and RNA bases are available commercially. For example, several companies sell antibodies specific for $hm^5C$, including Active Motif and Sigma. Eurogentec S.A. (Belgium) sells a monoclonal antibody that binds to $m^5C$. Megabase Research Products (USA) sells rabbit polyclonal sera that bind to $m^5C$ 6-methyladenosine and 7-methylguanosine. Abcam (USA) sells recombinant antibodies against the RNA modifications m6A, ac4C, m1A, m2.2G, m4C, m2A, m6.6A and m8A.

Antibodies that bind to modified bases also be can developed according to methods known and practiced by persons of ordinary skill in the art. In some embodiments, the antibodies may be monoclonal antibodies, polyclonal antibodies, or functional fragments or variants thereof. The term "antibody" as used herein covers any specific binding substance having a binding domain with the required specificity. Thus, this term covers antibody fragments, derivatives, functional equivalents, and homologues of antibodies, including any polypeptide comprising an immunoglobulin binding domain, whether natural or synthetic, monoclonal or polyclonal. Chimeric molecules comprising an immunoglobulin binding domain, or equivalent, fused to another polypeptide are also included.

In some embodiments, the binding domain may comprise a nanobody. Nanobodies comprise a single variable domain ($V_H H$) of heavy chain antibodies, as produced by camelids and several cartilaginous fish. The $V_H H$ domain comprises three CDRs that are enlarged compared to the CDRs of IgG antibodies, and provide a sized antigen-interacting surface that is similar in size compared to that of IgGs (i.e., about 800 Å2). Nanobodies bind antigens with similar affinities as IgG antibodies, and offer several advantages relative thereto:

they are smaller (15 kDa), less sensitive to reducing environments due to fewer disulfide bonds, more soluble, and devoid of post-translational glycosylation. Nanobodies can be produced in bacterial expression systems, and they are therefore amenable to affinity and specificity maturation by phage and other display techniques. Other advantages include improved thermal stability and solubility, and straightforward approaches to site-specific labeling. Due to their small size, nanobodies can form convex paratopes making them suitable for binding difficult-to-access antigens. Illustrative methods for producing nanobodies include immunizing the respective animal (e.g., a camel) with the antigen of interest, by further evolving an existing naïve library, or by a combination thereof.

In some embodiments, the binding domain comprises a reader protein, a writer protein or an eraser protein. A "reader protein" is a protein that selectively recognizes and binds specific chemical modifications on a DNA or RNA. A "writer protein" is a protein that adds specific chemical modifications to a DNA or RNA. An "eraser protein" is an enzyme which removes specific chemical modifications from a DNA or RNA. In some embodiments, the binding domain comprises a fragment or derivative of a reader protein, a writer protein, or an eraser protein. In some embodiments, the binding domain comprises an engineered form of a reader, writer, or eraser protein, such as a form which has been engineered to retain nucleic acid binding but lacks any enzymatic activity. Illustrative reader, writer, and eraser proteins that may be used in the binding domains described herein are listed in Table 1 and Table 2. Additional reader, writer, and eraser proteins are listed at the following world wide web address: rnawre.bio2db.com.

TABLE 1

Reader, writer, and eraser proteins

| Type | Family | Specific Protein Examples |
| --- | --- | --- |
| Writer | Methyltransferase | METTL3, TRMT, NSUN, ALKBH8, RNMT, MePCE, BCDIN3D |
|  | H/ACA ribonucleoprotein complex subunit DKC1; catalyzes pseudouridylation of rRNA | DKC1 |
|  | RNA cytidine acetyltransferase; catalyzes formation of N4-acetylcytidine (ac4C) | NAT10 |
|  | tRNA dimethylallyltransferase; catalyzes formation of N6-(dimethylallyl)adenosine (i6A) | TRIT1 |
| Eraser | Demethylases of the ALKBH family | FTO, ALKBH5 |
| Reader | YTH domain proteins | YTHDC1, YTHDF1, YTHDF2 |
|  | THO complex subunit 4 | ALYREF |

TABLE 2

RNA modifying proteins, RNA modifications produced thereby, and relation to cancer development

| Nt. | RNA Modification | RNA-modifying proteins | Site-specific position & RNA species | Associated Cancer |
| --- | --- | --- | --- | --- |
| A | m1A | TRMT6 (W) | A58 tRNA-Met | Gastrointestinal Cancer (Onc) |
|  |  |  | mRNA | Gastrointestinal Cancer (Onc) |
|  |  | TRMT10C (W) | A9 tRNA mitochondrial | Gastrointestinal Cancer (Onc) |
|  |  | TRMT61A (W) | A58 tRNA | Gastrointestinal Cancer (Onc) |
|  |  |  | mRNA | Gastrointestinal Cancer (Onc) |
|  |  | ALKBH1 (E) | A58 tRNA | Cervix Cancer (Onc) |
|  |  | ALKBH3 (E) | mRNA (5'UTR near Start Codon) | Pancreatic Cancer (Onc) |
|  |  |  |  | Breast Cancer (Onc) |
|  |  |  |  | Ovarian Cancer (Onc) |
|  |  |  | A58 tRNA | Cervix Cancer (Onc) |
| A | ms2i6A | CDK5RAP1 (W) | A37 tRNA mitochondrial | Breast Cancer (Onc) |
|  |  |  |  | Melanoma (Onc) |
| A | i6A | TRIT1 (W) | A37 tRNA-SelenoCys | Lung Cancer (TS) |
|  |  |  |  | Gastric Cancer |
| A | m6A | METTL3 (W) | mRNA (5'UTR, ORF, 3'UTR) | Endometrial Cancer (TS) |
|  |  |  |  | Glioblastoma (TS) |
|  |  |  |  | Breast Cancer (Onc) |
|  |  |  |  | Hepatocarcinoma (Onc) |
|  |  |  |  | AML (Onc) |
|  |  | FTO (E) | mRNA | Glioblastoma (Onc) |
|  |  |  |  | Cervix Cancer (Onc) |
|  |  |  |  | AML (Onc) |
|  |  |  |  | Melanoma (Onc) |
|  |  |  |  | Gastric Cancer (Onc) |
|  |  |  |  | Breast Cancer (Onc) |
|  |  | ALKBH5 (E) | mRNA | Pancreatic Cancer (TS) |
|  |  |  |  | AML (TS) |
|  |  |  |  | Glioblastoma (Onc) |
|  |  |  |  | Breast Cancer (Onc) |

TABLE 2-continued

RNA modifying proteins, RNA modifications produced thereby, and relation to cancer development

| Nt. | RNA Modification | RNA-modifying proteins | Site-specific position & RNA species | Associated Cancer |
|---|---|---|---|---|
| | | YTHDC2 (R) | mRNA | Colorectal Cancer (Onc) |
| | | YTHDF2 (R) | mRNA | Pancreatic Cancer (Dual Effect) Hepatocarcinoma (Onc) Prostate Cancer (Onc) |
| C | m3C | METTL6 (W) | C32 tRNA-Ser | Breast Cancer (Onc) Lung Cancer (Onc) |
| | | METTL8 (W) | mRNA | Hepatocarcinoma (TS) |
| | | ALKBH1 (E) | C32 tRNA | Hepatocarcinoma (Onc) |
| | | | C34 tRNA mitochondrial | Hepatocarcinoma (Onc) Cervix Cancer (Onc) |
| | | ALKBH3 (E) | C32, C47 tRNA | Cervix Cancer |
| C | m5C | NSUN1 (W) | C4447 rRNA-28S | Leukemia (Onc) |
| | | NSUN2 (W) | C34, C47, C48, C49, C50 tRNA | Ovarian Cancer (TS) |
| | | | mRNA | Skin Cancer (TS) Squamous-Cell Carcinoma (Onc) Breast Cancer (Onc) Bladder Cancer (Onc) |
| | | NSUN3 (W) | C34 tRNA mitochondrial | Non-Small Cell Lung Cancer |
| | | NSUN4 (W) | C841 rRNA-12S | Breast and Prostate Cancer |
| | | NSUN5 (W) | C3782 rRNA-28S | Glioblastoma (TS) |
| | | DNMT2 (W) | C38 tRNA-Asp | Colorectal Cancer (Onc) |
| C | ac4C | NAT10 (W) | C12 tRNA-Leu/Ser mRNA (ORF) C1337 rRNA-18S | Ovaric Cancer Hepatocarcinoma Colorectal Cancer (Onc) |
| G | m7Gpp(pN) | RNMT (W) | mRNA (5'Cap) | Breast Cancer (Onc) |
| | | NUDT16 (E) | mRNA (5'Cap) | T-ALL (TS) |
| G | m7G | METTL1 (W) | G46 tRNA miRNA | Hepatocarcinoma Lung Cancer (TS) |
| | | BUD23 (W) | G1639 rRNA-18S | Metastasis in p53+ tumours (Onc) |
| G | m2,2G | TRMT1 (W) | G26 tRNA | Breast Cancer |
| G | m2G | TRMT11 (W) | G6, G10, G26 tRNA | Prostate Cancer |
| G | Q | TGT (W) | G34 tRNA-Asn/Asp/His/Tyr | T-Cell Lymphoma (TS) Colon Cancer (Onc) |
| G | yW (and derivatives) | TYW2 (W) | G37 tRNA-Phe | Head and Neck (Onc) Breast Cancer (Onc) |
| U | m5U | TRMT2A (W) | U54 (tRNA) | Breast Cancer (TS) |
| U | ncm5U | ELP3 (W) | U34 tRNA-Lys/Gln/Glu | Breast Cancer (Onc) |
| U | mcm5U | ELP3 (W) ALKBH8 (W) | U34 tRNA-Lys/Gln/Glu | Breast Cancer (Onc) |
| U | mcm5s2U | CTU1 (W) | U34 tRNA-Lys/Gln/Glu | Breast Cancer (Onc) Melanoma (Onc) |
| | | CTU2 (W) | | Breast Cancer (Onc) Melanoma (Onc) |
| | | ELP3 (W) | | Breast Cancer (Onc) |
| | | ALKBH8 (W) | | Breast Cancer (Onc) |
| U | D | DUS2 (W) | U20 tRNA | Lung Cancer |
| U | Ψ | DKC1 (W) | rRNA (~36 sites in 18S, ~57 sites in 28S) | X-Linked Dyskeratosis congenita Prostate Cancer (Onc) Breast Cancer (Onc) Hepatocarcinoma (Onc) Lung Cancer (Onc) |
| Others | Nm | Fibrillarin (W) | rRNA (41 sites in 18S, 67 sites in 28S. U14 and G75 in 5.8S) | Breast Cancer (Onc) |
| | | HENMTI (W) | piRNA | Testicular tumours |

TABLE 2-continued

RNA modifying proteins, RNA modifications produced thereby, and relation to cancer development

| Nt. | RNA Modification | RNA-modifying proteins | Site-specific position & RNA species | Associated Cancer |
|---|---|---|---|---|
| Others | m(pN) | BCDIN3D (W) | miRNA (5'Cap) | Breast Cancer (Onc) |
| | | MePCE (W) | 7SK RNA | Breast Cancer (Onc) |
| Editing | A-to-I | ADAR1 (W) | mRNA | Hepatocarcinoma (Onc) |
| | | | | Colorectal Cancer (Onc) |
| | | | | Gastric Cancer (Onc) |
| | | | | Esophageal Cancer (Onc) |
| | | | | Glioblastoma (Onc) |
| | | | | Lung Cancer (Onc) |
| | | | miRNA | Leukemia (Onc) |
| | | ADAR2 (W) | mRNA | Gastric Cancer (Onc) |
| Editing | C-to-U | APOBEC1 (W) | mRNA | Hepatocarcinoma (Onc) |
| | | APOBEC3G (W) | mRNA | Hepatocarcinoma (Onc) |

Legend:
W: Writer,
E: Eraser,
R: Reader,
TS: Tumor suppressor,
Onc: Oncogene.
RNA modifications:
m1A: 1-methyladenosine,
ms2i6A: 2-methylthio-N6-isopentyl-adenosine,
i6A: N6-isopentenyladenosine,
m6A: N6-methyladenosine,
m3C: 3-methylcytosine,
m5C: 5-methylcytosine,
ac4C: N4-acetylcytosine,
m7Gpp(pN): 7-methylguanosine cap,
m7G: 7-methylguanosine internal,
m2,2G: N2,N2,-di-methylguanosine,
m2G: N2-methylguanosine,
Q: queuosine,
yW et al.: Wybutosine and derivatives,
m5U: 5-methyluridine,
ncm5U: 5-carbamoyl-methyluridine,
mcm5U: 5-methoxycarbonyl-methyluridine,
mcm5s2U: 5-methoxycarbonylmethyl-2-thiouridine,
D: dihydrouridine,
Ψ: pseudouridine,
Nm: 2'-O-Methylnucleotide,
m(pN): 5' phosphate monomethylation,
A-to-I: Deamination of Adenosine,
C-to-U: Deamination of Cytosine.
RNA modifying enzymes:
ADAR1-3: Adenosine Deaminase RNA Specific 1-3,
ALKBH1/3/5/8: AlkB Homolog 1/3/5/8,
APOBEC1/3G: Apolipoprotein B mRNA Editing Enzyme Catalytic Subunits 1/3G,
BCDIN3D: BCDIN3 Domain Containing RNA Methyltransferase,
BUD23: RRNA Methyltransferase And Ribosome Maturation Factor,
CDK5RAP1: CDK5 Regulatory Subunit Associated Protein 1,
CMTR1/2: Cap Methyltransferase 1/2,
CTU1/2: Cytosolic Thiouridylase Subunit 1/2,
DKC1: Dyskerin Psuedouridine Synthase 1,
DNMT2: tRNA Aspartic Acid Methyltransferase 1,
DUS2: Dihydrouridine Synthases 2,
ELP3: Elongator Acetyltransferase Complex Subunit 3,
FTO: FTO Alpha-Ketoglutarate Dependent Dioxygenase,
HENMT1: HEN Methyltransferase 1,
METTL1/2/3/6/8/14/16: Methyltransferase Like-1/2/3/6/8/16,
NAT10: N-Acetyltransferase 10,
NSUN1-5: NOP2/Sun RNA Methyltransferase 1-5,
NUDT16: Nudix Hydrolase 16,
RNMT: RNA Guanine-7 Methyltransferase,
TGT: Queuine TRNA-Ribosyltransferase Catalytic Subunit 1,
TRIT1: tRNA Isopentenyltransferase 1,
TRMT1/2A/2B1/5/6/10C/11/61A/61B/112: tRNA Methyltransferase Subunits,
TYW2: tRNA-YW Synthesizing Protein 2 Homolog.

In some embodiments, the binding domain comprises a reader protein. In some embodiments, the binding domain comprises a reader protein selected from NUDT16 and YTHDC2. NUDT is the U8 snoRNA-decapping enzyme (see, e.g., Uniprot Accession No. Q96DE0). YTHDC2 is the 3'-5' RNA helicase (see, e.g., Uniprot Accession No. Q9H6S0). In some embodiments, the binding domain comprises a fragment or derivative of NUDT16 or YTHDC2.

In some embodiments, the binding domain comprises a writer protein. In some embodiments, the binding domain comprises a writer protein selected from DNTM1, DNTM3A/B, NAT10, METTL3, METTL8, METTL15, TRM, BMT, DUS2, PUS, and NSUN2. DNMT1 and DNTM3A/B are DNA (cytosine-5)-methyltransferases. NAT10 is the RNA cytidine acetyltransferase (see, e.g., Uniprot Accession No. Q9H0A0). METTL3 is the N6-adenosine-methyltrasnferase catalytic subunit (see, e.g., Uniprot Accession No. Q86U44). NSUN2 is the RNA cytosine C(5)-methyltransferase (see, e.g., Uniprot Accession No. Q08J23). In some embodiments, the binding domain comprises a writer protein that is a fragment or derivative of NAT10, METTL3, or NSUN2.

In some embodiments, the binding domain comprises an eraser protein. In some embodiments, the binding domain comprises an engineered eraser protein selected from FTO, ALKBH3, and ALKBH5. FTO is the alpha-ketoglutarate-dependent dioxygenase (see, e.g., Uniprot Accession No. Q9C0B1). ALKBH3 is the alpha-ketoglutarate-dependent dioxygenase alkB homolog 3 (see, e.g., Uniprot Accession No. Q96Q83). ALKBH5 is the RNA demethylase (see, e.g., Uniprot Accession No. Q6P6C2). In some embodiments, the binding domain comprises a writer protein that is a fragment or derivative of FTO, ALKBH3, or ALKBH5.

Binding domains may be selected and/or engineered to bind to any non-canonical feature of a DNA or RNA. For example, the non-canonical feature may be a modified base, a DNA lesion, a modified backbone, or a structural element. In some embodiments, the binding domain may bind to two or more non-canonical features. In some embodiments, the binding domain binds a family of mutations with the same binding motif. For example, in some embodiments, the binding domain binds 5-methylcytidine (5mC) and its oxidation products 5-hydroxymethylcytidine (5hmC), 5-formylcytidine (5fC).

In some embodiments, the binding domain binds to a modified base and/or nucleoside. In some embodiments, the binding domain contacts at least one, at least two, or at least three modified nucleosides. In some embodiments, the binding domain contacts at least one modified nucleoside. In some embodiments, the binding domain contacts at least one modified nucleoside and one or more nucleotides adjacent thereto. Exemplary modified nucleosides that may occur in humans and other organisms are provided in Table 3A. Modified nucleosides that are known to occur in humans are listed in Table 3B. Additional modified bases and nucleosides are listed at the world wide web address gene s ilico.pl/modomics/modifications.

TABLE 3A

Modified nucleosides

| Modified nucleosides | Nucleic Acid in which it typically occurs* |
|---|---|
| 5-methyldeoxycytidine | DNA |
| 5-methylcytidine | RNA |
| 5-hydroxymethyldeoxycytidine | DNA |
| 5-hydroxymethylcytidine | RNA |
| 5-formydeoxycytidine | DNA |
| 5-formylcytidine | RNA |
| 1-methyladenosine | RNA |
| 6-methyladenosine | RNA, DNA |
| 6-methyldeoxy adenosine | RNA, DNA |
| 7-methylguanosine | RNA |
| 2,7,2'-methylguanosine | RNA |
| Pseudouridine | RNA |
| 1-methyl-3-(3-amino-3-carboxypropyl) pseudouridine | RNA |
| 1-methylpseudouridine | RNA |
| 2-thiouridine | RNA |
| 2'-O-methyluridine | RNA |
| 5-(carboxyhydroxymethyl) uridine methyl ester | RNA |
| 5-carbamoylmethyluridine | RNA |
| 5-carboxymethylaminomethyluridine | RNA |
| 5-methoxycarbonylmethyl-2-thiouridine | RNA |
| 5-methoxycarbonylmethyluridine | RNA |
| 5-methylaminomethyl-2-selenouridine | RNA |
| 5-methyluridine | RNA |
| 5-taurinomethyluridine | RNA |
| 2'-O-methylcytidine | RNA |
| 3-methylcytidine | RNA |
| N4-acetylcytidine | RNA |
| 1-methylguanosine | RNA |
| 2'-O-methylguanosine | RNA |
| 7-methylguanosine | RNA |
| N2,N2-dimethylguanosine | RNA |
| N2-methylguanosine | RNA |
| wybutosine | RNA |
| 2-methylthio-N6-isopentenyladenosine | RNA |
| 2-methylthio-N6-threonylcarbamoyladenosine | RNA |
| 2-O-methyladenosine | RNA |
| N6-formyladenosine | RNA |
| N6-isopentenyladenosine | RNA |
| inosine | RNA |

*As will be understood by those of skill in the art, a modified base/nucleoside that typically occurs in an RNA may sometimes occur in a DNA, and a modified base/nucleoside that typically occurs in a DNA may sometimes occur in an RNA.

TABLE 3B

Modified nucleosides occurring in humans

| Symbol | Modified Nucleoside | Symbol | Modified Nucleoside |
|---|---|---|---|
| Cm | 2'-O-methylcytidine | cmo$^5$U* | uridine 5-oxyacetic acid |
| m$^3$C | 3-methylcytidine | chm$^5$U | 5-carboxyhydroxymethyluridine |
| m$^4$C | N4-methylcytidine | mcm$^5$s$^2$U | 5-methoxycarbonylmethyl-2-thiouridine |
| m$^5$C | 5-methylcytidine | mcmo$^5$U* | uridine 5-oxyacetic acid methyl ester |

TABLE 3B-continued

Modified nucleosides occurring in humans

| Symbol | Modified Nucleoside | Symbol | Modified Nucleoside |
|---|---|---|---|
| m$^4$4C* | N4,N4-dimethylcytidine | mchm$^5$U | 5-(carboxyhydroxymethyl)uridine methyl ester |
| m$^5$Cm* | 5,2'-O-dimethylcytidine | cmnm$^5$Um* | 5-carboxymethylaminomethyl-2'-O-methyluridine |
| m$^4$4Cm* | N4,N4,2'-O-trimethylcytidine | acp$^3$U | 3-(3-amino-3-carboxypropyl)uridine |
| f5c | 5-formylcytidine | acp$^3$Um* | 3-(3-amino-3-carboxypropyl)methyluridine |
| f$^5$Cm | 5-formyl-2'-O-methylcytidine | Am | 2'-O-methyladenosine |
| hm$^5$C | 5-hydroxymethylcytidine | m$^1$A | 1-methyladenosine |
| ac$^4$C | N4-acetylcytidine | m$^2$A* | 2-methyladenosine |
| ac$^4$Cm* | N4-acetyl-2'-O-methylcytidine | m$^6$A | N6-methyladenosine |
| Y | Pseudouridine | m$^8$A | C8-methyladenosine |
| D | Dihydrouridine | m$^1$Am* | 1,2'-O-dimethyladenosine |
| Um | 2'-O-methyluridine | m$^6$Am | N6,2'-O-dimethyladenosine |
| m$^3$U | 3-methyluridine | m$^2$8A* | 2,8-dimethyladenosine |
| m$^5$U | 5-methyluridine | m$^6$2A | N6,N6-dimethyladenosine |
| Ym | 2'-O-methylpseudouridine | m$^6$6A | N6,N6-dimethyladenosine |
| m$^1$Y | 1-methylpseudouridine | m$^6$6Am* | N6,N6,2'-O-trimethyladenosine |
| m$^3$Y* | 3-methylpseudouridine | hn$^6$A* | N6-hydroxynorvalylcarbamoyladenosine |
| m$^5$D* | 5-methyldihydrouridine | i$^6$A | N6-isopentenyladenosine |
| m$^3$Um* | 3,2'-O-dimethyluridine | I | Inosine |
| m$^5$Um* | 5,2'-O-dimethyluridine | Im | 2'-O-methylinosine |
| s$^2$Um | 2-thio-2'-O-methyluridine | m$^1$I | 1-methylinosine |
| m$^5$s$^2$U | 5-methyl-2-thiouridine | Gm | 2'-O-methylguanosine |
| nm$^5$U* | 5-methylaminouridine | m$^1$G | 1-methylguanosine |
| mnm$^5$U* | 5-methylaminomethyluridine | m$^2$G | N2-methylguanosine |
| f$^5$U | 5-formyl-uridine | m$^7$G | 7-methylguanosine |
| f5Um* | 5-formyl-O-methyluridine | m$^1$Gm* | 1,2'-O-dimethylguanosine |
| ho$^5$U | 5-hydroxyuridine | m$^2$Gm* | N2,2-O-dimethylguanosine |
| ncm$^5$U | 5-carbamoylmethyluridine | m$^2$2G | N2,N2-dimethylguanosine |
| ncm5Um* | 5-carbamoylmethyl-2'-O-methyluridine | m$^2$7G | N2,7-dimethylguanosine |
| mcm$^5$U | 5-methoxycarbonylmethyluridine | PreQ1* | 7-aminomethyl-7-deazaguanosine |
| mo$^5$U | 5-methoxyuridine | m$^2$2Gm* | N2,N2,2-O-trimethylguansine |

In some embodiments, the binding domain binds to one or more of the following modified nucleosides: 3-methylcytidine (m3C), 5-methylcytidine (m5C), N$^4$-acetylcytidine (ac4C), Pseudouridine (Ψ), 1-methyladeno sine (m1A), N$^6$-methyladenosine (m6A), Inosine (I), 7-methylguanosine (m7G), Dihydrouridine (D), 3-methyluridine (m3U), 5-methyluridine (m5U), 1-methylguanosine (m1G), N$^2$-methylguanosine (m2G), 5-methyldeoxycytidine (m5dC), N$^4$-methyldeoxycytidine, 5-hydroxymethylcytidine (5-hmC), 5-hydroxymethyldeoxycytidine (5hmdC), 5-carboxydeoxycytidine (5cadC), 5-formylcytidine (5fC), 5-formyldeoxycytidine (5fdC), 6-methyldeoxyadeno sine, N$^7$-methylguanosine (m7G), 2,7,2'-methylguano sine, or ribose methylation (Nm).

In some embodiments, the non-canonical feature is: 3-methylcytidine (m3C), 5-methylcytidine (m5C), N$^4$-acetylcytidine (ac4C), Pseudouridine (Ψ), 1-methyladenosine (m1A), N$^6$-methyladenosine (m6A), Inosine (I), 7-methylguanosine (m7G), Dihydrouridine (D), 3-methyluridine (m3U), 5-methyluridine (m5U), 1-methylguanosine (m1G), N$^2$-methylguanosine (m2G), 5-methyldeoxycytidine (m5dC), N$^4$-methyldeoxycytidine, 5-hydroxymethylcytidine (5-hmC), 5-hydroxymethyldeoxycytidine (5hmdC), 5-carboxydeoxycytidine (5cadC), 5-formylcytidine (5fC), 5-formyldeoxycytidine (5fdC), 6-methyldeoxyadenosine, N$^7$-methylguanosine (m7G), 2,7,2'-methylguanosine, or ribose methylation (Nm).

In some embodiments, the binding domain binds to a nucleic acid lesion resulting from naturally occurring oxidative or ultra-violet light-induced damage, or bulky adduct formation or base alkylation by exogenous agents. In some embodiments, the nucleic acid lesion is the lesion is 8-oxo-guanine (8-oxoG), one or more abasic sites, cis-platin crosslinks, benzo(a)pyrene diol epoxide (BPDE)-adducts, cyclobutene pyrimidine dimers (CPD), pyrimidine-pyrimidone (6-4) photoproduct (6-4PP), 6-O-methylguanine (O$^6$-MedG), or O6-(Carboxymethyl)-2'-deoxyguanosine (O6-CMdG). In some embodiments, the non-canonical feature is a nucleic acid lesion resulting from naturally occurring oxidative or ultra-violet light-induced damage, or bulky adduct formation or base alkylation by exogenous agents. In some embodiments, the nucleic acid lesion is the lesion is 8-oxo-guanine (8-oxoG), one or more abasic sites, cis-platin crosslinks, benzo(a)pyrene diol epoxide (BPDE)-adducts, cyclobutene pyrimidine dimers (CPD), pyrimidine-pyrimidone (6-4) photoproduct (6-4PP), 6-O-methylguanine (O$^6$-MedG), or O6-(Carboxymethyl)-2'-deoxyguanosine (O6-CMdG).

In some embodiments, the binding domain binds to a structural element. The structural element may be, for example, a hairpin or a loop. Other illustrative structural elements include, but are not limited to, Z-DNA structures, G-quadruplexes, triplexes, i-motifs, bulges, triplexes, three-way junctions, cruciform structures, tetraloops, ribose zippers, pseudoknots, etc.

Nucleic Acid-Binding Molecules and Methods for Making the Same

Figure 1B:
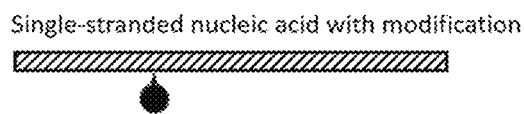
Figure 1C:
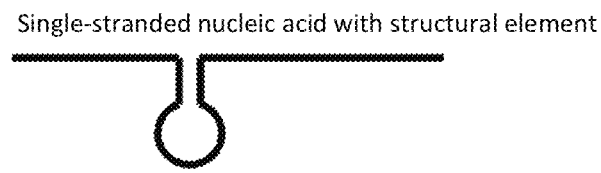
Figure 1D:
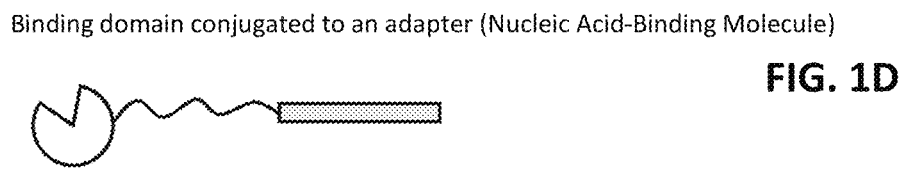

Provided herein are nucleic acid-binding molecules comprising a binding domain and an adapter. An exemplary structure for a nucleic acid-binding molecule as described herein is shown in FIG. 1D. The binding domain binds specifically to a non-canonical feature of a DNA or an RNA. The adapter comprises a nucleic acid barcode sequence unique to the non-canonical feature bound specifically by the binding domain.

In some embodiments, a nucleic acid-binding molecule described herein may further comprise one or more additional features. For example, in some embodiments, a nucleic acid-binding molecule that comprises a binding domain and an adapter, may further comprise an enzyme or a catalytic fragment thereof. In some embodiments, a nucleic acid-binding molecule that comprises a binding domain and an adapter, may further comprise an enzyme (or a fragment thereof) that lacks catalytic activity. In some embodiments, the enzyme is a DNA N-glycosylase or RNA N-glycosylase, or a catalytic fragment or variant thereof. These enzymes create abasic sites that can stall reverse transcription.

In some embodiments, a nucleic acid-binding molecule may comprise a base editing enzyme. In some embodiments, the enzyme is a DNA methylase, an RNA methylase, or a pseudouridine synthase. The base editing enzyme may be, for example, a cytidine deaminase of the APOBEC family, an adenosine deaminase of the ADAR family, or a catalytic fragment or variant thereof. In some embodiments, the base editing enzyme is APOBEC1. In some embodiments, the based editing enzyme is APOBEC3A. In some embodiments, the cytidine deaminase comprises a maltose binding domain to enhance deaminase solubility. In some embodiments, the cytidine deaminase comprises a Spycatcher peptide to enhance deaminase solubility. In some embodiments, the cytidine deaminase comprises a maltose binding domain and a Spycatcher peptide to enhance deaminase solubility. In some embodiments, a nucleic acid-binding molecule may comprise a transposase. The transposase may be, for example, a DDE transposase, a tyrosine (Y) transposase, a serine (S) transposase, a Y2 transposase or a Y1 transposase. In some embodiments, the transposase is the Tn5 transposase, or a fragment or derivative thereof. In some embodiments, the transposase is the Sleeping Beauty transposase, or a fragment or derivative thereof. In some embodiments, a nucleic acid-binding molecule may comprise an integrase, such as an HIV integrase.

The nucleic acid-binding molecules described herein may specifically bind RNAs or may specifically bind DNAs. In some embodiments, the nucleic acid-binding molecules may bind to both RNAs and DNAs. In some embodiments, the nucleic acid-binding molecules may specifically bind to a double stranded nucleic acid with one or more non-canonical features, such as a modified nucleoside as shown in FIG. 1A. In some embodiments, the nucleic acid-binding molecules may specifically bind to a single stranded nucleic acid with one or more non-canonical features, such as a modified nucleoside as shown in FIG. 1B or a structural feature as shown in FIG. 1C.

Figure 1E:
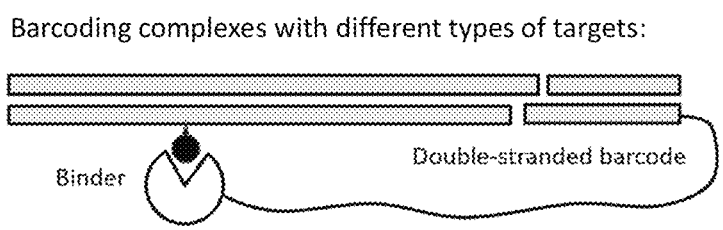
FIGS. 1E-1G are schematics showing complexes comprising different nucleic acid-binding molecules as described herein bound to target nucleic acids.
Figure 1F:
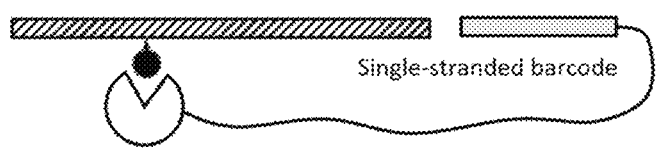
Figure 1G:
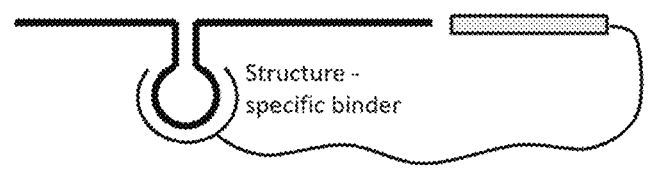

In some embodiments, binding of a nucleic acid-binding molecule to a non-canonical feature of a target nucleic acid positions the DNA adapter in proximity to the 5' or 3' terminus of the target nucleic acid. For example, FIG. 1E depicts binding of a nucleic acid-binding molecule to a modified nucleoside on a double-stranded target nucleic acid, which positions a double-stranded barcode in proximity to the 3' end of the target nucleic acid. FIG. 1F depicts binding of a nucleic acid-binding molecule to a modified nucleoside on a single-stranded target nucleic acid, which positions a single-stranded barcode in proximity to the 3' end of the target nucleic acid. FIG. 1G depicts binding of a nucleic acid-binding molecule to a structural feature of a target nucleic acid, positioning a barcode in proximity to the 3' end thereof.

Nucleic acid-binding molecules may be made using standard molecular biology and/or chemistry techniques. For example, in some embodiments, the binding domain is coupled to the adapter, to form a binding domain-adapter conjugate. In some embodiments, the DNA adapter comprises a linker, and the binding domain is coupled to the adapter via the linker. The coupling step may be, in some embodiments, covalent or non-covalent.

Adapters (e.g., adapters comprising a linker) may be coupled to binding domains using several different methods. In some embodiments, adapters may be covalently coupled to binding domains by random tagging. For example, a NHS-activated residue on the adapter may be reacted with one or more amine groups of surface exposed protein lysine residues of the binding domain. Similarly, maleimide-activated adapters can be reacted with native or engineered cysteines of the binding domain. As will be understood by those of skill in the art, the number of adapters tethered to a binding domain will depend on the number of reactive lysine or cysteine residues, respectively, and the choice of reaction conditions.

Site-selective coupling methods can also be used. Site-specific coupling avoids impacting the function of the binding domain and allows for reproducible material production. Site-selective internal tagging of a binding domain can be achieved by genetic incorporation of unnatural amino acid using cell lines with engineered aminoacyl-tRNA synthetase/tRNA pairs. The incorporated unnatural amino acids exhibit moieties that can undergo bio-orthogonal reactions. Commonly used are amino acids that bear moieties that can undergo copper-catalyzed azide alkyne cycloadditions (CuAAC), photoactivated 1,3-dipolar cycloadditions, strain-promoted azide alkyne cycloadditions (SPAAC) or inverse electron-demand Diels-Alder cycloadditions (IEDDA). An illustrative, versatile method for C- or N-terminal tagging of binding domains involves the use of protein or peptide-tags. Protein-tags such as SNAP-tag, Halo-tag, Spy-tag, Snoop-tag, Isopeptag, Dog-tag, Sdy-tag, Clip-tag are small proteins or peptides that can be cloned into any gene expressing a binding domain, to express the binding domain as protein-tag fusion protein. Such protein-tags may self-catalyze covalent bond formation with a specific peptide or substrate. For example, SpyCatcher is a 113-residue protein that recognizes SpyTag, a 13-residue peptide that can be readily conjugated to any DNA sequence. In some embodiments, SpyCatcher comprises SEQ ID NO: 12. In some embodiments, the SpyTag comprises SEQ ID NO: 10. Depending on the molecular weight of the binding domain, a smaller peptide-tag may be preferred. Peptide-tags are typically 10-12 amino acids long and act in enzyme-mediated coupling reactions. In some embodiments, a peptide for tag to the C-terminus comprises SEQ ID NO: 11 (LCxPxR wherein x is any amino acid). Examples of enzyme-mediated reactions for coupling a binding domain to an adapter include but are not limited to: (a) the use of biotin-ligase to link AP-peptide labeled binding and biotin-DNA (e.g., biotin-linkers), (b) the use of lipoic acid ligase to link LAP-peptide labeled binding domains and lipoic acid-DNA (e.g., lipoic acid-linkers), (c) the use of tubulin tyrosine ligase to link Tub-tag labeled binding domains and tyrosine-modified DNA (e.g., tyrosine-modified linkers), (d) the use of Sortase-A, which reacts with LPxTG peptide and glycine-modified DNA (e.g., glycine-modified linkers), and more. In addition, a group of metal ion recognition tags and small molecule binding motifs may be used. Another variant of peptide tagging is to redirect the endogenous cellular machinery to introduce aldehydes into recombinant proteins. The method exploits formylglycine-generating enzyme (FGE), which converts cysteine co-translationally to formylglycine (FGly) within a conserved 13-residue consensus sequence. The resulting aldehyde tag can be readily modified with reactive amines that are tethered to DNA.

In some embodiments, the adapter may be coupled to the binding domain via bioorthogonal chemistry. In some embodiments, the binding domain comprises a DNA oligonucleotide which facilitates coupling of the barcode. DNA oligonucleotides are readily commercially available with amino, azido, biotin and alkyne modification. Alkyne and azido oligos can be coupled to unnatural amino acids in a copper-catalyzed azide-alkyne cycloaddition or a strain-promoted azide-alkyne cycloaddition. Amino-oligonucleotide may be reacted with formylglycine, which can be introduced into the binding domain by the formylglycine-generating enzyme (FGE) within a 13aa conserved sequence.

Once the nucleic acid-binding molecules described herein bind to a target nucleic acid, a complex is formed. In some embodiments, the nucleic acid-binding molecule of the complex may be covalently linked to the target nucleic acid. For example, the nucleic acid-binding molecule may be chemically and/or photochemically linked to the target nucleic acid.

Adapter/Barcode Transfer Reactions

The nucleic acid-binding molecules described herein may be used to transfer an adapter to a target nucleic acid, such as an adapter comprising a barcode. Thus, in some embodiments, the nucleic acid-binding molecules described herein may be used to transfer a barcode to a target nucleic acid. The barcode may be a MBC, i.e., a barcode that is unique to the non-canonical feature bound specifically by the binding domain of the nucleic acid-binding molecule. A target nucleic acid to which an adapter has been transferred is referred to herein as a "labeled target nucleic acid," a "labeled target" or similar terms. A target nucleic acid to which a barcode has been transferred is referred to herein as a "barcoded target nucleic acid," a "barcoded target" or similar terms. A reaction in which an adapter is transferred to a target nucleic acid is referred to herein as an "adapter transfer reaction." Similarly, a reaction in which a barcode is transferred to a target nucleic acid is referred to herein as a "barcode transfer reaction."

The goal of adapter/barcode transfer is covalent attachment of the adapter/barcode to a target nucleic acid molecule. For example, in some embodiments, a barcode is transferred to the target nucleic acid by covalently coupling the barcode to the 5' or 3' end of the target nucleic acid. In some embodiments, a barcode is transferred to the target nucleic acid by covalently coupling the barcode or its complement to the 5' or 3' end of the target nucleic acid. The labeled/barcoded nucleic acid molecule may, in some embodiments, be sequenced in downstream steps. In some embodiments, a copy of the labeled target nucleic acid may be sequenced. FIG. 3A-3E provide examples of adapter/barcode transfer reactions.

Figure 3A:
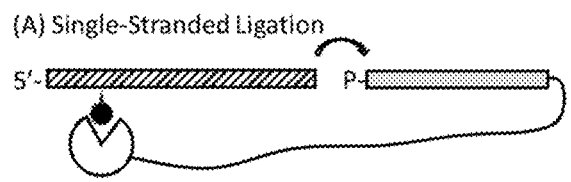
FIGS. 3A-3E are schematics showing different adapter transfer schemes, including single-stranded ligation (FIG. 3A), splint ligation (FIG. 3B), primer or splint extension (FIG. 3C), templated extension (FIG. 3D), and double-stranded ligation (FIG. 3E).
Figure 3B:
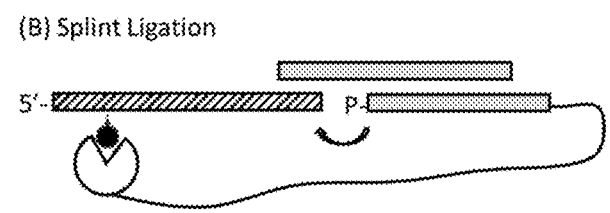

The enzymes used for adapter transfer differ for DNA and RNA target nucleic acids and depend on the adapter architecture. Adapter/barcode transfer to a target DNA may be performed using one or more enzymes, such as T4 DNA ligase, CircLigase, Klenow fragment, or Bsu DNA polymerase. Adapter/barcode transfer to a target RNA may be performed using, for example T4 RNA ligase, T4 RNA ligase 2, or RtcB ligase. For example, FIG. 3A illustrates ligation of a single-stranded DNA adapter (e.g., an adapter comprising or consisting of a barcode) to single-stranded target nucleic acid. In some embodiments wherein the target nucleic acid is an RNA, the adapter comprises a 5' phosphate, and is catalyzed by T4 RNA ligase. Alternatively, the adapter may be 5'-pre-adenylated and transferred by T4 RNA ligase 2 to obviate the need for ATP and limit the reaction to a single turnover. Alternatively, an unphosphorylated adapter may be used, and may be transferred to 3'-phosphorylated RNA using RtcB ligase. In some embodiments wherein the target nucleic acid is a DNA, the adapter/barcode may be transferred in a reaction catalyzed by CircLigase.

Splint ligation may also be used to transfer an adapter/barcode to a target nucleic acid. In splint ligation, a bridging DNA or RNA oligonucleotide is used to bring two nucleic acids together, which may be joined by one or more enzymes. For example, splint ligation of two RNAs (e.g., a target RNA and an adapter/barcode) may be carried out using T4 ligase, and a bridging RNA oligonucleotide complementary to the RNAs. For example, the splinted nucleic acid construct shown in FIG. 3B may be created by using splint ligation. SplintR ligase may be used to connect the 3' end of RNA to 5'-pDNA when annealed to either DNA or RNA complements. If the target molecule is DNA, splinted DNA ligation may be performed using enzymes like T4 DNA ligase, T3 DNA ligase, T7 DNA ligase or *E. coli* DNA ligase.

Figure 3C:
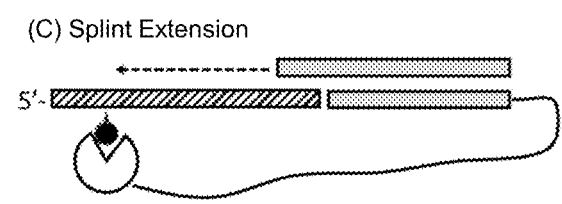

Splint extension and primer extension are other methods that may be used to transfer an adapter/barcode to a target nucleic acid. A "splint" is a sequence that spans a ligation junction. When a primer is used, it typically does not span the ligation junction FIG. 3C depicts adapter transfer by splint extension, wherein a copy of the sequence of the target nucleic acid molecule is made, using the adapter sequence as a splint. If the target nucleic acid molecule is RNA, this reaction may be catalyzed by a reverse transcriptase such as Avian Myeloblastosis Virus (AMV) Reverse Transcriptase and Moloney Murine Leukemia Virus (M-MuLV, MMLV), as well as a fully or partially matched 3' end of the DNA adapter. Thus, the 3' end of the splint may contain random bases or synthetic universal bases that base pair promiscuously. If the target molecule is DNA, the primer may be extended by any suitable DNA polymerase with or without 3'→5' exonuclease activity.

Figure 3D:
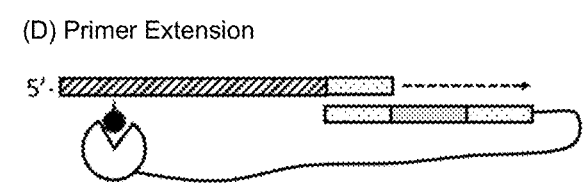

In some embodiments, templated extension may be used to transfer an adapter/barcode to a target nucleic acid. FIG. 3D illustrates direct adapter transfer by primer extension, wherein the adapter is copied by a polymerase into the target nucleic acid using the bound copy of the adapter as a template. In some embodiments, the polymerase works at temperatures that enable short spacer sequences and is devoid of 3' to 5' exonuclease and 3' tailing activity. For DNA adapters/barcodes, this reaction may be catalyzed by a DNA polymerase, e.g. Klenow fragment, T7, T4 or Bsu DNA polymerase. FIG. 3D can be executed as part of a multi-cycle encoding process, or as a single cycle. In some embodiments, the barcoded nucleic acid produced is capped with a universal primer as a last step. The universal primer serves as the starting site for reverse transcription. In some embodiments, a reverse transcription primer comprises SEQ ID NO: 8.

Figure 3E:
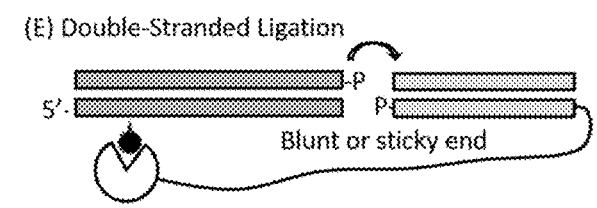

Additionally, double-stranded ligation may also be used to transfer an adapter/barcode to a target nucleic acid. For example, FIG. 3E illustrates double-stranded ligation for adapter/barcode transfer. In some embodiments, the target nucleic acid molecule may be double-stranded DNA, or an RNA/DNA hybrid, and may have either a blunt or a sticky end. Blunt and sticky end ligation of double-stranded DNA may be catalyzed by T4, T3, T7 or *E. coli* ligase.

In some embodiments, chemical ligation may be used to transfer an adapter/barcode to a target nucleic acid.

Methods for Facilitating Intra-Complex Adapter/Barcode Transfer by Spatial Separation Intra-complex adapter/barcode transfer may be facilitated by spatial separation of the molecules involved in the reaction. Specifically, the transfer may be facilitated by separating the nucleic acid-binding molecules, the target nucleic acids, and/or complexes comprising the nucleic acid-binding molecules bound to target nucleic acids, such that a nucleic acid-binding molecule can only interact with the target nucleic acid to which it is bound.

Barcode transfer may be performed in several different environments that allow for spatial separation. Spatial separation can be achieved, for example, by high dilution of the complexes comprising nucleic acid-binding molecules bound to target nucleic acids in solution. The solution must be dilute enough to allow for spatial separation of any complexes comprising nucleic acid-binding molecules bound to target nucleic acids present therein. Such spatial separation promotes intra-complex barcode transfer, and substantially prevents barcode transfer between nucleic acid-binding molecule complexes. In some embodiments, the concentration of the complexes in the dilute solution is less than 10 nM, less than 1 nM, less than 0.1 nM, less than 0.01 nM, or less than 0.001 nM.

Figure 5A:
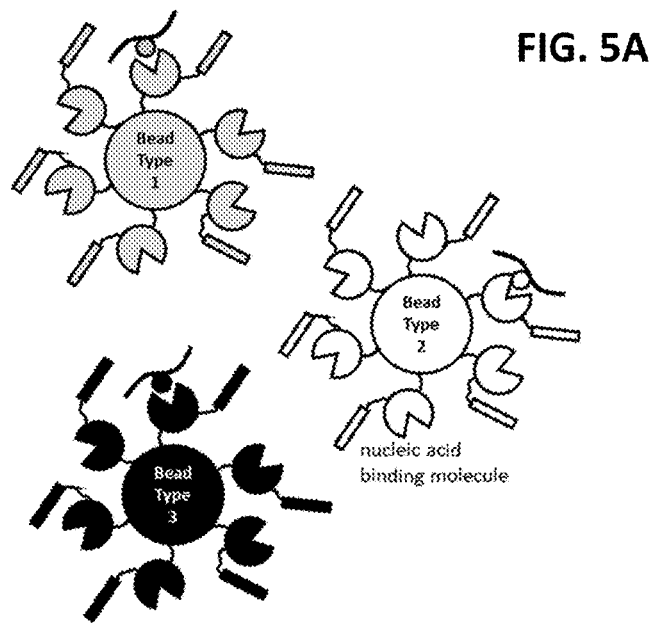
FIGS. 5A-5C are schematics showing different formats for intra-complex adapter transfer on beads and the composition of the associated bead pools. A bead may be decorated with a single type of nucleic acid binding molecule (FIG. 5A), or with multiple types of nucleic acid binding molecules (FIG. 5B). Alternatively, a bead may display oligonucleotides for the capturing of RNA molecules by hybridization (FIG. 5C).
Figure 5B:
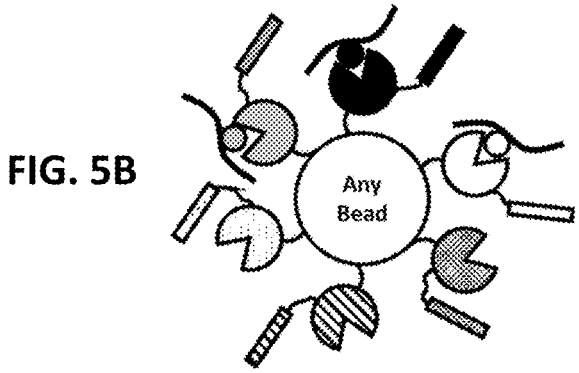

In some embodiments, spatial separation can be achieved by surface immobilization. For example, the nucleic acid-binding molecules described herein may be immobilized by being coupled to a substrate. Each substrate may comprise only one type of nucleic acid-binding molecule (FIG. 5A), or may comprise at least two, at least three, at least four, at least five, or more types of nucleic acid-binding molecules (FIG. 5B). Each "type" of nucleic acid-binding molecule binds to a different non-canonical feature and/or comprises a different barcode. In some embodiments, a first nucleic acid-binding molecule is spatially separated from a second nucleic acid-binding molecule on a surface of the substrate. Surface binding capacity and format may be tailored to enable absolute or relative quantification of target molecules and modifications.

Exemplary substrates to which the nucleic acid-binding molecules may be coupled include, for example, beads, chips, plates, slides, dishes, or 3-dimensional matrices. In some embodiments, the substrate is a resin, a membrane, a fiber, or a polymer. In some embodiments, the substrate is a bead, such as a bead comprising sepharose, agarose, cellulose, polystyrene, polymethacrylate, and/or polyacrylamide. In some embodiments, the substrate is a magnetic bead. In some embodiments, the support is a polymer, such as a synthetic polymer. A non-limiting list of synthetic polymers includes: polystyrene, poly(ethylene)glycol, polyisocyanopeptide polymers, polylactic-co-glycolic acid, poly(ε-caprolactone) (PCL), polylactic acid, poly(3-hydroxybutyrate-co-3-hydroxyvalerate) (PHBV), chitosan and cellulose.

The nucleic acid-binding molecules may be coupled directly to the surface of substrate. For example, molecules may be coupled directly to the substrate by one or more covalent or non-covalent bonds. In embodiments wherein the substrate is a 3D matrix or other 3D structure, the nucleic acid-binding molecules may be coupled to multiple surfaces of the substrate.

Figure 5C:
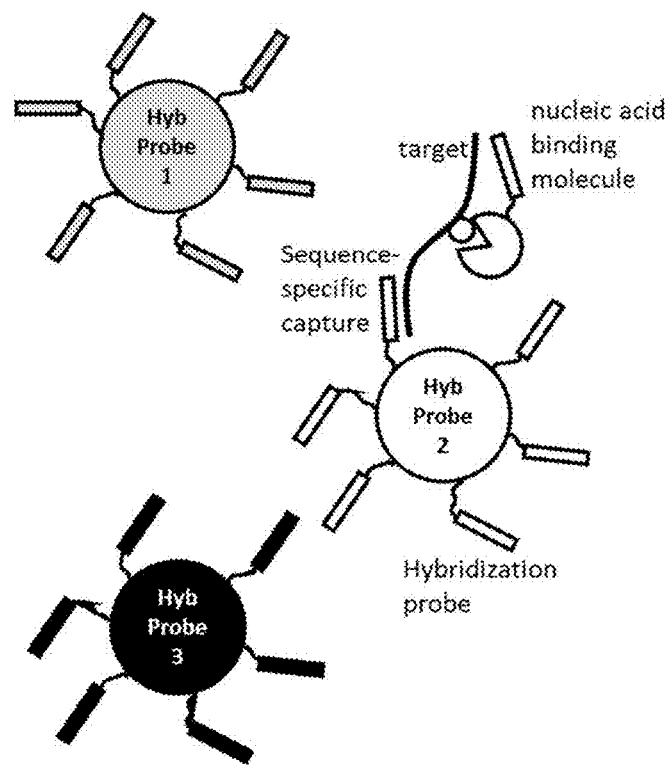

In some embodiments, the nucleic acid-binding molecules may be coupled indirectly to the surface of the substrate. For example, the nucleic acid-binding molecule may be coupled to the surface of the substrate indirectly via a capture molecule, wherein the capture molecule is coupled directly to the substrate. The capture molecule may be any nucleic acid, protein, sugar, chemical linker, etc., that can bind or be linked to both the substrate and the nucleic acid-binding molecule and/or the target nucleic acid. In some embodiments, a capture molecule binds to a nucleic acid-binding molecule. In some embodiments, a capture molecule binds to a binding domain or to an adapter (e.g., to the linker of an adapter) of the nucleic acid-binding molecule. In some embodiments, a capture molecule binds to a target nucleic acid. In some embodiments, a capture molecule binds to a sequence or a structural feature of a target nucleic acid (FIG. 5C). For example, in some embodiments, a capture molecule may bind to a polyA tail of the target nucleic acid or to a specific DNA or RNA sequence.

In some embodiments, the target nucleic acid may be coupled directly to the surface of the substrate via a reactive chemical group. For example, the nucleic acid target may be modified with azido groups that undergo Cu-catalyzed click chemistry with alkyne decorated beads. Other examples: trans-cyclooctene (TCO)/methyl-tetrazine, DBCO/azido.

In some embodiments, a first nucleic acid-binding molecule is separated from a second nucleic acid-binding molecule on the surface of a substrate, so as to ensure that each nucleic acid-binding molecule can only interact with one target nucleic acid. In some embodiments, a first nucleic acid-binding molecule is separated from a second nucleic acid-binding molecule by at least 50 nm. For example the first and second nucleic acid-binding molecules may be separated by about 50 nm to about 500 nm, such as about 50 nm to about 100 nm, about 100 nm to about 150 nm, about 150 nm to about 200 nm, about 200 nm to about 250 nm, about 250 nm to about 300 nm, about 300 nm to about 350 nm, about 350 nm to about 400 nm, about 400 nm to about 450 nm, or about 450 nm to about 500 nm. In some embodiments, the first and second nucleic acid-binding molecules may be separated by more than about 500 nm.

In general, the goal of coupling a nucleic acid-binding molecule (or the target nucleic acid) to a substrate is to ensure intra-complex transfer of an adapter and/or a barcode. Substrates comprising two or more spatially-separated nucleic acid-binding molecules may be produced using methods known to those of skill in the art. FIG. 4A-4D provides non-limiting examples of ways that a nucleic acid-binding molecule or a target nucleic acid may be coupled to, and immobilized on, a substrate. These examples are described in more detail below. FIG. 5A-5C illustrate non-limiting examples of ways that nucleic acid-binding molecules or target nucleic acid may be immobilized on beads.

Coupling of a Nucleic Acid-Binding Molecule to a Substrate

Figure 4A:
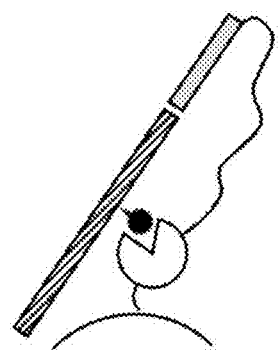
FIGS. 4A-4D are schematics showing different formats for intra-complex adapter transfer, including surface-immobilization of recognition elements (FIG. 4A), RNA capture via a poly-A tail (FIG. 4B), DNA or RNA capture via a hybridization probe (FIG. 4C), and direct surface tethering of nucleic acid targets (FIG. 4D).

FIG. 4A shows a nucleic acid-binding molecule coupled either directly or indirectly to a substrate. In some embodiments, a plurality of nucleic acid-binding molecules may be immobilized on a substrate using site-specific chemistry. For example, in some embodiments, the binding domain of a nucleic acid-binding molecule may comprise a site that allows it to be immobilized on a substrate, and a site for tethering the DNA adapter. Conjugation of a binding domain to the surface of a substrate may be facilitated by fusing self-catalyzing protein tags to the terminus of the binding domain (e.g., Spycatcher, sortase A, SNAP tag, Halo tag and CLIP tag). These protein tags on the binding domain may then be covalently reacted with their cognate reactive moieties on the surface of the substrate. For example, the Spycatcher protein may be engineered into a binding domain. Spytag forms a covalent linkage with a Spytag protein (a 13aa peptide). If Spytag is coupled to the surface of a substrate, a reaction between a Spycatcher-linked binding domain and Spytag will serve to covalently link the binding domain to the substrate. Similarly, a binding domain may be fused with a Sortase A tag, which could be used to react with pentaglycine coupled to a substrate surface. As another example, a binding domain may be fused with a SNAP tag, which could be used to react with O6-benzylguanine that is coupled to a substrate surface. In some embodiments, a binding domain may be fused with a CLIP tag, which could be used to react with O2-benzylcytosine that is coupled to a substrate surface. In some embodiments, a binding domain may be fused with a Halo tag, which could be used to react with an alkyl halide present on a substrate surface.

In some embodiments, the binding molecule may comprise a biotin moiety. Such binding molecules may be immobilized on a substrate surface by a capture molecule that binds biotin (e.g., streptavidin).

Figure 17A:
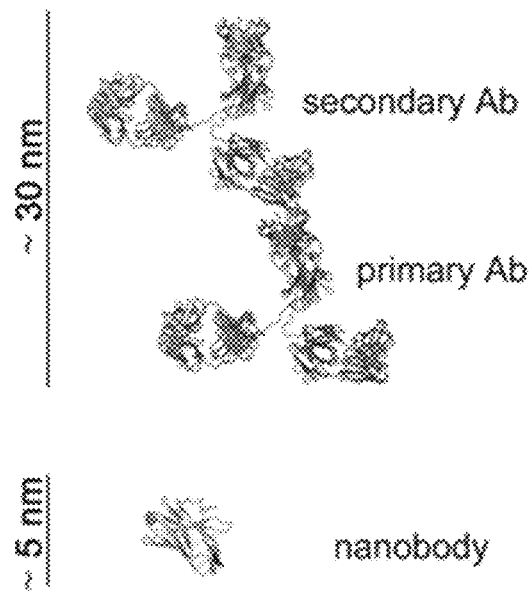
FIG. 17A is a schematic comparing the size of a nanobody to the size of a primary antibody bound to a secondary antibody.
Figure 17B:
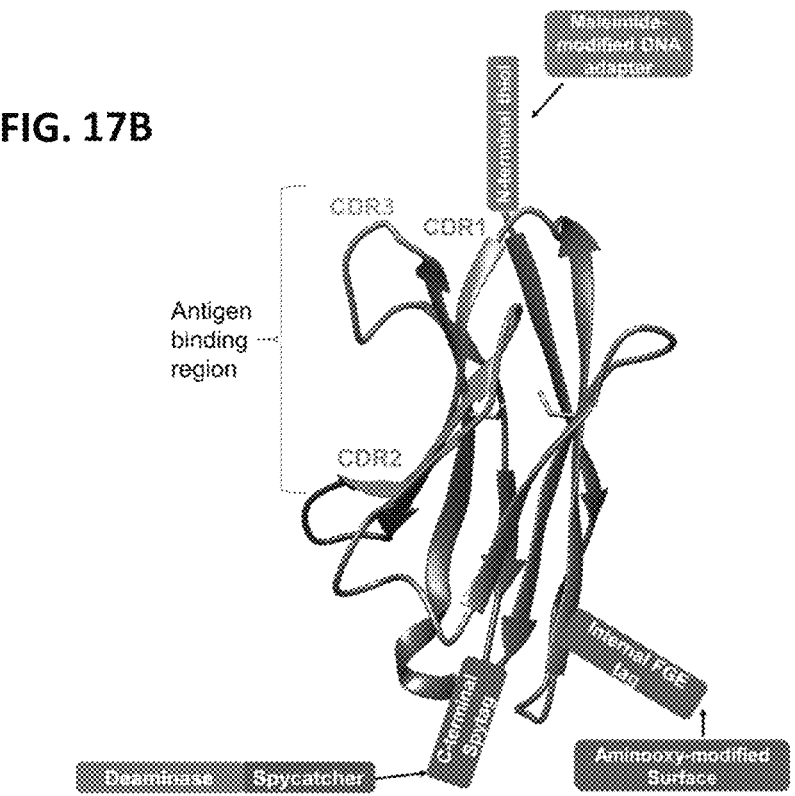
FIG. 17B shows the three-dimensional structure of a nanobody. Illustrative coupling sites for the DNA adapter, deaminase and the surface are indicated in the drawing.
Figure 17C:
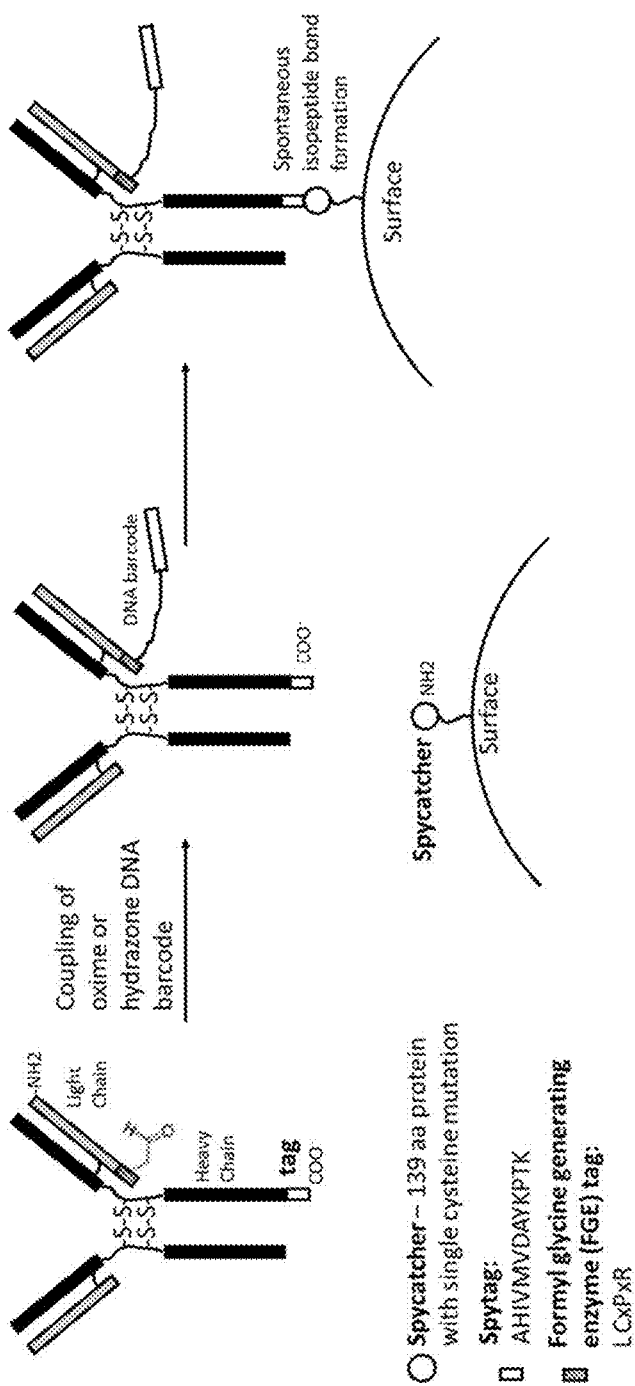
FIG. 17C shows an illustrative method for site-specific coupling of an adapter (i.e., DNA barcode labeling) and immobilization of an antibody on a substrate surface.

FIG. 17A-B illustrates nanobody size (FIG. 17A) and molecular structure (FIG. 17B), including the three complementarity determining regions (CDRs). FIG. 17B shows a DNA adapter that is site-specifically conjugated to the N-terminus via thiol-maleimide chemistry. A deaminase Spycatcher fusion protein is site-specifically tethered to a C-terminal SpyTag peptide. Surface immobilization of the nucleic acid-binding molecule is accomplished via a reaction between an aminooxy-functionalized surface and internal 13aa peptide that is converted co-translationally to formylglycine by formylglycine-generating enzyme (FGE). FIG. 17C shows an example of (i) barcode labeling of a binding domain comprising an antibody to form a nucleic acid-binding molecule, and (ii) site-specific immobilization of the nucleic acid-binding molecule on the surface of a substrate. In this example, the DNA barcode is site-specifically conjugated to the C-terminal domain of the antibody light chain via an internal 13 amino acid peptide that is converted co-translationally to formylglycine by formylglycine-generating enzyme (FGE), in order to form a nucleic acid-binding molecule. Surface immobilization of the nucleic acid-binding molecule is accomplished via a reaction between Spytag and Spycatcher. Spytag is a short 13aa peptide that is engineered onto the C-terminus of the antibody heavy chain. The substrate surface displays Spycatcher protein at appropriate density. The C-terminus of Spytag and the N-terminus of Spycatcher react spontaneously and form an isopeptide bond.

Coupling a Target Nucleic Acid to a Substrate

Figure 4B:
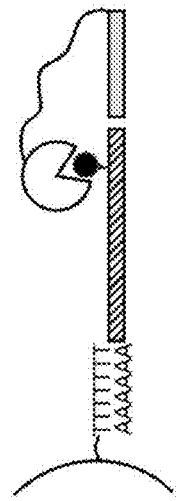
Figure 4C:
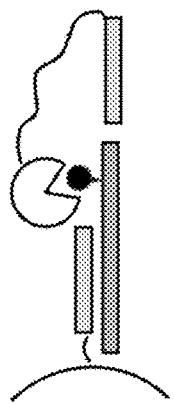
Figure 4D:
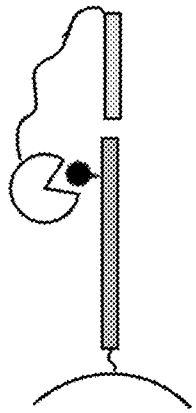

FIG. 4B shows a nucleic acid-binding molecule coupled indirectly to a substrate via a capture molecule. In this example, the capture molecule comprises a nucleic acid sequence that binds to the polyA tail of a target nucleic acid, however any other unique base sequence on the target nucleic acid may be used. FIG. 4C shows a target nucleic acid coupled indirectly to a substrate via a capture molecule, wherein the capture molecule is a hybridization probe that binds to the target nucleic acid (i.e., it is specific for the primary sequence, or a secondary structure of the target nucleic acid). FIG. 4D shows a target nucleic acid coupled directly to a substrate via covalent tethering.

Thus, in some embodiments a substrate may be decorated with oligonucleotide capture molecules that hybridize to a feature of a target nucleic acid. For example, mRNA may be captured by hybridization to a capture molecule that comprise poly-dT oligonucleotides or gene-specific sequences. In some embodiments, the capture molecules are present at a low surface density to physically isolate the nucleic acid-binding molecules. For example, low surface density is typically used with the substrate-attachment schemes shown in FIGS. 4B, 4C, and 4D. The target nucleic acids can be hybridized to the capture molecules before or after the target nucleic acid is bound to a nucleic acid-binding molecule. Barcode transfer from the nucleic acid binding-molecule to the target nucleic acid may, in some embodiments, occur in the surface-bound state (i.e., when the target nucleic acid is coupled to the substrate).

Beads for target nucleic acid capture by hybridization can be prepared by direct conjugation of 5'-amino-modified oligonucleotides to surface-activated beads. The surface-activated beads may exhibit epoxy, tosyl, carboxylic acid or amine groups for covalent linkage. Carboxy beads typically need to be reacted with carbodiimide to facilitate peptide bond formation, and amine beads typically require a bifunctional NHS-linker. In some embodiments, the surface of the bead is passivated to prevent non-specific binding. Passivation can be achieved, in some embodiments, by co-grafting poly-ethylene glycol (PEG) molecules with the same linkage chemistry. For example, 5'-amino-modified oligonucleotides and amino-terminated polyethylene glycol (PEG) is used such that, on average, most substrate sites will be occupied by PEG molecules that will serve to spatially distribute the oligonucleotides. If an excess of PEG is used, the oligonucleotides will be, on average, spatially separated from one another. The surface density of capture molecules can be adjusted by altering the ratio of oligonucleotide to PEG molecules.

In some embodiments, the beads are Sepharose beads made with mTet (tetrazine) and carboxy-PEG. A reduced ratio of mTet to carboxy-PEG reduces crosstalk between target nucleic acids. In some embodiments, the mTet:carboxy-PEG ratio is 1:500, 1:600, 1:700, 1:800, 1:900, 1:1000, 1:1100, 1:1200, 1:1300, 1:1400, 1:500, 1:1000, 1:2000, 1:3000, 1:4000, 1:5000, 1:6000, 1:7000, 1:8000, 1:9000, or 1:10000. In some embodiments, the mTet:carboxy-PEG ratio is 1:1000.

Binding Domain—Enzyme Conjugates

Also provided herein are conjugates comprising a binding domain coupled to an enzyme, or a fragment thereof. The enzyme or fragment thereof may be catalytically active or catalytically inactive. In some embodiments, the enzyme or fragment thereof may be covalently or non-covalently coupled to the binding domain. For example, the enzyme or fragment may be synthetically tethered to the binding domain, or genetically fused to the binding domain. In some embodiments, the binding domain and the enzyme (or fragment) may be expressed as a single transcript (e.g., as a fusion protein). In some embodiments, the binding domain is coupled to the enzyme (or fragment) via a linker.

In some embodiments, enzyme may be a nucleobase editing enzyme (also referred to herein as a base editing enzyme). The base editing enzyme may be, for example, an adenosine deaminase, a cytosine deaminase, a glycosylase, a methylase, a demethylase, a dioxygenase or any other enzyme that modifies one or more nucleobases of DNA or RNA.

In some embodiments, the enzyme may be a transposase. In some embodiments, the enzyme is a Tn5 transposase. Transposases exist in both prokaryotes and eukaryotes and catalyze the movement of defined DNA elements (transposon) to another part of the genome in a 'cut and paste' mechanism. Transposases are widely used in many biomedical applications. For example, an engineered, hyperactive Tn5 transposase from E. coli can bind to a double-stranded synthetic 19 bp mosaic end (ME)-recognition sequences that can be appended to any sequencing adapter. In some embodiments, the ME-adapter comprises CTGTCTCT-TATACACATCT; SEQ ID NO: 58.

In some embodiments, the ME-adapter comprises AGATGTGTATAAGAGACAG; SEQ ID NO: 59. In some embodiments, the ME-adapter comprises TTTGTGAUGC-GATGAACTCAGAGTGCTTNNNNNNNNNNNNA-GATGTGTATAAGAGA CAG; SEQ ID NO: 60, wherein N is the barcode. In some embodiments, the mosaic end comprising SEQ ID NO: 58 is hybridized to the ME-adapter comprising SEQ ID NO: 60. Each transposase molecule simultaneously loads two ME-tagged adapters. Tn5 transposase has been utilized for in vitro tagmentation reactions (simultaneously fragment and tag a target sequence with sequencing adaptors) using double-stranded DNA or RNA/DNA heteroduplexes as a substrate. The major advantage of tagmentation is that it reduces the amount of input nucleic acid and significantly simplifies the assay workflow. Tagmentation is commonly performed with picograms of DNA or RNA and has been successful for single cell approaches.

In some embodiments, a binding domain-enzyme conjugate comprises a binding domain that specifically binds RNA modifications, DNA modifications, or both RNA and DNA modifications, and which directs transposase to target nucleic acids. Conjugated to the modification specific binding domain, the transposase inserts specific barcodes into the RNA/DNA duplex thereby also appending universal and reverse primer sites. Tagmentation is magnesium ion dependent and tagmentation may be triggered by addition of magnesium ions. The length of the tagmented duplex depends on the reaction conditions and can be optimized to be as short as 30 base pairs. Thus, targeted tagmentation can detect DNA or RNA modifications with a base resolution of up to 30 base pairs.

In some embodiments, transposase may not be directly tethered or fused to the binding domain that recognizes the DNA/RNA modification. In some embodiments, the transposase may be tethered or fused to a peptide or protein domain that covalently or non-covalently binds to a structural element of the binding domain that recognizes the DNA/RNA modification. In some embodiments, the binding domain, for example an antibody, is genetically fused to a Spy-tag peptide, whereas transposase is genetically fused to SpyCatcher protein. Spy-tag and Spy-Catcher will spontaneously form a covalent bond and thus target transposase to the modification site. In some embodiments, transposase is genetically fused to protein A, G, or L. In some embodiments, transposase is genetically fused to protein A. In some embodiments, transposase is genetically fused to protein G. In some embodiments, transposase is genetically fused to protein L. Protein A, G, or L bind to specific regions of IgG antibodies and direct transposase activity to DNA or RNA modification-bound antibodies.

In some embodiments, transposase may bind to ME-tagged adapters that are covalently conjugated to the binding domain. The adapter may be present as a ME-tagged single strand and hybridization of the ME complement triggers loading of the transposase in situ. The binding domain may display two or more ME-adapter molecules to enable loading of the transposase with two adapters, which is necessary for tagmentation. In some embodiments, the ME-adapter molecules have the same sequence. In some embodiments, the ME-adapter molecules have different sequences. In some embodiments, the ME-adapter comprises a barcode specific to the DNA or RNA modification.

Cytosine deaminase catalyzes the hydrolytic deamination of cytosine to uracil, thus mutating a CG base pair to a TA base pair. Cytosine deaminases of the APOBEC (Apolipoprotein B mRNA Editing Catalytic Polypeptide-like) family of proteins have diverse and important functions in human health and disease. All APOBEC enzymes bind single-stranded DNA and RNA, but only some of them deaminate RNA bases. Notably, APOBEC1 and APOBEC3A modify DNA and RNA. The E. coli cytosine deaminase CodA catalyzes the conversion of 5-fluorocytosine (5FC) to 5-fluorouracil (5FU); this activity allows the formation of a cytotoxic chemotherapeutic agent from a non-cytotoxic precursor. APOBEC enzymes have been engineered to process double-stranded DNA.

Adenosine deaminase that act on RNA (ADAR) catalyzes the hydrolytic deamination of adenosine to inosine. Because inosine acts like guanine in the cell machinery, this equates to mutating a A•T base pair to a G•C base pair. Two different enzymes are responsible for adenosine deamination in humans: ADAR1 and ADAR2. ADAR proteins have a modular structure with double stranded RNA binding domains and a C-terminal deaminase domain. Double-stranded RNA is required for ADAR activity; however, a recent report demonstrates ADAR activity on the DNA strand of an RNA/DNA heteroduplex. Recently ADAR2 was engineered to perform cytosine to uracil conversion in addition to adenosine to inosine conversion.

In some embodiments, a binding domain-enzyme conjugate comprises a binding domain that specifically binds RNA and/or DNA modifications, and which directs cytosine and adenosine deaminase to target nucleic acids. At the target site, deaminase enzymes introduce a single point location, which marks the location of the DNA/RNA non-canonical feature. Base editing is another method for localizing modifications and is an alternative to generating truncated cDNA by photo-crosslinking of proteins and nucleic acids for this purpose. In some embodiments, cytosine to uracil editing may be used to introduce a cleavage site.

Figure 6A:
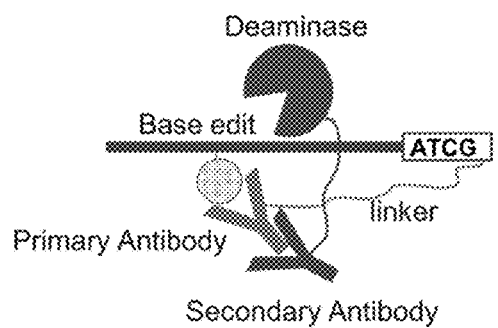
FIGS. 6A-6D is a schematic showing different architectures for targeting a nucleic acid-modifying enzyme (in this example a deaminase) to the site of nucleic acid modification. The approaches include tethering of the deaminase to a secondary antibody that binds to a primary antibody (FIG. 6A), tethering of the deaminase to an oligonucleotide that hybridizes to a complementary oligonucleotide (DNA address) attached to a nucleic acid binding domain (FIG. 6B), and genetically fusing the deaminase to the SpyCatcher protein, which spontaneously forms a covalent bond with the peptide SpyTag displayed by a nucleic acid binding domain (FIG. 6C). Alternatively, the deaminase may be tethered to a Protein G that binds to a primary antibody (FIG. 6D). Nucleotide sequences are provided as exemplary barcoding sites (SEQ ID NOs: 52-54).
Figure 6B:
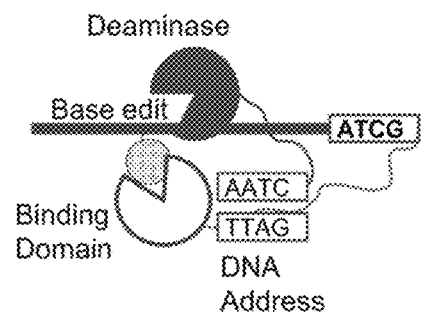
Figure 6C:
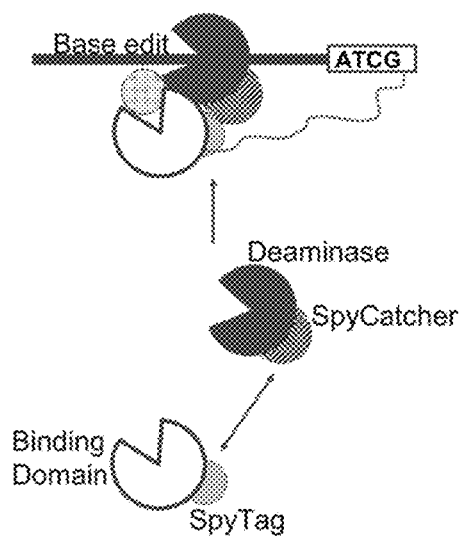
Figure 6D:
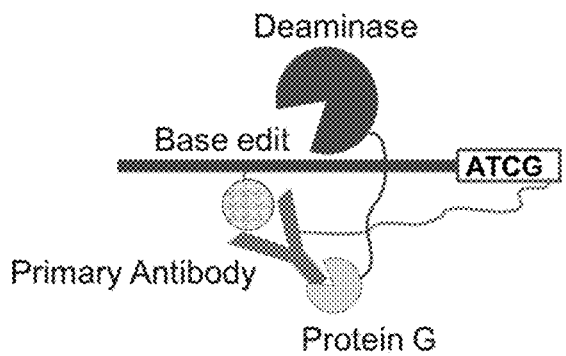

In some embodiments, the base editing enzyme may not be directly tethered or fused to the binding domain that recognizes the DNA/RNA modification. Instead, the base editing enzyme may be tethered or fused to a peptide or protein domain that covalently or non-covalently binds to a structural element of the binding domain that recognizes the DNA/RNA modification as shown in FIG. 6A-6C. For example, the binding domain that recognizes the RNA/DNA modification may be a primary antibody and the deaminase enzyme is tethered or fused to a secondary antibody (FIG. 6A). In some embodiments, the binding domain, for example a nanobody, exhibits a DNA adapter comprising a DNA address, a linker and the barcode. The deaminase is labeled with a sequence complementary to the DNA address that targets the enzyme to the modification site via DNA hybridization (FIG. 6B). In some embodiments, the binding domain, for example a nanobody, is genetically fused to a Spy-tag peptide, whereas deaminase is genetically fused to SpyCatcher protein. Spy-tag and Spy-Catcher will spontaneously form a covalent bond and thus target the deaminase to the modification site (FIG. 6C). In some embodiments, the deaminase is fused to a Protein G which binds to a primary antibody (FIG. 6D). In some embodiments, the enzyme is a base editing enzyme fused to protein A (UniProt accession No. P38507 & P02976), protein G (UniProt accession No. Q54181 & P19909), or Protein L (UniProt accession No. Q51918). In some embodiments, the enzyme is a base editing enzyme fused to protein A. In some embodiments, the enzyme is a base editing enzyme fused to protein G. In some embodiments, the enzyme is a base editing enzyme fused to protein L.

In some embodiments, a conjugate comprises (i) a nucleic acid binding molecule and a peptide tag, and (ii) an enzyme or fragment thereof fused to a protein that can covalently react with the peptide tag. In some embodiments, a conjugate comprises (i) an enzyme or fragment thereof comprising a peptide tag, and (ii) a nucleic acid binding molecule fused to a protein that can covalently react with the peptide tag. In some embodiments, a conjugate comprises (i) a nucleic acid binding molecule and a protein tag, and (ii) an enzyme or fragment thereof fused to a peptide tag that can covalently react with the protein tag. In some embodiments, a conjugate comprises (i) a nucleic acid binding molecule and (ii) an enzyme or fragment thereof fused to a protein that can bind with high affinity to specific regions of the binding domain. In some embodiments, the peptide tag is a Spytag. In some embodiments, the enzyme is a deaminase. In some embodiments, the protein that can covalently react with the peptide tag is a Spycatcher protein.

In some embodiments, a conjugate comprises (i) a nucleic acid binding molecule and a peptide tag, and (ii) an enzyme or fragment thereof fused to a protein tag that can covalently react with the peptide tag. In some embodiments, a conjugate comprises (i) an enzyme or fragment thereof comprising a peptide tag, and (ii) a nucleic acid binding molecule fused to a protein tag that can covalently react with the peptide tag. In some embodiments, a conjugate comprises (i) a nucleic acid binding molecule and a protein tag, and (ii) an enzyme or fragment thereof fused to a peptide tag that can covalently react with the protein tag. In some embodiments, a conjugate comprises (i) a nucleic acid binding molecule and (ii) an enzyme or fragment thereof fused to a protein tag that can bind with high affinity to specific regions of the binding domain. In some embodiments, the peptide tag is a Spytag. In some embodiments, the enzyme is a deaminase. In some embodiments, the protein that can covalently react with the peptide tag is a Spycatcher protein.

In some embodiments, the conjugate is a covalent linkage. In some embodiments, the conjugate is a non-covalent linkage.

Nucleic Acid Analysis Methods, Including Localization of a Non-Canonical Feature by Modification or Editing of a Target Nucleic Acid The nucleic acid-binding molecules described herein, which are capable of intra-complex barcode transfer as described above, may be used in various methods of analyzing nucleic acids, specifically for recognizing non-canonical features on target nucleic acids. This disclosure thus provides methods for analyzing non-canonical features on target nucleic acids, including methods for multiplexed profiling of RNA and DNA modifications across transcriptomes and genomes. In these methods, non-canonical features of an RNA or DNA are recognized by a binding domain of a nucleic acid-binding molecule. The adapter or part thereof (e.g., a barcode) is then transferred from the nucleic acid-binding molecule to the target nucleic acid (i.e., to generate a labeled/barcoded target nucleic acid). Because the barcode is unique to the particular non-canonical feature bound by the target nucleic acids, this step serves to write the information from the recognition event into the nucleic acid sequence of the target nucleic acid. The resultant barcoded target nucleic acid is then converted into a sequencing library, and read by DNA/RNA sequencing methods. This step reveals the sequence of the barcode, which is correlated with the non-canonical feature in the target nucleic acid(s). Sequencing may also allow for localization of the non-canonical feature in the target nucleic acid(s). The high throughput profiling methods described herein allow for identification of the nature and location of several or all DNA/RNA modifications in parallel.

The methods described herein comprise a series of steps, as described below. As will be understood by those skilled in the art, in some embodiments, various steps may be omitted and/or performed in a different order.

Contacting the Nucleic Acid-Binding Molecules and the Target Nucleic Acids

In some embodiments, the methods described herein comprise a step of contacting one or more nucleic acid-binding molecules with one or more target nucleic acids. The target nucleic acid(s) may comprise DNA, RNA, or a combination of DNA and RNA. The target nucleic acids may be, for example, isolated from a cell or tissue of an organism. In some embodiments, the target nucleic acids may be fragmented.

Contacting the nucleic acid-binding molecule(s) with the target nucleic acid(s) may occur in solution. For example, a composition comprising one or more target nucleic acids may be contacted with a composition comprising one or more nucleic acid-binding molecules. In some embodiments, the contacting may occur in a dilute solution, so that only one nucleic acid-binding molecule may interact with each target nucleic acid.

In some embodiments, the contacting occurs on a substrate. For example, one or more target nucleic acids may be coupled to a substrate, and one or more nucleic acid-binding molecules may be contacted with the target nucleic acids coupled to the substrate. In some embodiments, one or more nucleic acid-binding molecules may be coupled to a substrate, and one or more target nucleic acids may be contacted with the nucleic acid-binding molecules coupled to the substrate. Substrates comprising nucleic acid-binding molecules, and methods for making the same, are described above and illustrated in FIGS. 4A-4D and FIGS. 5A-5C.

The target nucleic acids may be contacted with only one type of nucleic acid-binding protein (i.e., to detect only one type of non-canonical feature), or in some embodiments, the target nucleic acids may be contacted with more than one type of nucleic acid-binding molecule, to detect multiple non-canonical features. For example, the target nucleic acids may be contacted with at least one, at least two, at least three, at least four, at least five, at least six, at least seven, at least eight, at least nine, at least ten, or more different types of nucleic acid-binding molecules. In some embodiments, the target nucleic acids may be contacted with 1-5, 5-10, 10-25, 25-50, 50-100, 100-150, 150-175, 175-200, or more different types of nucleic acid-binding molecules. When multiple types of nucleic acid-binding molecules are used, the contacting may occur at the same time (i.e., the target nucleic acids are contacted with multiple nucleic acid-binding molecules recognizing different non-canonical features simultaneously), or the contacting may be sequential (i.e., the target nucleic acids are contacted with a first nucleic acid-binding molecule recognizing a first non-canonical feature, and then later contacted with a second nucleic acid-binding molecule recognizing a second non-canonical feature).

In some embodiments, the target nucleic acids are contacted with a first pool of nucleic acid-binding molecules, and then later contacted with a second pool of nucleic acid-binding molecules. In some embodiments, the pools may comprise different types nucleic acid-binding molecules (i.e., recognizing different types of non-canonical features). In some embodiments, the pools may each comprise 1-5, 5-10, 10-25, 25-50, 50-100, 100-150, 150-175, 175-200, or more different types of nucleic acid-binding molecules.

Barcode Transfer

Each nucleic acid-binding molecule binds specifically to a non-canonical features of a target nucleic acid, bringing the adapter of the nucleic acid in close proximity to either the 3' or the 5' end of the target nucleic acid. The adapter (e.g., an adapter comprising or consisting of a barcode) may then by transferred to the target nucleic acid. In some embodiments, the transferring occurs in an environment that substantially prevents off-target generation of barcoded nucleic acids. Such an environment may be, for example, an environment wherein the target nucleic acids cannot interact with one another (i.e., only one nucleic acid-binding molecule may interact with each target nucleic acid). This may be achieved, for example, by performing the barcode transfer reaction in a very dilute solution, or by immobilizing either the target nucleic acid or the nucleic acid-binding molecule on a substrate to achieve spatial separation thereof. In some embodiments, the transferring is performed by copying the target nucleic acid, to generate a labeled/barcoded copy of the target nucleic acid. For example, if a barcode is transferred to a target nucleic acid, or is brought into close proximity to a target nucleic acid, polymerase chain reaction (PCR) may be used to generate a barcoded copy of the target nucleic acid.

Barcode transfer reactions and spatial separation are described above, and in FIG. 3A-3E.

Modification of the Target Nucleic Acid (or a Copy Thereof)

In some embodiments, the method may comprise a step of modifying the barcoded target nucleic acid(s) or a barcoded copy(ies) thereof. This modification may occur after the nucleic acid-binding molecule has been bound to the non-canonical feature, and in some embodiments, may occur after the barcode has been transferred to the target nucleic acid (or a barcoded copy of the target nucleic acid has been generated).

Modification is performed so that the position of the non-canonical feature is identifiable based on the primary nucleic acid sequence of the barcoded target nucleic acids, or the barcoded copies thereof, and may therefore be detected in downstream sequencing steps. Many different types of modifications may be used for this purpose. For example, in some embodiments, the modification may prevent polymerase bypass during copying of the target nucleic acid (or barcoded copy thereof).

In some embodiments, the modification is achieved, in part, by chemically modifying the binding domain of the nucleic acid-binding molecule. This may, in some embodiments, induce truncation during copying of the target nucleic acid, while the binding domain is bound thereto.

In some embodiments, the modification comprises photochemically linking the nucleic acid-binding molecule (or a fragment thereof, such as the binding domain) to the target nucleic acid (or barcoded copy thereof). Methods for photochemically linking a nucleic acid and a protein are known to those of skill in the art. For example, photochemical linkages may be induced by exposing complexes comprising nucleic acid-binding molecules and a target nucleic acid to ultraviolent (UV) light.

In some embodiments, the modification comprises editing a base at or near the site where the nucleic acid-binding molecule is bound to the target nucleic acid. For example, the base may be edited using cytosine deaminase or adenosine deaminase. The base editing molecule may optionally be coupled to the nucleic acid-binding molecule or a part thereof, or it may be coupled to a binder that recognizes the nucleic acid-binding molecule, for example a secondary antibody that binds to a primary antibody-DNA adapter conjugate (FIG. 6A-6C). Adenosine deaminase converts an adenosine (A) to inosine (I), which amplification enzymes base pair with cytosine (C) introducing a thymine (T) to cytosine (C) mutation. Cytosine deaminase converts a cytosine (C) near the modification site to uracil (U), introducing a guanine (G) to adenosine (A) mutation. Another way to localize the non-canonical feature is to cleave uracil (U) subsequently by USER™ from NEB® (a mixture of the enzymes uracil deglycosylase and endonuclease VIII), which produces a truncated read.

Amplification and Sequencing

After a target nucleic acid (or barcoded copy thereof) has been modified, it may be amplified and then sequenced. This step reveals the sequence of the barcode, which is correlated with the non-canonical feature originally bound by the nucleic acid-binding molecule in the target nucleic acid(s). Sequencing may also reveal the length of a truncated fragment, which allows for localization of the non-canonical feature in the target nucleic acid(s). Sequencing may also reveal a mutation near the non-canonical feature, from which the location of the non-canonical feature can be derived informatically. The mutation may be a result of base editing with a deaminase enzyme, or it may result from an increased base insertion error rate of the enzyme that is used to copy the nucleic acid target (a DNA polymerase if the target is DNA, or a reverse transcriptase if the target is RNA). The non-canonical feature may naturally increase the enzymatic bypass error rate, or the effect may be amplified by chemically modifying the non-canonical feature.

Thus, in some embodiments, the method described herein may comprise a step of sequencing the barcoded target nucleic acids, or copies thereof. The sequencing step may be performed using any suitable method known in the art. For example, the sequencing may be performed using a next-generation sequencing (NGS) method, a massively parallel sequencing method, or a deep sequencing method. There are a number of NGS platforms that may be used with the methods of the instant disclosure. For example, Illumina® (Solexa®) sequencing works by simultaneously identifying DNA bases as each base emits a fluorescent signal and adding them to a nucleic acid chain. Roche® 454 sequencing is based on pyrosequencing, a technique which detects pyrophosphate release using fluorescence, after nucleotides are incorporated by a polymerase to a new strand of DNA. Ion Torrent (Proton/PGM sequencing) measures the direct release of protons (H+) from the incorporate of individual nucleotides by DNA polymerase.

In some embodiments, sequencing is not required to detect a target nucleic acid. For, example, the target nucleic acid may be detected using PCR. For example, PCR may be used to detect whether a target nucleic acid (e.g., a barcode) is present. In some embodiments, a target nucleic acid is detected using a fluorescent probe (e.g., a fluorescently-labeled hybridization probe). In some embodiments a target nucleic acid is detected using a microarray or other nucleic acid array. Methods for analyzing sequencing results or data from any of the methods for detecting target nucleic acids described herein are known to those of skill in the art. For example, standard bioinformatics methods are used to analyze sequencing results.

In some embodiments, sequencing is not required to detect the addition of a barcode by a reaction mediated by the nucleic acid binding molecule. For example, the presence of a DNA/RNA modification may be confirmed by detecting the associated barcode using nucleic acid electrophoresis, a fluorescent hybridization probe, PCR or any other nucleic acid amplification method that can be triggered by the barcode.

Figure 8:
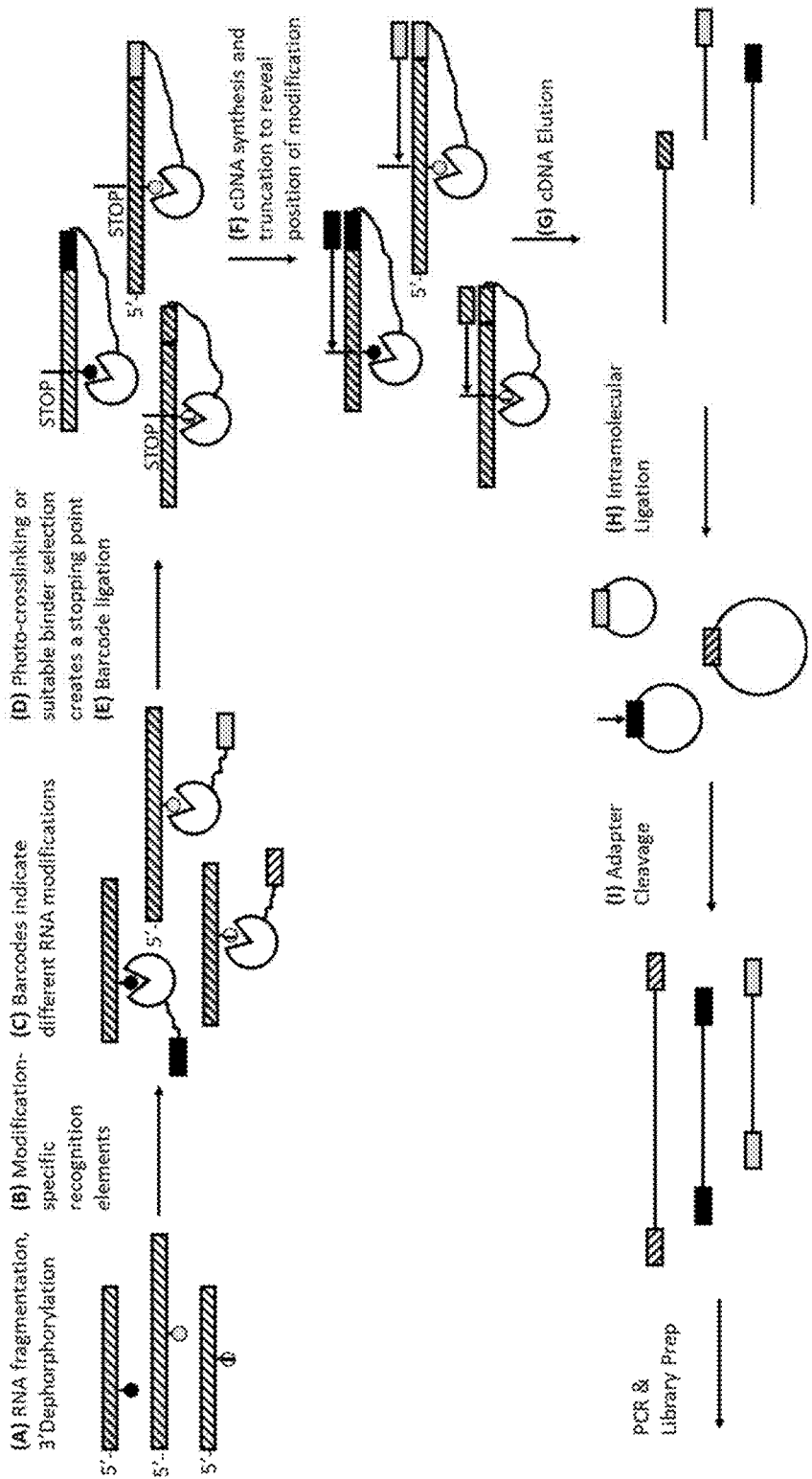
FIG. 8 is a schematic showing an illustrative method for RNA profiling by barcode ligation and cDNA truncation. Following cDNA truncation, the samples are amplified by PCR and prepared for sequencing.

Illustrative Methods for Identification, Quantification, and or Localization of a Non-Canonical Feature on a Target Nucleic Acid In some embodiments, the methods described herein may be used to not only identify the modification (i.e., a non-canonical feature) on a target nucleic acid, but also to quantify the modification and localize the modification on the target nucleic acid with a resolution as high as 1 base (see, e.g., FIG. 8). In some embodiments, the methods allow for localization of the modification at a resolution as high as 2 bases, 3 bases, 4 bases, 5 bases, 6 bases, 7 bases, 8 bases, 9 bases, or 10 bases.

Figure 7:
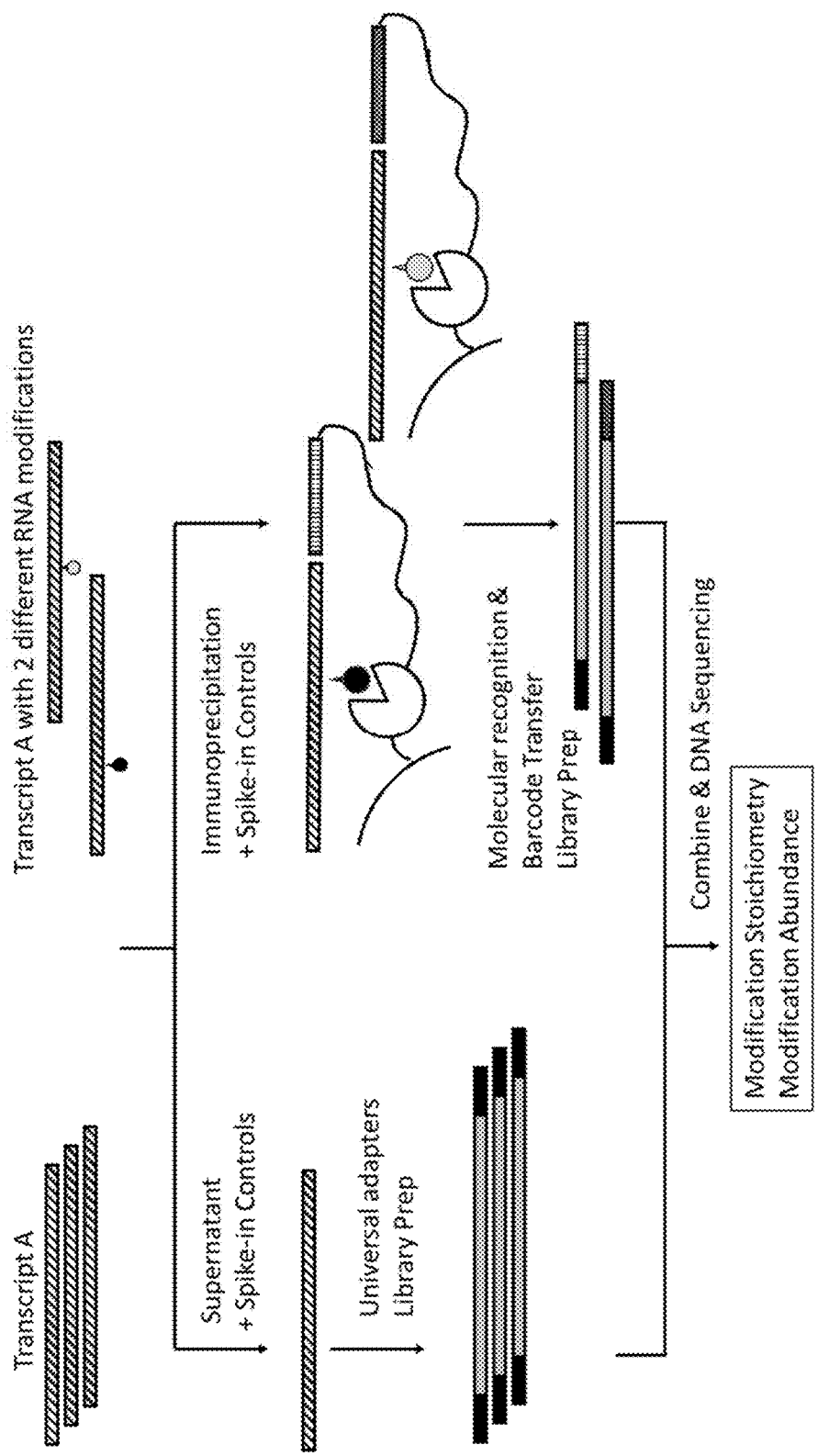
FIG. 7 is a schematic showing an illustrative RNA seq workflow with modification analysis that is geared towards measuring the stoichiometry and abundance of an RNA modification.

In some embodiments, an RNA sample comprising modified and unmodified RNA transcripts is provided as shown in the dual-workstream approach outlined in FIG. 7. In this figure, unmodified RNA transcripts are labeled "Transcript A," and the Type 1 and Type 2 RNA modifications represent any type of modification. Each transcript of the RNA sample may or may not comprise a non-canonical feature.

The RNA transcripts are then contacted with beads, wherein the beads are coupled, directly or indirectly, to nucleic acid-binding molecules specific for a non-canonical feature (i.e., the Type 1 and/or Type 2 RNA modifications of FIG. 7). The modified RNA molecules bind to the beads, whereas unmodified RNA remains in the supernatant. To be able to quantitate the level of RNA modifications, both fractions (substrate-bound and supernatant) may be processed and converted into sequencing libraries. Unmodified RNA molecules are capped on each end with adapters comprising a UFP and a URP, whereas the modified RNA molecules receive a barcode indicative of their modification (i.e., it is transferred from the nucleic acid-binding molecule bound thereto).

As shown in FIG. 7, normalization probes (controls) may be spiked into both work streams (surface bound, supernatant) to enable relative quantification. In addition, absolute quantification can be accomplished by counting unique molecular identifiers that may be present in the adapters of the nucleic acid-binding molecules. Many RNA modifications occur at low copy numbers. Accordingly, the split workflow has the advantage that the modified and unmodified fractions can be combined at a ratio that provides optimal sensitivity for the low copy number transcripts at a given sequencing depth. This split-workflow allows for measuring the stoichiometry and abundance of an RNA modification. The "stoichiometry" is a relative number and is calculated as the number of copies of a particular locus that contain a non-canonical feature divided by all copies of this locus. The "abundance" is the absolute number of occurrences of a non-canonical feature of a nucleic acid at a given locus.

In some embodiments, a method for analyzing a plurality of target nucleic acids may comprise RNA profiling by barcode transfer by ligation, and localizing the non-canonical feature by cDNA truncation (see, e.g., FIG. 8). In some embodiments, the method comprises depleting or enriching an RNA sample, for example by physically or chemically fragmenting the RNA using conditions that preserve RNA modifications (see FIG. 8, step A). One or more nucleic acid-binding molecules may then be added to the RNA sample. The binding domain of the nucleic acid-binding molecules recognizes the RNA modifications, and juxtaposes adapters (e.g., adapters containing DNA barcodes) to the ends of the RNA target (see FIG. 8, step B). In some embodiments, to generate a mark that prevents reverse transcriptases from copying past the recognition element (i.e. the modification), the target RNA and the binding domain of the nucleic acid-binding molecule may be cross-linked (e.g., photochemically cross-linked). In some embodiments, a stopping point may be created without cross-linking by selecting and engineering for recognition elements that disrupt polymerase-RNA interactions and/or present additional reactive groups that can be engaged for the same purpose (see FIG. 8, step D). Single-stranded adapter ligation may then be used to provide a primer binding site for reverse transcription, and cDNA may be synthesized by primer extension (see FIG. 8, step F). The cDNA is synthetized such that the end of the transcript marks the position of the RNA modification. The resolution by which the modification may be localized will depend on the nature of the truncation mechanism.

cDNA molecules may be circularized. For example, cDNA molecules with Type B adapters may be circularized by Circligase (see FIG. 8, step H). Cleavage of the circularized cDNAs releases linear cDNA fragments that are strand-specific and can be easily converted into a sequencing library using PCR amplification (see FIG. 8, step I). Primers may be used to introduce additional adapter pieces, which are useful for downstream processes such as sequencing.

Figure 9:
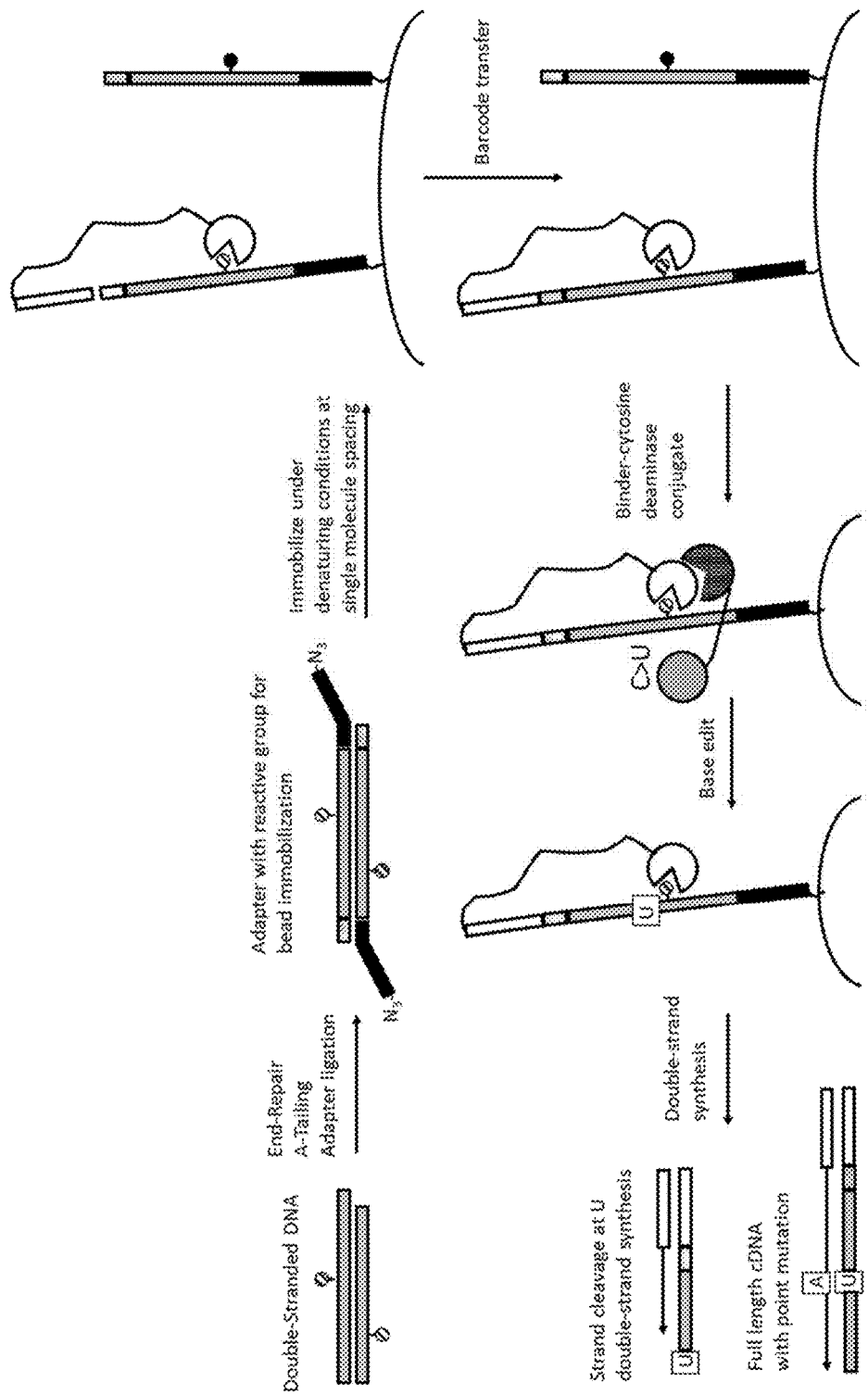
FIG. 9 is a schematic showing an illustrative method for DNA profiling by barcode ligation and base editing with cytosine deaminase.

FIG. 9 illustrates a method for analyzing DNA modifications by barcoding and enzymatic base editing (e.g., adding a uracil) to create a truncation site. Since DNA is double-stranded and base editing with deaminase enzyme requires a single stranded nucleic acid, the first step is separate the DNA strands. This may be done by ligating Y-shaped adapters to ends of the DNA fragments according to standard protocols (i.e., end repair, A-tailing, adapter ligation). In some embodiments, one arm of the Y-shaped adapter contains a 5' azido group as chemical handle. Double-stranded DNA may be denatured in 95% formamide, and then coupled to a bead, such as a magnetic bead. For example, magnetic beads with surface exposed alkyne groups (at a density of 1 alkyne group per 100 nm 2) may be added. The addition of Cu(I) triggers covalent attachment of the nucleic acids to the beads. Because complementary DNA strands are now randomly affixed to the surface of the beads, and spatially separated from one another, they cannot hybridize under physiological buffer conditions. The single-stranded DNA coupled to the beads may then be contacted by nucleic acid-binding molecules and barcodes that are indicative of the DNA modification. Subsequently, barcodes may be transferred to the single-stranded target nucleic acid by ligation. A binding domain-enzyme conjugate is then is added that comprises, for example, an antibody (e.g., an anti-mouse antibody) specific for the binding domain of the nucleic acid-binding molecule, and a base editing enzyme (e.g., a cytosine deaminase). As the binding domain-enzyme conjugate contacts the binding domain of the nucleic acid-binding molecule, the enzyme (cytosine deaminase) edits a base in the single-stranded target nucleic acid (e.g., it changes cytosine (C) near the modification to uracil (U)). Deaminase is deactivated and the DNA strand cleaved by addition of USER (which is mixture of uracil deglycosylase and endonuclease VIII). Primer extension by a DNA polymerase generates truncated reads that are indicative of the location of the DNA modification. The reads are converted into libraries that may be sequenced using standard methods.

Figure 10:
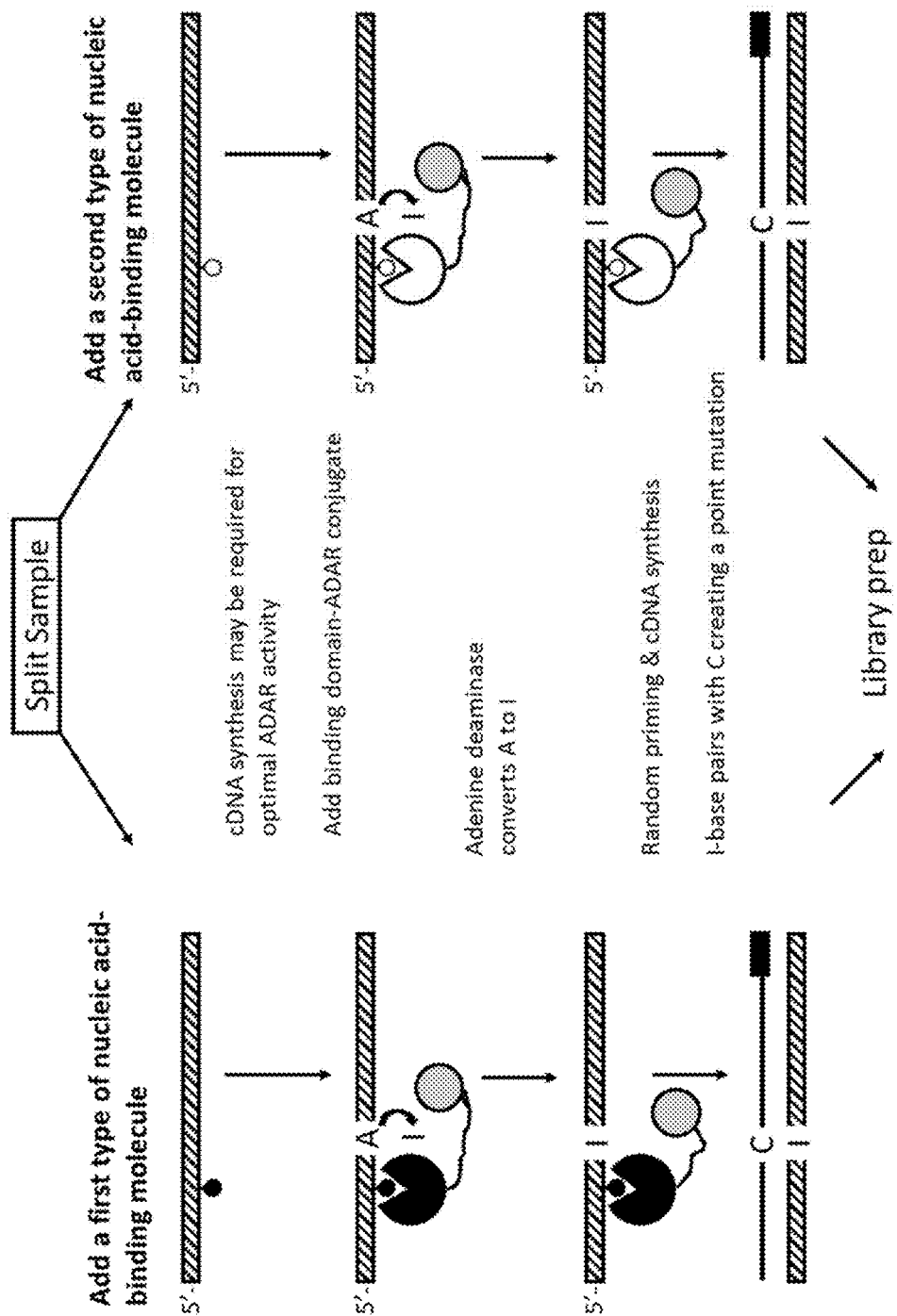
FIG. 10 is a schematic showing an illustrative method for RNA profiling by base editing with adenosine deaminase and sample splitting.

In some embodiments, a method for analyzing a plurality of target nucleic acids may be used to detect/quantify a single type of DNA or RNA modification per reaction. In some embodiments, a method for analyzing a plurality of target nucleic acids may be adapted for detecting multiple DNA or RNA modifications by sample splitting, as shown in FIG. 10. For example, a binding domain conjugated to a base-editing enzyme such as adenine deaminase may be introduced to each reaction. Adenine deaminase converts adenine (A) to inosine (I), which induces a T→C mutation and marks the site of RNA modification. In the split scheme shown in FIG. 10, a binding domain without tethered adapter is used. Each partition contains only a single type of binding domain—deaminase conjugate and after immunoprecipitation a type C adapter is added to each partition and ligated to the enriched targets. Attaching a Type C barcode allows for pooling of the split reactions prior to RNA Seq library preparation.

Figure 11:
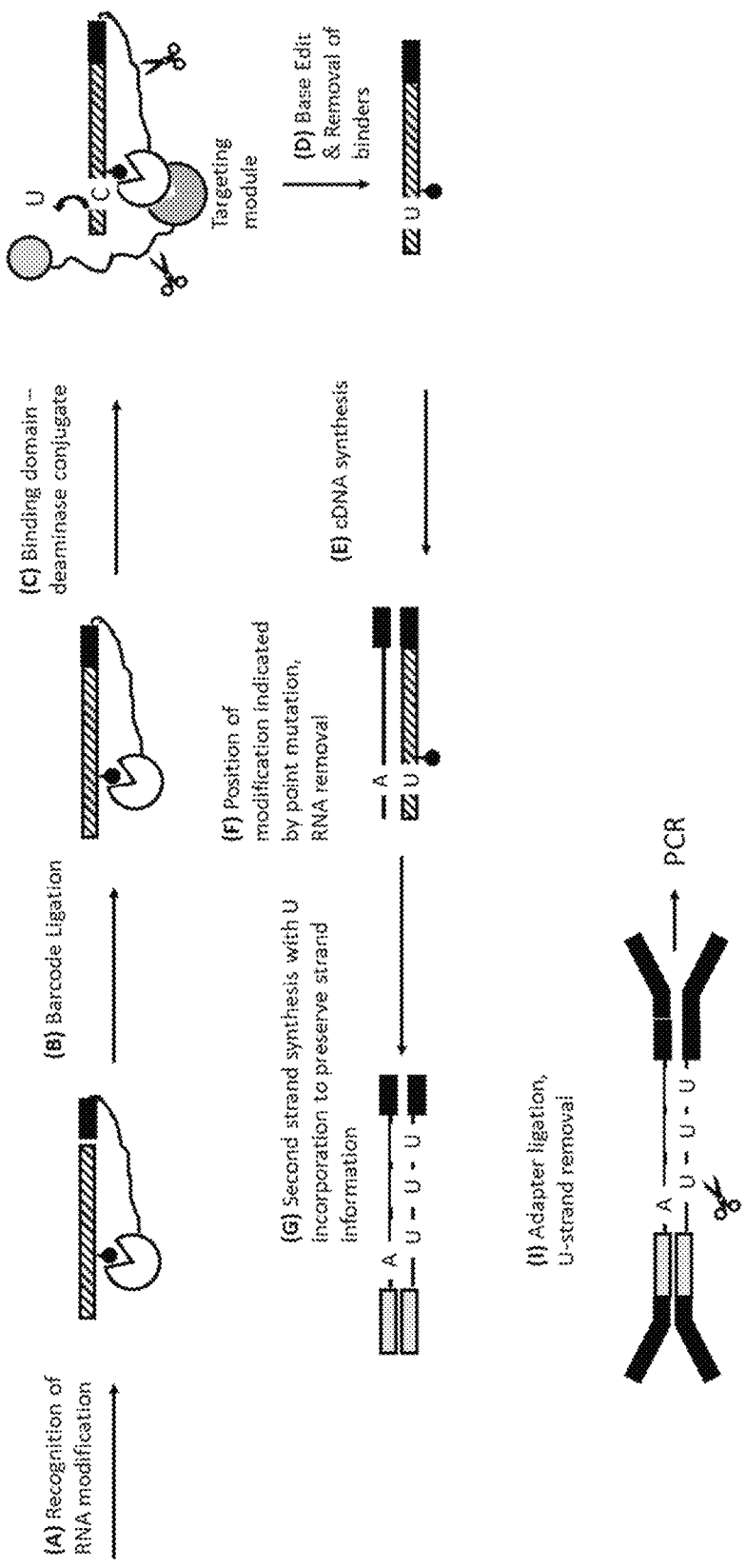
FIG. 11 is a schematic showing an illustrative method for RNA profiling by barcode ligation and base editing with a secondary antibody-adenosine deaminase conjugate and preserving strand information.

In some embodiments, multiplexed modification profiling and base editing may be combined. FIG. 11 illustrates a method for RNA profiling using barcode ligation and base editing with adenosine deaminase. The steps are similar to the workflow shown in FIG. 9, except that the binding domain-enzyme conjugate comprises adenosine deaminase. After converting an adenosine (A) to inosine (I) to indicate the location of the modification and first strand synthesis by reverse transcription, the second cDNA strand is synthesized with a method that preserves strand information. By incorporating uracil exclusively into the second strand, the second strand can be removed by USER cleavage. Stranded RNA library preparation may be advantageous where base editing is used, because only the edited strand is amplified.

Figure 12:
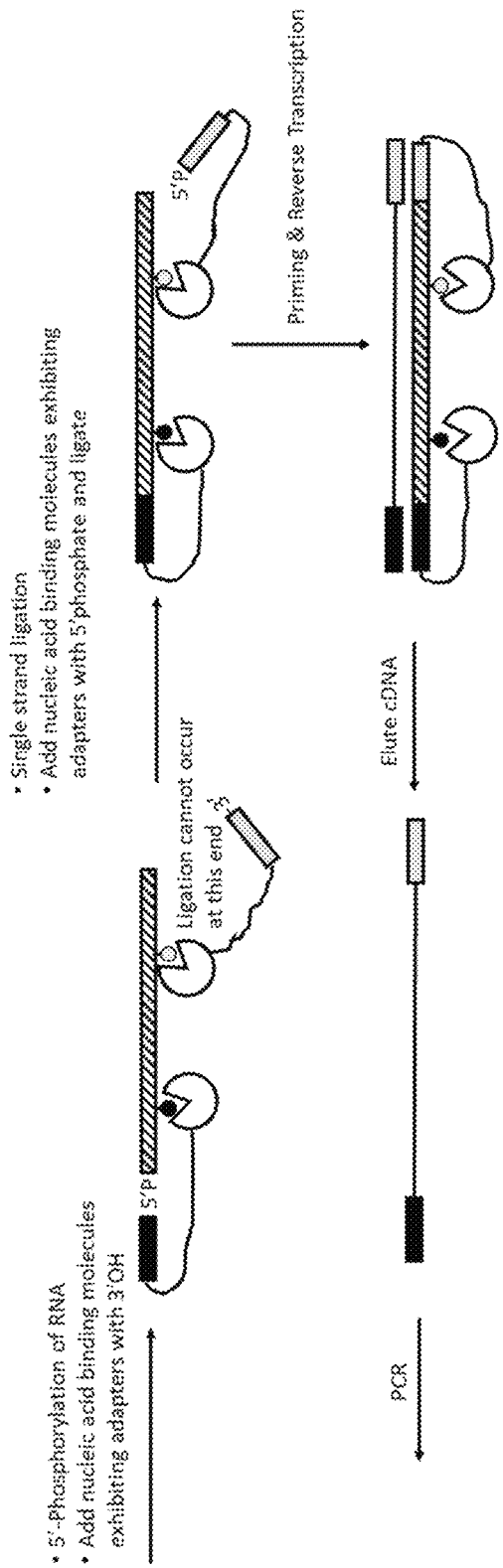
FIG. 12 is a schematic showing an illustrative method for RNA profiling, wherein a target RNA fragment comprises two or more modifications. After cDNA is eluted, samples are amplified by PCR and prepared for analysis.

The methods described herein may also be used to analyze a DNA or RNA which comprises two, or more, modifications (i.e., non-canonical features). For example, as shown in FIG. 12, two cycles of profiling may be employed to append reverse and forward adapters to the 5' and 3' end of the target RNA, respectively. The first step is ligation of a reverse adapter with a free 3' OH to the phosphorylated 5' end of the target RNA fragments. The adapters are tethered to the nucleic acid binding molecule via the 5' end and exhibit a free 3' end. The nucleic acid-binding molecule closest to the 5' end is likely to have an advantage over the recognition element that is bound closer to the 3' end. The barcode is transferred from the nucleic acid-binding molecule, and the remainder of the nucleic acid-binding molecule remains chemically linked to the 5' end. An additional set of nucleic acid-binding molecules with a different adapter architecture may then be added, and conjugated to forward adapters with free 5' ends. The adapters are tethered to the additional nucleic acid binding molecule via the 3' end and exhibit a free 5' phosphorylated end. Depending on the conditions used to remove the nucleic acid-binding molecule used in the first cycle, the binding domains thereof may bind again and block access to the already encoded site, which reduces the chance for double profiling. Barcode transfer from the nucleic acid binding-molecules of the second cycle may be accomplished by extending a splint oligo (e.g., by reverse transcriptase). This scheme produces cDNA fragments with forward and reverse primers that can be amplified by PCR and are ready for sequencing.

Figure 13:
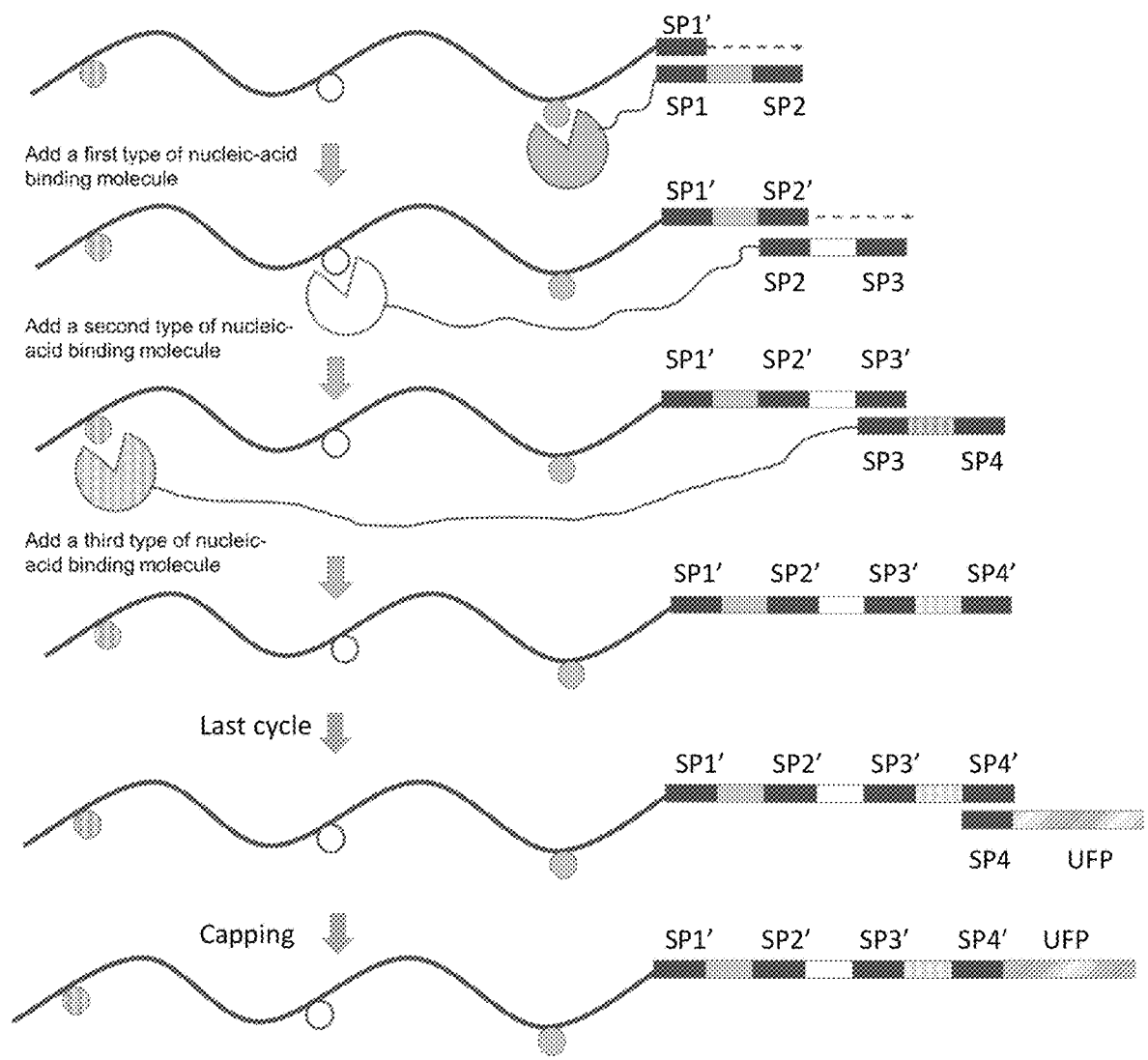
FIG. 13 is a schematic showing an illustrative method for cyclic profiling of multiple RNA modifications. After the illustrated steps are performed, the resulting DNA construct may be reversed transcribed and used for library preparation.

FIG. 13 provides an illustrative reaction scheme for profiling any number of RNA modifications (e.g., 2, 3, 4, 5, 6, 7, 8, 9, 10, or more RNA modifications). In the first step, a single stranded spacer is ligated to a target nucleic acid. Next, a nucleic acid-binding molecule with a Type D adapter is added. If a matching RNA modification is present, the binding domain of the nucleic acid-binding molecule binds and allows the spacer region of the Type D adapter to anneal. Barcode and spacer are copied by a DNA polymerase such as Klenow fragment, Bsu polymerase, T4 and T7 polymerase, Bst polymerase or similar. Then, the nucleic acid-binding molecule is removed, and the target nucleic acids are contacted with a second nucleic acid-binding molecule (i.e., a nucleic acid-binding molecule with a different binding specificity), which adds another barcode to the 3'end. In the last cycle, the 3' end is capped with a universal primer (e.g., UFP or URP), which is used as a primer for reverse transcriptase.

FIG. 14B illustrates a method that addresses a situation where, in each cycle of modification analysis, multiple copies of the same type of modification are present along a target RNA strand and deaminase is targeted to the binding domain via the hybridization of complementary DNA addresses. The presence of one or more of the same modifications is indicated by barcode transfer with a Type G adapter, which is derived from the Type D adapter, as described in FIG. 13. The binding domain-Type G adapter conjugate used in this method includes an DNA address, Address1. Following the binding of this binding domain, barcode transfer by primer extension is initiated. To mark the position of each modification, a conjugate comprising a cytidine deaminase and a complementary DNA address (Address 1') is added and binds to the address (Address1) in the binding domain-Type D adapter conjugate. The deaminase is allowed to edit all modification sites in cycle 1. In cycle 2, a different binding domain-Type D adapter conjugate including Address2 is introduced, specific to the other RNA modification. Primer extension is initiated, followed by the addition of the matched cytidine deaminase and Address2', and editing is allowed to mark the positions of the second modification type.

FIG. 15A-15D illustrates a method for barcoding using Tagmentation. This method employs a dimeric nucleic acid-binding molecule comprising a binding domain that is conjugated to a transposase. The transposase molecules are loaded with double-stranded DNA adapters that are indicative of specific RNA modifications. Transposases bind double-stranded DNA adapters, and cut and insert these adapters by ligation to the 5'ends of a double-stranded DNA substrate. They do not tag 3'ends, and the arising gap can be filled by a polymerase reaction. In some embodiments, the transposases can use DNA/RNA heteroduplexes as substrates. Tagmentation reactions typically produce 200-300 nt long fragments and can be optimized by sample input. In some embodiments, nucleic acid-binding molecule-transposase conjugates are added to unfragmented total or enriched/depleted RNA. Upon recognizing a modified RNA base, the transposase inserts specific barcodes into the RNA/DNA duplex thereby also appending universal and reverse primer sites. Filling the gaps using appropriate polymerases completes library preparation. Tagmentation frames the site of RNA modification by specific barcodes and positional information will be obtained by engineering the transposase linker to a length that optimizes positional resolution.

Figure 16:
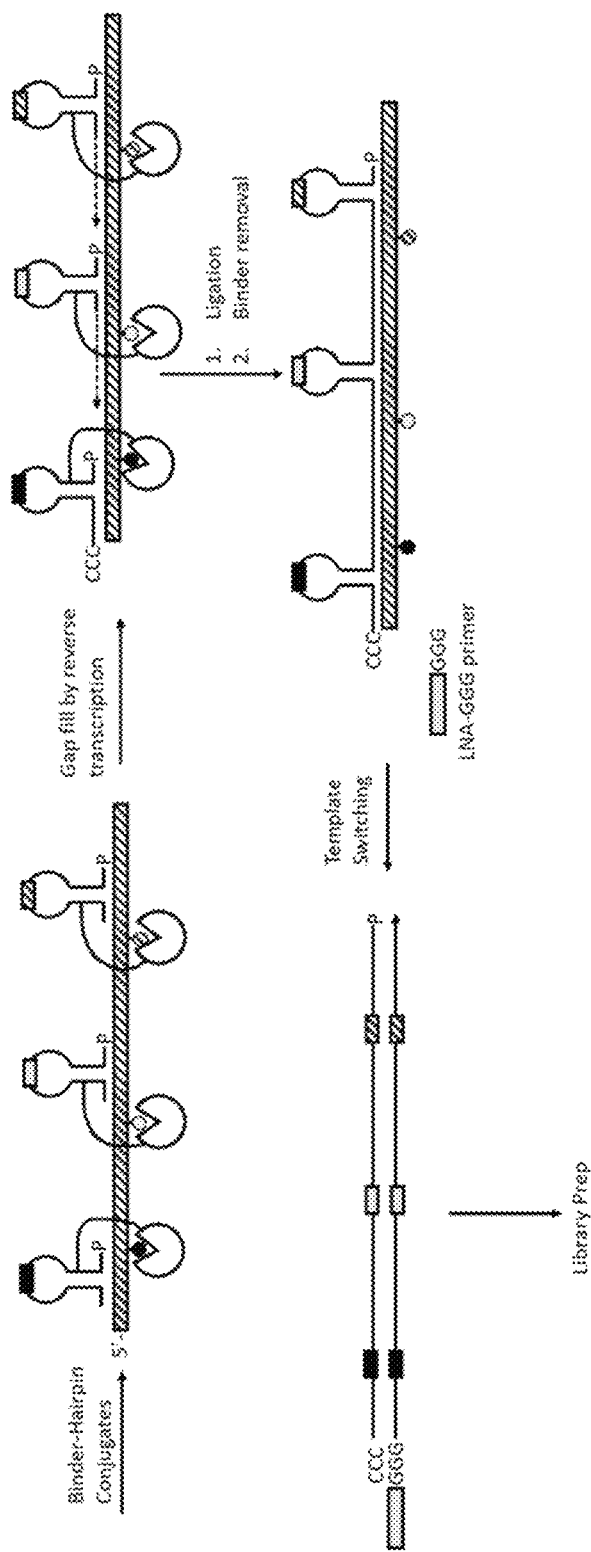
FIG. 16 is a schematic showing an illustrative method for RNA profiling with long read construction.

FIG. 16 illustrates a method for profiling of multiple modifications combined with long read construction using Type E adapters. Type E adapters comprise a barcode and short random feet that hybridize in proximity of the modifications. With suitable linker and feet design they will arrange on the RNA and represent the order and type of RNA modification. The gaps are filled with a reverse transcriptase and connected by ligation. Strand information is preserved by using the smart-Seq approach for template switching. Smart-Seq relies on the property of reverse transcriptase to tail blunt ends with a short poly-C sequence. The poly-C tail is primed with a short LNA-GGG primer that initiates second strand synthesis.

In some embodiments, a method for analyzing a plurality of target nucleic acids comprises: (i) contacting the target nucleic acids with a nucleic acid-binding molecule as described herein; (ii) either (a) transferring the nucleic acid barcode to the target nucleic acids to generate barcoded target nucleic acids, in an environment that substantially prevents off-target generation of barcoded nucleic acids, or (b) generating barcoded copies of the target nucleic acids; (iii) modifying the barcoded target nucleic acids or the barcoded copies thereof, such that the position of the non-canonical feature is identifiable based on the primary nucleic acid sequence of the barcoded target nucleic acids, or the barcoded copies thereof; and (vi) sequencing the barcoded target nucleic acids. In some embodiments, steps (i) to (iii) are repeated at least once (e.g., at least twice, at least three times, at least four times, at least five times, at least six times, at least seven times, at least eight times, at least nine times, at least ten times, or more). In some embodiments, a different nucleic acid-binding molecule is used each time steps (i)-(iii) are repeated. In some embodiments, the same nucleic acid-binding molecule is used each time steps (i)-(iii) are repeated. In some embodiments, the method comprises amplifying the barcoded target nucleic acids or copies thereof prior to sequencing.

In some embodiments, a method for detecting and or quantifying a two or more non-canonical features in plurality of target nucleic acids comprises: (i) contacting the target nucleic acids with at least two nucleic acid-binding molecules, wherein each nucleic acid-binding molecule comprises a binding domain and an adapter; wherein the binding domain of each nucleic acid-binding molecule binds to a different non-canonical feature of a DNA or an RNA; wherein the adapter comprises a nucleic acid barcode sequence unique to the non-canonical feature bound specifically by each binding domain; (ii) either (a) transferring the nucleic acid barcode to the target nucleic acids to generate barcoded target nucleic acids, in an environment that substantially prevents off-target generation of barcoded nucleic acids, or (b) generating barcoded copies of the target nucleic acids; (iii) modifying the barcoded target nucleic acids or the barcoded copies thereof, such that the position of the non-canonical feature is identifiable based on the primary nucleic acid sequence of the barcoded target nucleic acids, or the barcoded copies thereof; and (vi) sequencing the barcoded target nucleic acids. In some embodiments, the method comprises amplifying the barcoded target nucleic acids or copies thereof prior to sequencing.

In some embodiments, a method for detecting a non-canonical feature in a target nucleic acid comprises: (i) contacting the target nucleic acid with a nucleic acid-binding molecule as described herein; (ii) either (a) transferring the nucleic acid barcode to the target nucleic acids to generate barcoded target nucleic acid, in an environment that substantially prevents off-target generation of barcoded nucleic acids, or (b) generating a barcoded copy of the target nucleic acid; and (iii) detecting the presence of the barcode in the target nucleic acid or copy thereof.

A method for determining the location of a non-canonical feature in a target nucleic acid at a single base resolution, the method comprising: (i) contacting the target nucleic acid with a nucleic acid-binding molecule as described herein; (ii) transferring the nucleic acid barcode to the target nucleic acids to generate a barcoded target nucleic acid, in an environment that substantially prevents off-target generation of barcoded nucleic acids; and (iii) detecting the presence of the barcode in the target nucleic acid or copy thereof; wherein the nucleic acid-binding molecule comprises a binding domain capable of one or more of the following: inducing a mutation in the target nucleic acid; or preventing polymerase bypass and therefore causing truncation during copying of the target nucleic acid. In some embodiments, steps (i)-(iii) are repeated at least once. In some embodiments, a different nucleic acid-binding molecule is used each time steps (i)-(iii) are repeated. In some embodiments, the same nucleic acid-binding molecule is used each time steps (i)-(iii) are repeated.

The methods described herein may be used to diagnose a disease, disorder, or condition. For example, in some embodiments, the methods may be used to diagnose cancer in a subject in need thereof. In some embodiments, the kits may be used to monitor a disease, disorder, or condition over time, such as in response to one or more treatments. For example, the kits may be used to monitor epigenetic and/or epitranscriptomic changes over time in a subject undergoing treatment for cancer (i.e., chemotherapy, radiation, etc.) In some embodiments, the methods may be used to analyze a cell or tissue from a subject in need thereof. For example, the methods may be used to detect non-canonical features in a cell or tissue isolated from a blood sample, a biopsy sample, an autopsy sample, etc.

In some embodiments, the methods may be used to detect and/or monitor epigenetic changes in cells used commercially for production of one or more products, such as cells used for industrial fermentation. In some embodiments, the methods may be used to detect and/or monitor epigenetic changes in a plant cell or tissue.

Compositions Comprising Nucleic Acid-Binding Molecules

Also provided herein are compositions comprising one or more nucleic acid-binding molecules of the disclosure. In some embodiments, a composition comprises one or more types of nucleic acid-binding molecules. For example, the composition may comprise a first nucleic acid-binding molecule that binds to a first non-canonical feature, and a second nucleic acid-binding molecule that binds to a second non-canonical feature. In some embodiments, the composition may comprise 1, 2, 3, 4, 5, 6, 7, 8, 9, 10, 11, 12, 13, 14, 15, 16, 17, 18, 19, 20, 21, 22, 23, 24, or 25, or more different types of nucleic acid-binding molecules.

Also provided herein are compositions comprising one or more complexes, wherein each complex comprises a nucleic acid-binding molecule bound to a target nucleic acid.

In some embodiments, the compositions described herein comprise one or more carriers, excipients, buffers, etc. The compositions may have a pH of about 0.5, about 1.0, about 1.5, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 9.5, about 10.0, about 10.5, about 11.0, about 11.5, about 12.0, about 12.5, about 13.0, about 13.5, or about 14.0. In some embodiments, the compositions are pharmaceutical compositions.

Kits for Analyzing Nucleic Acids

The nucleic acid-binding molecules described herein can be provided in a kit (e.g., as a component of a kit). For example, the kit may comprise a nucleic acid-binding molecule, or one or more components thereof, and informational material. The informational material can be, for example, explanatory material, instructional material, sales material, or other material regarding the methods described herein and/or the use of the nucleic acid-binding molecule. The informational material of the kit is not limited in form. In some embodiments, the informational material may include information regarding the production of the nucleic acid-binding molecule, molecular weight, concentration, expiration date, batch or production site information, and the like. In some embodiments, the information material may comprise a list of disorders and/or conditions that may be diagnosed or evaluated using the kit.

In some embodiments, the nucleic acid-binding molecule may be provided in a suitable manner (e.g., in an easy-to-use tube, at a suitable concentration, etc.) for use in the methods described herein. In some embodiments, the kit may require some preparation or manipulation of the nucleic acid-binding molecule before use. In some embodiments, the nucleic acid-binding molecule is provided in a liquid, dried, or lyophilized form. In some embodiments, the nucleic acid-binding molecule is provided in an aqueous solution. In some embodiments, the nucleic acid-binding molecule is provided in a sterile, nuclease-free solution. In some embodiments, the nucleic acid-binding molecule is provided in a composition that is substantially free from any nucleic acids besides those that may comprise the molecule itself.

In some embodiments, the kit may comprise one or more syringes, tubes, ampoules, foil packages, or blister packs. The container of the kit can be airtight, waterproof (i.e., to prevent changes in moisture or evaporation), and/or comprise light shielding.

In some embodiments, the kit may be used to perform one or more of the methods described herein, such a method for analyzing a population of target nucleic acids. In some embodiments, the kit may be used to diagnose a disease, disorder, or condition. For example, in some embodiments, the kit may be used to diagnose cancer. In some embodiments, the kit may be used to monitor a disease, disorder, or condition over time, such as in response to one or more treatments. For example, the kit may be used to monitor epigenetic and/or epitranscriptomic changes over time in a subject undergoing treatment for cancer.

EXAMPLES

The following non-limiting examples further illustrate embodiments of the compositions and methods of the instant disclosure.

Example 1: Binding Domain Design, Selection, and Characterization

Binding domains are designed for use in nucleic acid-binding molecules (also referred to as BACs (=binding domain adapter conjugates) that bind to N6-methyladenosine (m6A), pseudouridine (Ψ), Inosine (I) and 5-methylcytosine (m5C). Initially, a screen of commercially-available antibodies was performed. Antibodies having favorable characteristics (e.g., monoclonals, etc.) are selected for further characterization.

Initial antibody characterization was carried out by plate ELISA. Biotinylated RNA oligonucleotides (Horizon Discovery) comprising m6A (SEQ ID NO: 1), Ψ (SEQ ID NO: 2), I (SEQ ID NO: 3) or m5C (SEQ ID NO: 4) and unmodified reference oligonucleotides (SEQ ID NO: 5) as shown in Table 4 were immobilized on streptavidin-coated 96-well plates (Thermo Fisher, cat. no. 15125) at 4° C., followed by washing with phosphate-buffered saline (PBS). In a separate experiment, the oligonucleotides are converted into RNA/DNA heteroduplexes by reverse transcription (Protoscript II, NEB cat. no. M0368L) to evaluate the antibody's ability to bind RNA modifications in the context of a duplex. Because RNA sequences adopt stable secondary structures, the presentation of RNA modifications is often in a duplex and antibodies that recognize modifications independent of their base pairing status are considered superior. Antibodies were added to the plates and incubated for 60 min at 22° C. Unbound antibody was washed away, and an alkaline phosphatase (AP)-conjugated detection antibody was added (Thermo Fisher, cat. no 31430 and 31460). After unbound detection antibody was washed away, an AP substrate was added to the plate (Thermo Fisher, cat. no. 34028), and absorbance detection at 450 nm was used to determine the presence of bound antibodies.

TABLE 4

Biotinylated RNA oligonucleotides

| Description | Sequence | SEQ ID NO |
|---|---|---|
| Biotinylated RNA oligonucleotide comprising m6A | 5'-biotin-rNrNrNrNrNrNrNrN(m6A)rNrNrNrNrNrNrNrN | 1 |
| Biotinylated RNA oligonucleotide comprising I | 5'-biotin-rNrNrNrNrNrNrNrN (I) rNrNrNrNrNrNrNrN | 2 |
| Biotinylated RNA oligonucleotide comprising Ψ | 5'-biotin-rNrNrNrNrNrNrNrN (Y) rNrNrNrNrNrNrNrN | 3 |
| Biotinylated RNA oligonucleotide comprising m5C | 5'-biotin-rNrNrNrNrNrNrNrN (m5C) rNrNrNrNrNrNrN | 4 |
| Unmodified reference oligonucleotide | 5'-biotin-rNrNrNrNrNrNrNrNrNrNrNrNrNrNrNrN | 5 |

*wherein "N" represents any nucleotide and "r" represents ribonucleotides.

Figure 19:
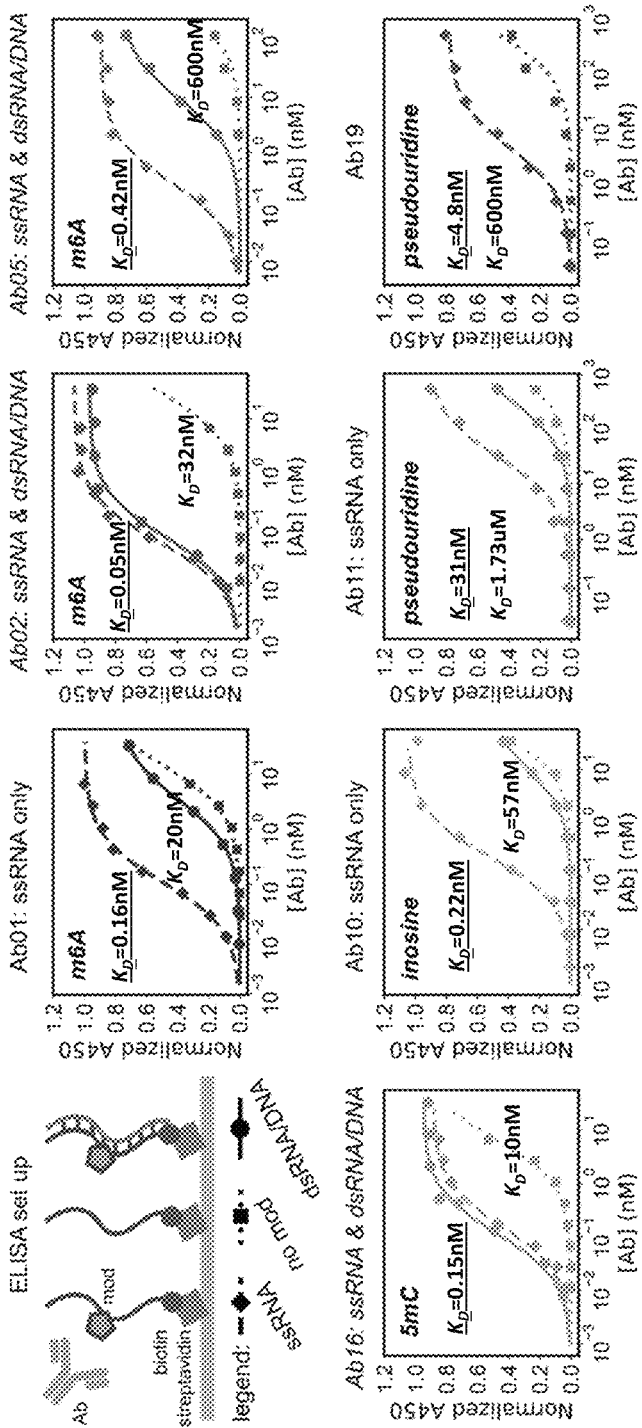
FIG. 19 provides binding curves for several exemplary RNA modification specific antibodies and their targets, as obtained by ELISA. Biotinylated RNA targets are immobilized at high density on streptavidin plates and antibodies are allowed to bind at a range of concentrations. The binding curves are fitted with a 1:1 binding model to derive the dissociation constant ($K_D$). The RNA targets are either single stranded (ss-RNA) or double-stranded RNA/DNA heteroduplexes (dsRNA/DNA) containing a single modification flanked by degenerate sequences. An unmodified, degenerate sequence serves as a negative control (no mod). Ab01 through Ab19 are antibody IDs; the antibody sources are provided in Example 1. Antibodies bind with high affinity and specificity to their RNA targets.

The affinity of antibody binding was evaluated by titrating the amount of antibody used in the assay and fitting the resulting curves to a binding model. FIG. 19 shows binding curves for a subset of antibodies with favorable binding properties for m6A (Thermo Fisher, cat. no. 61755 (Ab01)), MA5-33030 (Ab02), Synaptic Systems cat. no. 345E11 (Ab05)), m5C (Thermo Fisher, cat. no. MA5-24694 (Ab16), I (Diagenode, cat. no. C15200251 (Ab10)) and Ψ (Diagenode, cat. no. C15200247 (Ab11), MBL, cat. no. D347-3 (Ab19)). All but the pseudouridine antibodies bound their cognate antigen in single-stranded RNA with subnanomolar dissociation constant $K_D$ (a measure of affinity) and larger than 100-fold specificity. The pseudouridine antibodies had only a nanomolar affinity with about 10-fold specificity. Ab02, Ab05 and Ab16 were particularly desirable as they exhibited strong binding to RNA/DNA heteroduplexes. The dissociation constants derived from this ELISA format are the results of avidity, because of the high density of RNA strands on the surface both antibody arms can bind to a modified base. This bidentate binding mode is known to slow dissociation rates, increasing overall affinity. Based on the data presented herein, it is expected that the affinity in a single molecule 1:1 complex will be lower. Ab05, Ab10, Ab16 and Ab19 were selected for further analysis.

Example 2: Determining Binding Domain Mutational Profile and Truncation Pattern

The mutational profile and truncation pattern will be characterized for either (1) the antibodies identified in Example 1, or (2) derivatives thereof (e.g., scFvs comprising CDR sequences from the antibodies of Example 1). Specifically, binding domains, such as those described in Example 1 are bound to a nucleic acid target. The binding domain and nucleotide are crosslinked. After the target nucleotide is adapter-ligated, reverse transcription is used to generate cDNA which are PCR amplified and sequences to assess the mutational and truncation profile of the target nucleotide.

Initially, the mutational pattern that results from reverse transcription of antibody-bound RNA strands is evaluated with in vitro transcribed RNA. First, RNAs including one or more modifications (m6A, Ψ, and/or m5C) are generated by transcribing a 500 nucleotide RNA in vitro in the presence of varying ratios of modified and unmodified nucleotide triphosphate (NTP) (TriLink) using the AmpliScribe™ T7 High Yield Transcription Kit (Lucigen). The transcripts are fragmented to a size of 50 to 150 nucleotides using an RNA fragmentation reagent (Thermo) and incubated with each candidate antibody.

To determine if UV cross-linking induces truncation of reverse transcription at the modification site, each antibody-RNA complex solution is irradiated with UV light (e.g., about 0.15 J/cm$^2$, 254 nm). After cross-linking, antibody-RNA complexes are captured on protein A/G Dynabeads (Thermo) by incubating the irradiated solutions with the beads at 4° C. for 1-2 h. Protein A/G binds the Fc region of antibodies with high affinity. Afterwards, the 3' ends of the RNA are dephosphorylated with polynucleotide kinase (NEB) and DNA adapters are ligated thereto with T4 RNA ligase (NEB). The adapter is pre-adenylated at the 5' end: 5rApp/AGATCGGAAGAGCGGTTCAG/3ddC, wherein 5rApp refers to 5' preadenylation, and 3ddc refers to 3' dideoxy-C(SEQ ID NO: 6).

Adapter-ligated RNA is eluted from the beads, purified and primed with an oligonucleotide that is complementary to the ligated adapter (i.e., a reverse transcriptase primer). The reverse transcriptase primer is 5'phosphorylated to enable circularization downstream and contains a 4 letter barcode framed by degenerate bases, a BamHI restriction site (gatc, SEQ ID NO:7) and forward and reverse primer binding sites: 5'P-NNAACCNNNAGATCGGAAGAGCGTCGTG-gatcCTGAACCGC-3' (SEQ ID NO: 8).

Reverse transcription is performed to produce cDNA. The reverse transcription is performed using a panel of reverse transcriptases including, for example, Superscript III (Thermo), to allow comparison of each enzyme's mutational and truncation patterns. After size selection of cDNA with AMPure beads (Agencourt), cDNA is circularized with CircLigase II (Lucigen) at 60° C. and cleaved with a BamHI restriction enzyme. Libraries are PCR amplified with suitable sequencing adapters and sequenced on a MiSeq instrument (Illumina). The reads are aligned against the reference RNA sequence, and mutational and truncation patterns are assessed.

Example 3: Preparation of Nucleic Acid-Binding Molecules Using Random Labeling of Binding Domains Nucleic acid-binding molecules were prepared by conjugating DNA oligonucleotides to the antibodies described in Example 1 via amine reactive chemistry. Amino-modified DNA oligonucleotides were randomly attached to antibodies using an Oligonucleotide Conjugation Kit (Vector Labs, cat. no. S-9011-1). The first step was the modification of amino-terminated DNA oligonucleotides with the 4FB crosslinker and the modification of the antibody's lysine residues with HyNic reagent. Simple mixing of activated oligonucleotides and antibodies lead to covalent bond formation between them.

Figure 20A:
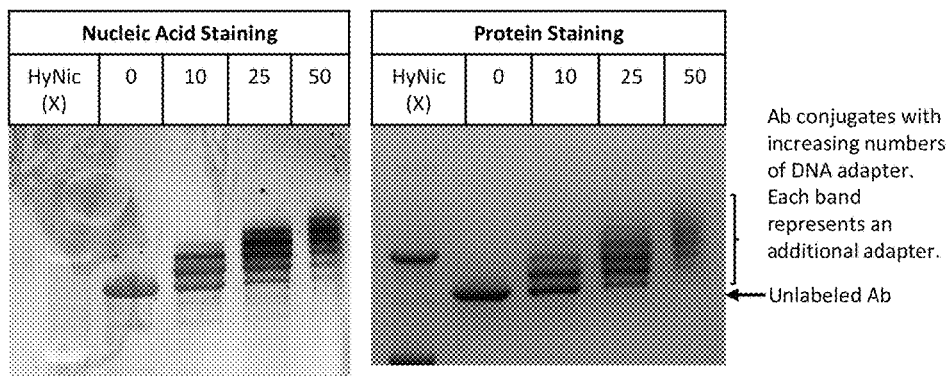
FIGS. 20A and 20B show experimental data for generating nucleic acid binding molecules. RNA modification specific antibodies are random labeled with DNA adapters using HyNic (Hydrazino-nicotin-amide) chemistry.

The stoichiometry of labeling was assessed by SDS gel electrophoresis and function was confirmed by plate ELISA as described in Example 1. FIG. 20A shows how the efficiency of oligonucleotide labeling of Ab01 changed in response to the HyNic concentration (i.e., 0, 10, 25, or 50-fold molar excess). At a 10-fold molar excess of HyNic, antibody conjugates with 0, 1 or 2 oligonucleotides were present, whereas the number of oligonucleotides ranged from 1 to 7 at a 50-fold excess of HyNic.

Figure 20B:
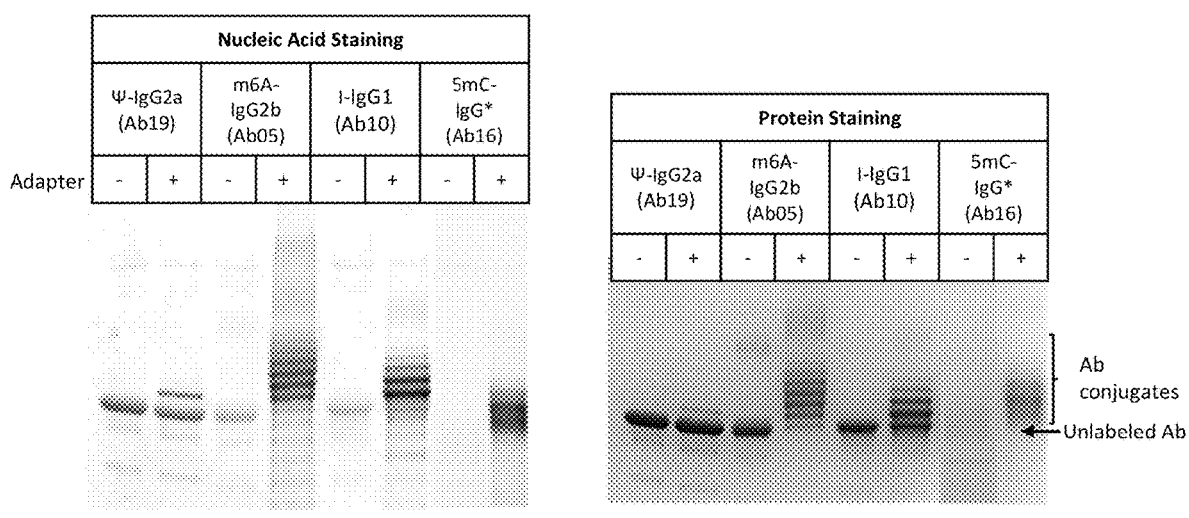

For use in barcoding assays, a HyNic concentration is preferred that minimizes the amount of unlabeled antibody while avoiding labeling lysine residues that are important for function. In practice, the optimal HyNic ratio depended on the IgG isotype and the sequence of the paratope (FIG. 20B). Ab05 exhibited up to eight oligonucleotides per antibody, Ab10 up to five, Ab16 up to three and Ab19 up to 1. The adapter used for all labeling reactions in FIG. 20B was the same and was designed for barcoding by primer extension (Type 2D adapter) and comprises a PEG linker (iSp18), a blocked 3' end (3SpC3) and a 5' amine (5AmMC6) for conjugation to the binding domain (/5AmMC6/T/iSp18/ TATAAG AGACAGACACAGGCCACTCAGTCTAT/ 3SpC3/; SEQ ID NO: 9). Adapters for barcoding by primer extension and general use in sequencing have the following architecture: /5AmMC6/T/iSp18/ AGACGTGTGCTCTTCCGATCTNNN<u>ACTAATT-CACTCAGT</u>/3 SpC3/; SEQ ID NO: 56 (5AmMC6=5'amine, iSp18=PEG linker, cursive=Illumina adapter, NNN=UMI, underlined=7b MBC (modification-encoding barcode), bold=8b spacer, 3SpC3=3' blocking group). PEG linkers add spatial flexibility for efficient barcode transfer. Oligonucleotide sequences, possible terminal modifications and the orientation of tethering may be altered based on the specific needs of each nucleic-acid binding molecule.

ELISA experiments as described in Example 1 were used to confirm antibody binding activity after labeling with oligonucleotides. Comparing the binding curves of the same antibody before and after labeling showed that Ab05, Ab16 and Ab10 all lost some activity, with Ab05 being the worst hit with a >15-fold loss of $K_D$ (FIGS. 21A-21C). However, these experiments demonstrate detectable binding of antibodies as binding domains for use in identifying nucleotide modifications.

Example 4: Preparation of Nucleic Acid-Binding Molecules Using Site-Specific Labeling of the Carbohydrate Domains of Antibodies To avoid impairment of binding activity, Ab05 was site-specifically labeled using a SiteClick Antibody Azido Modification Kit (Thermo Fisher, cat. no. S20026). SiteClick labeling uses enzymes to specifically attach an azido moiety to the heavy chains of an IgG antibody, ensuring that the antigen binding domains remain unaltered for binding to the antigen target. This site selectivity was achieved by targeting the carbohydrate domains present on essentially all IgG antibodies regardless of isotype and host species. β-galactosidase catalyzes the hydrolysis of a β-1,4 linked D-galactopyranosyl residue followed by the attachment of an azido-galactopyranosyl using an engineered β-1,4-galactosyltransferase. Once azido-modified, a DBCO (Dibenzocyclooctyl) labeled adapter (e.g. DBCO/5AmMC6/T/iSp18/TATAAGA GAC AGACACAGGC-CACTCAGTCTAT/3SpC3/; SEQ ID NO:22) was conjugated to the Fc region resulting in antibodies that exhibited one or two adapters, but also some unlabeled antibody (FIG. 21D). An ELISA assay confirmed unaltered binding affinity of the site-specifically labeled antibody (FIG. 21E).

Example 5: Preparation of Nucleic Acid-Binding Molecules Using Site-Specific Labeling by Genetic Engineering, and Immobilization Thereof on a Bead When the nucleic acid-binding molecules are used in bead-based assays, the molecules are immobilized on a surface in an orientation that maintains binding activity. To prepare nucleic acid-binding molecules reproducibly for use in such assays, site-specific labeling of the binding domains (e.g., antibodies or fragments thereof) is used. The method below can be adapted to any protein binding domain and is not limited to antibodies.

Initially, antibodies are engineered as follows. The Spytag peptide (AHIVMVDAYKPTK, SEQ ID NO: 10) is fused to the C-terminus of the antibody heavy chain. The C-terminus of the antibody light chain is modified with the short peptide, LCxPxR wherein x can be any amino acid (SEQ ID NO: 11). This peptide is the substrate of formyl glycine generating enzyme (FGE). Thus, the antibody is expressed and purified with two peptide fusion tags (FIG. 17C).

A bacterial expression system is chosen that expresses FGE. The enzyme introduces a formyl glycine co-translationally. The aldehyde group of the formyl glycine is a reactive chemical handle that is used for attaching amino-DNA after converting the amino group to an oxime or hydrazone.

To immobilize the nucleic acid-binding molecule on a bead, a bead is decorated with Spycatcher protein. The N-terminus of Spycatcher reacts quickly and completely with the C-terminal Spytag displayed by the binding domain of the nucleic acid-binding molecule, thereby forming a covalent isopeptide bond. Native Spycatcher is a 139 amino acid protein and is cysteine-free: msyyhhhhhh dydipttenl yfqgamvdtl sglsseqgqs gdmtieedsa thikfskrde dgkelagatm elrdssgkti stwisdgqvk dfylypgkyt fvetaapdgy evataitftv neqgqvtvng katkgdahi (SEQ ID NO: 12). A single cysteine mutation is introduced at the C-terminus to allow surface coupling via maleimide chemistry (see Example 9).

Example 6: Immobilization of Nucleic Acid Binding Molecules on Protein G Beads and Nucleic Acid Target Pulldown The simplest assay format for the multiplexed detection of nucleic acid modifications is shown in FIG. 5A. Beads are loaded with only one type of nucleic acid binding molecule, representing a "bead type". To interrogate several nucleic acid modifications simultaneously several bead types are combined and mixed with the nucleic acid targets. Because all nucleic acid binding molecules of a bead type immunoprecipitate the same target their surface density does not need to be tightly controlled. A target that is bound to one nucleic acid binding domain but is barcoded by a neighboring nucleic acid binding molecule will be correctly identified.

A universal method for immobilizing IgG antibodies is the use of commercial protein G beads. Protein G is an immunoglobulin-binding protein expressed in group C and G Streptococcal bacteria. It is a 65-kDa (G148 protein G) and a 58 kDa (C40 protein G) cell surface protein that binds to the Fab and Fc region of most IgG isotype. This example describes the immobilization of randomly adapter-labeled nucleic acid binding molecules on protein G beads and the specific pulldown of modified RNA sequences.

Figure 22:
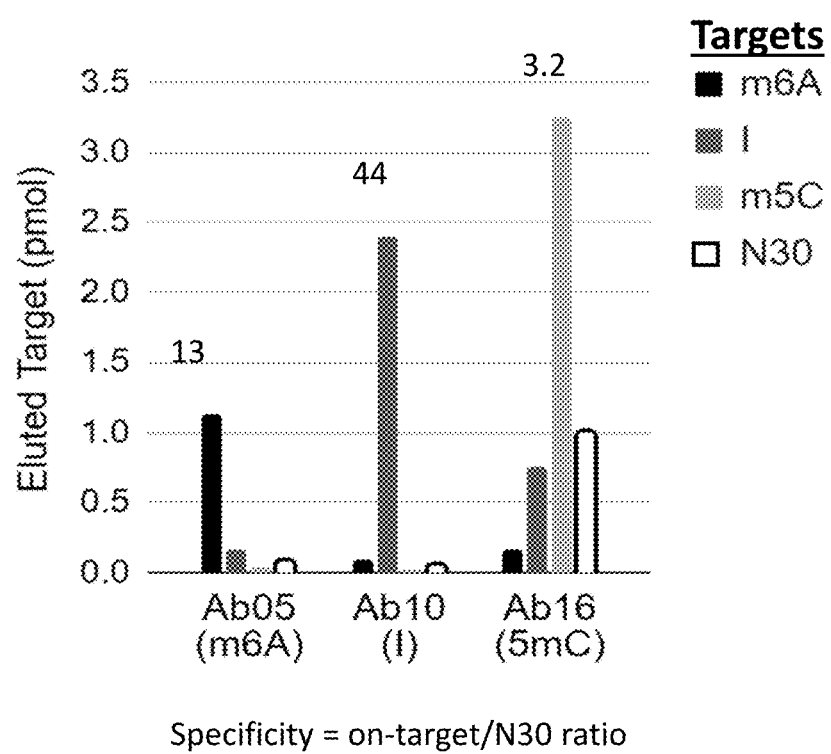
FIG. 22 shows experimental data for the pulldown of modified or unmodified (N30) RNA targets by different antibodies. In this experiment, antibodies are immobilized on protein G beads and incubated with a mixture of four different RNA targets. Each antibody prefers its target, with specificities ranging from 3 to 44 relative to the N30 control. Specificity is sequence dependent.

Unlabeled antibodies for m6A (Ab05), m5C (Ab16) and I (Ab10) were loaded onto magnetic protein G Dynabeads (Thermo Fisher, cat. no. 10009D). 50 μL of Dynabeads were washed and incubated with 200 μL of antibody (0.05 μg/μL) in PBST (PBS with 0.1% Tween® 20 detergent). The antibodies were allowed to bind for 20 min at 22° C., followed by washing of the beads with 200 μL of PBST. The loaded beads were exposed to a mixture of synthetic RNA targets for 1 hour at 22° C., each target exhibiting a single modification (m6A (SEQ ID NO: 13), m5C (SEQ ID NO: 18), I (inosine) (SEQ ID NO: 16), or no modification as shown in Table 5. The targets were 5' modified with fluorescein (FAM) to enable ratiometric detection on a gel. After washing with PBST the immunoprecipitated RNA was recovered by incubation with 2×TBU sample loading buffer (Thermo Fisher, cat. no. LC6876) for 2 min at 70° C. The targets are separated on 15% TBU gels (Thermo Fisher, cat. no. EC62755BOX) and quantitated (FIG. 22). All antibodies showed a clear preference for their cognate target, at varying levels of specificity. The latter was equal or higher than 10-fold for most antibody-target combinations, which was lower than predicted by the ELISA measurement (Example 1). This finding was attributed to the absence of avidity in the inverted format where the antibody is immobilized rather than the RNA target, and to differences in the stringency of the washing procedure.

TABLE 5

Synthetic RNA targets

| Description | Sequence | SEQ ID NO |
|---|---|---|
| Synthetic RNA target comprising m6A modification | 5'-FAMrUrCrGrUrCrGrGrCrArGrCrGrUrCrArGrArUrGrCrArUrAr ArGrGrUrCr(m6A)rArUrArArUrUrArArGrUrArUrArGACTGAGTG | 13 |
| Synthetic RNA target comprising m5C modification | 5'-FAM- rCrGrUrCrGrCrArGrCrGrUrCrArGrArUrGrArUrArUrUr (m5C)rGrAr ArGrUrArUrGrArC | 18 |
| Synthetic DNA target comprising I modification | 5'-FAM- TCGTCGGCAGCGTCAGATGATACT(I)GCAGTATACTGAGTG | 16 |

*Wherein "r" represents ribonucleotides.

Example 7: Enabling Barcoding of a Random Pool of RNA Sequences by Primer Extension Barcoding by primer extension requires the presence of a rationally designed sequence (spacer, SP; see FIGS. 2D and 3D) at the 3' end of the target RNA. An adapter for barcoding by primer extension contains a sequence complementary to the spacer. Hybridization of the adapter to the target spacer forms a recessed 3'end that can be extended by DNA polymerases or reverse transcriptases, thus copying the barcode sequence to the target RNA. The following example provides methods for tagging a random pool of RNA sequences with a spacer, using a tailing or a ligation reaction (FIG. 23A).

Figure 23B:
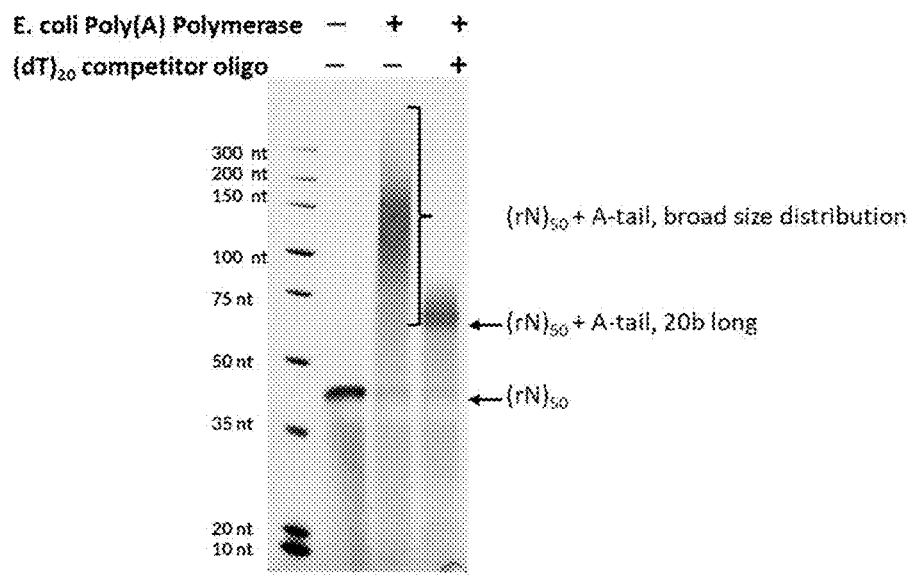
Figure 23C:
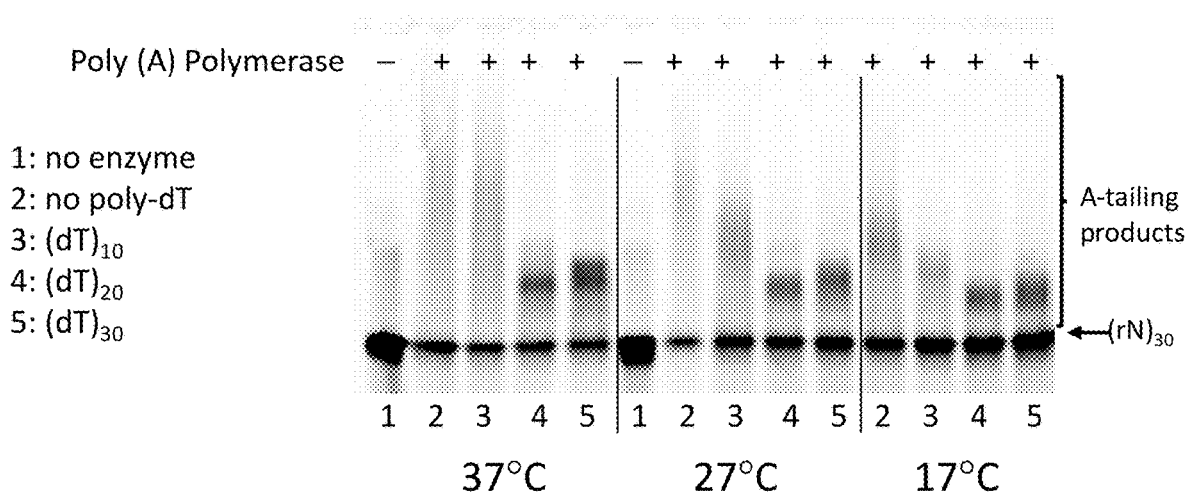

The first method appended a 3'poly-rA tail to the RNA target. Degenerate 30b RNA sequences ($rN_{30}$) were polyadenylated using *E. coli* poly (A) polymerase (NEB, cat. no. M0276L) in the presence of 1 mM ATP. The number of A's added to a pool of random 30b RNA molecules (5'-FAM-$(rN)_{30}$; SEQ ID NO: 23) has a broad Gaussian distribution with a mean around 150b. Control over the size of the A-tail was obtained by adding an excess of competitor poly(dT) oligonucleotide of the desired length to the reaction. The competitor bound to the nascent A-tail and displaced the polymerase, thus aborting the reaction. FIG. 23B depicts the generation of a 20b spacer by adding a poly(dT)$_{20}$ oligonucleotide to the tailing reaction. FIG. 23C depicts the generation of a 10, 20 and 30b spacer by adding poly(dT) oligonucleotides of the corresponding lengths to the tailing reactions and explored the effect of temperature. The 20 and 30b poly(dT) competitors produced the desired spacer lengths, however, the 10b competitor failed to control the spacer length. This is likely because a 10b A/T duplex is not stable at the tested reaction temperatures. Shorter homopolymer tails can be produced using poly (U) polymerase in the presence of GTP or CTP and the complementary 10b competitor oligonucleotide. The approach is extendable to any spacer length that allows for hybridization of the competitor to the homopolymer-tail at a given reaction temperature.

Messenger RNA (mRNA) naturally includes 3'-A-tails and these tails are widely exploited for selectively hybridizing mRNA molecules to immobilized poly-dT probes. Aside from providing a method for spacer attachment, any RNA population can be A-tailed with this method and immobilized on beads by hybridization according to FIG. 4B.

Figure 23D:
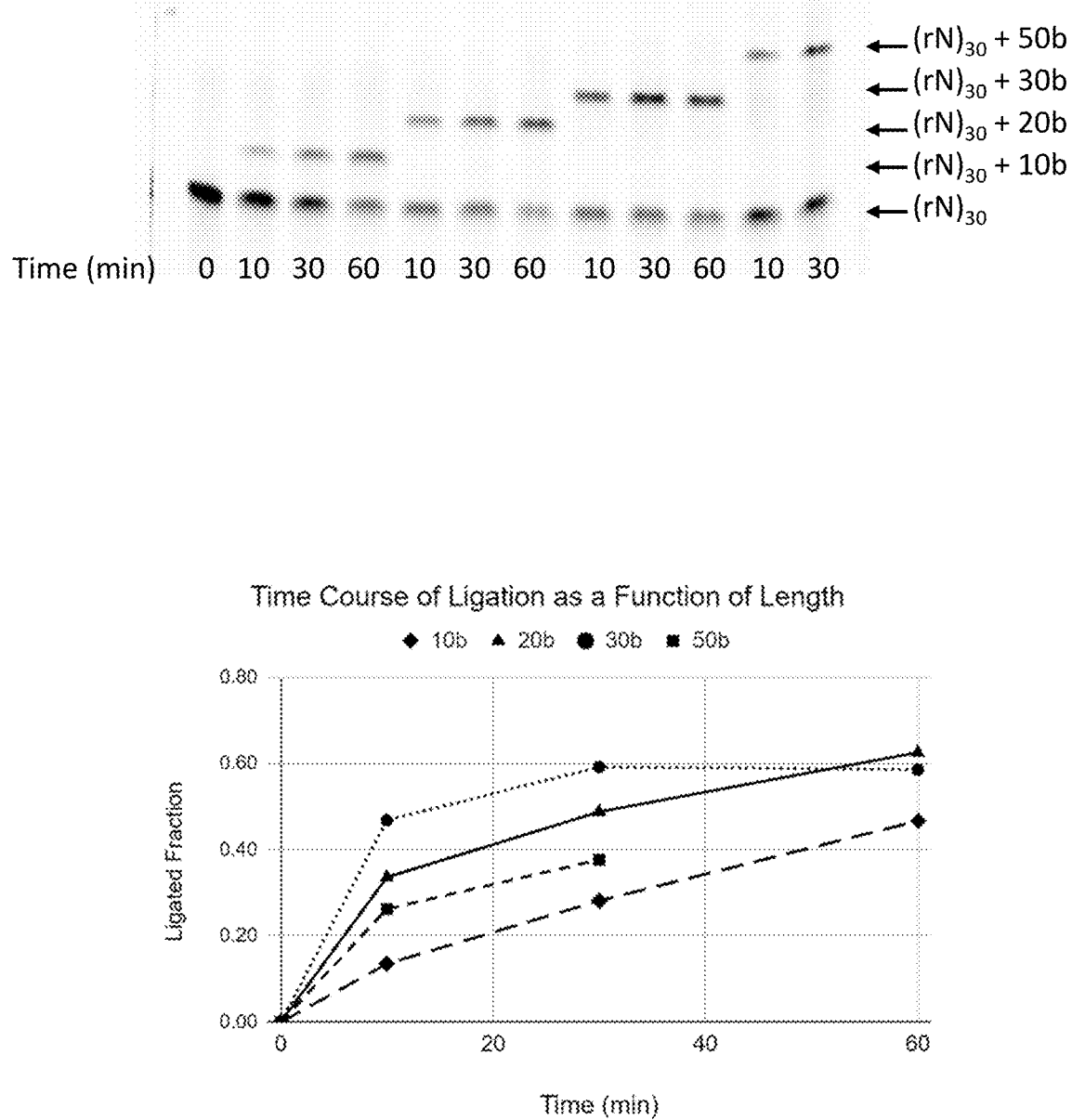

The second method used enzymatic ligation. Spacers comprising any base sequence were introduced by 3' ligation catalyzed by T4 RNA ligase I (NEB, cat. no. M0204L). The reaction required a dephosphorylated 3' end of RNA and a 5'-phosphorylated DNA spacer. FIG. 23D shows the ligation of 5'-phosphorylated DNA sequences, ranging in sizes of 10, 20, 30, and 50b (SEQ ID NOs: 28-31, respectively see Table 6) to a 30b degenerate RNA library (SEQ ID NOs: 23). The size range was chosen to provide useful information for introducing a spacer (typical spacer sizes are ~10b) and for barcoding by ligation according to FIG. 3A (typical adapter sizes are >25b). The standard conditions for ligating a spacer or adapter are the same: reactions were incubated for 1 hour at room temperature using an optimized ligation buffer (500 nM RNA target, 2.5 µM 5'phosphorylated DNA, 50 mM Tris pH 7.5, 10 mM $MgCl_2$, 1 mM DTT, 0.5 mM ATP, 20% PEG-8000 and 0.5 units/µL T4 RNA ligase I). Ligation products were analyzed by denaturing gel electrophoresis. Quantification of the gel indicated that the reaction proceeded fastest for DNA sequences of medium length (20 and 30b) and slowed for very short (10b) and longer (50b) sequences (FIG. 23D). Therefore, a typical spacer ligation was performed overnight to maximize the conversion and adapters for barcoding by the same ligation reaction were designed to not exceed 50b.

A nucleic acid binding molecule exhibiting an adapter for barcoding by primer extension contacts the target RNA specifically via the non-canonical feature and non-specifically via the spacer. Compared to barcoding by ligation, the binding mode changes from monovalent to bivalent, thus adding engineered avidity. While this is an opportunity for increasing binding affinity, the design bears the risk of decreasing binding specificity. To avoid a negative impact to specificity, the spacer interaction needs to be so weak that it is unsustainable in the absence of the non-canonical feature. Thus, the spacer should be as short as possible but long enough to enable binding of a polymerase and to effectively compete with intramolecular secondary structures formed particularly by RNA.

Figures 23E, 23F:
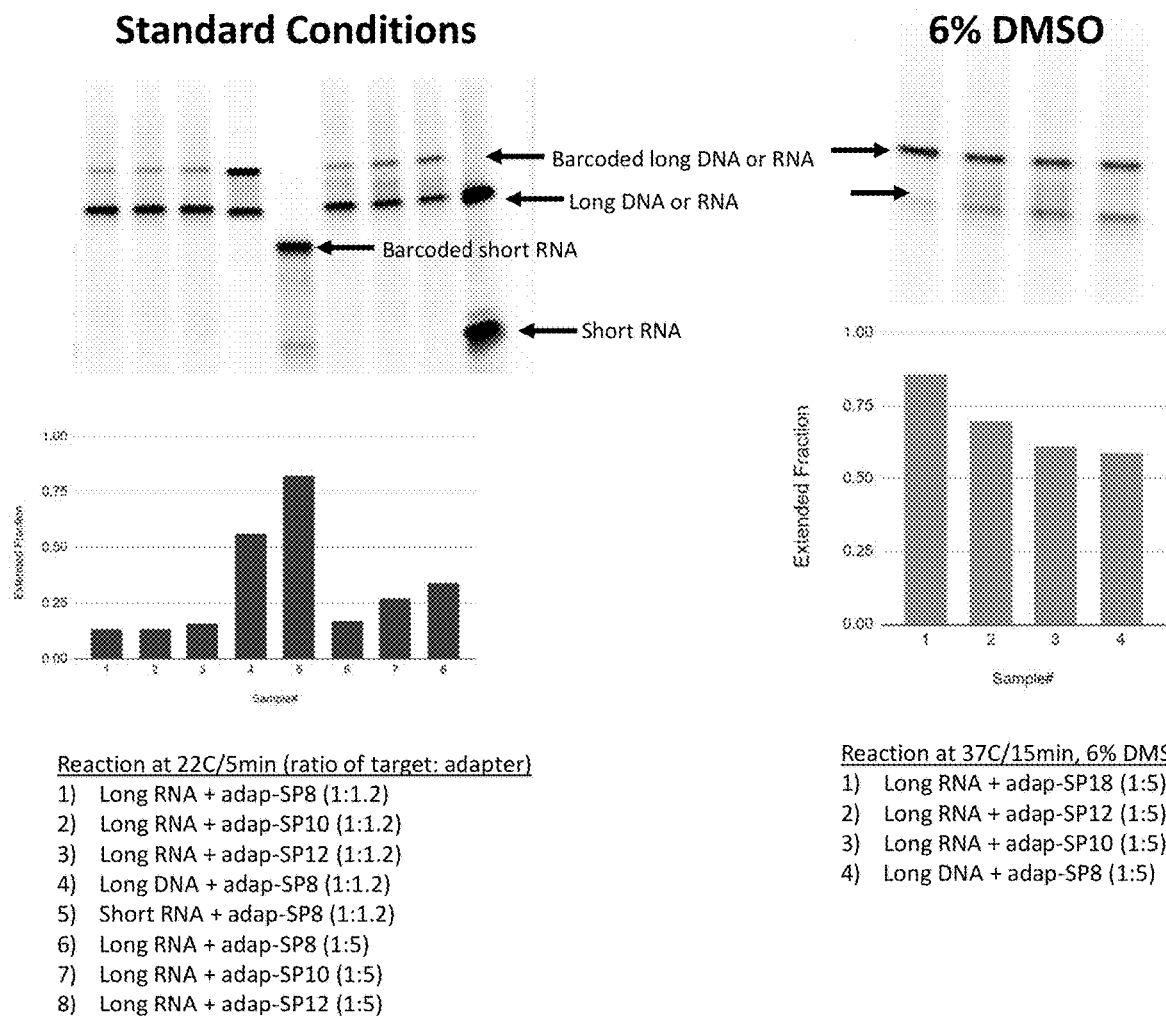
FIGS. 23E-23F provide experimental examples for barcoding by primer extension in the absence of a nucleic acid binding molecule. The experiments are designed to examine the effect of the length the spacer (c.f. universal sequence), secondary structure of the target nucleic acid and the reaction conditions on the completeness of barcoding.

The impact of spacer length on primer extension in the absence of a nucleic acid binding molecule (aka synthesizing the complement of a free adapter) is depicted in FIG. 23E, using a 50b RNA sequence of typical structural complexity (SEQ ID NO: 13). A 50b DNA target (SEQ ID NO: 15) and an 18b RNA target (SEQ ID NO: 24) as shown in Table 6 were tested in parallel to determine differences possibly arising from structural complexity. All targets exhibited a 3' DNA spacer of the sequence ACTGAGTG (SEQ ID NO: 19). The adapters, applied in solution at a 1- or 5-fold excess over target, comprised an 8, 10, or 12-b complementary spacer (SEQ ID NOs: 25-27, and 38 as by the nucleic acid binding molecule. Here, antigen recognition by the binding domain fixes the adapters in direct proximity of the RNA target, causing a high local centration of adapter and an acceleration of enzymatic reactions consequently ("proximity effect").

TABLE 6

Adapters and Synthetic targets

| Description | Sequence | SEQ ID NO |
|---|---|---|
| Synthetic RNA target comprising m6A modification | 5'-FAMrUrCrGrUrCrGrGrCrArGrCrGrUrCrArGrArUrGrCrArUrArArGrGrUrCr(m6A)rArUrArUrUrArArGrUrArUrArGACTGAGTG | 13 |
| Synthetic DNA target comprising m5C modification | (5'FAM-TCGTCGGCAGCGTCAGATGCATAATCTA(m5C)ATCTTAAGTATAGACTGAGTG | 15 |
| 18base RNA target | 5'-FAM-rUrUrArArGrUrArUrArGACTGAGTG | 24 |
| Adapter (8 base spacer) | /5AmMC6/T/iSp18/TATAAGAGACAGACACAGGCCACTCAGT | 25 |
| Adapter (10 base spacer) | /5AmMC6/T/iSp18/TATAAGAGACAGACACAGGCCACTCAGTCT | 26 |
| Adapter (12 base spacer) | /5AmMC6/T/iSp18/TATAAGAGACAGACACAGGCCACTCAGTCTAT | 27 |
| Adapter (18 base spacer) | /5AmMC6/T/iSp18/TATAAGAGACAGACACAGGCCACTCAGTCTATACTTAA | 38 |
| 5'-phosphorylated DNA sequences | /5Phos/NNACTGAGT/3ddC/ | 28 |
| 5'-phosphorylated DNA sequences | /5Phos/NNACTGAGTGGCCTGTGTC/3ddC/ | 29 |
| 5'-phosphorylated DNA sequences | /5Phos/NNACTGAGTGGCCTGTGTCTGTCTCTTAT/3ddC/ | 30 |
| 5'-phosphorylated DNA sequences | /5Phos/NNACTGAGTGGCCTGTGTCTGTCTCTTATACACATCTCCGAGCCCACGAGA/3ddC/ | 31 |

Modifications are abbreviated according to the syntax used by Integrated DNA Technologies.
5AmMC6 = 5' amine,
iSp18 = PEG linker,
5Phos = 5' phosphate,
3ddC = dideoxycytidine shown in Table 5). A typical primer extension reaction contained 10 mM Tris pH 7.9, 2 mM MgCl$_2$, 100 uM dNTP, 0.1% Tween-20, 1 μM target, 1 or 5 μM adapter, and 0.25 units/μL Klenow Fragment (3'→5' exo-), and optionally 6% DMSO. The standard reaction condition was primer extension for 5 min at 22° C. The data showed that the long RNA extended poorly compared to DNA and short RNA target, regardless of spacer length. At conditions that destabilize intramolecular secondary structure, such as elevated temperature (5 min at 37 C), the presence of DMSO, and a higher adapter concentration (5-fold excess over target), longer spacers were advantageous (FIG. 23F). This finding suggests that spacer access is hindered by RNA secondary structures and even 12b spacers cannot easily invade stable RNA secondary structures unless the structures are destabilized by additional measures. Example 8 below demonstrates that primer extension is more facile when mediated Example 8: Barcode Transfer to Immunoprecipitated RNA This example is an extension of Example 6 where randomly adapter labeled antibodies were loaded onto protein G beads instead of unlabeled antibodies, and barcode transfer to immunoprecipitated nucleic acid targets was induced by primer extension or ligation.

Protein G beads were individually loaded with m6A nucleic acid binding molecules (Ab05 with 8b or 12b spacer primer extension adapter), m5C nucleic acid binding molecules (Ab16 with 8b spacer primer extension adapter) or I nucleic acid binding molecules (Ab10 with Ab05 with 8b or 12b spacer primer extension adapter).

Each loaded bead type was incubated with a mixture of two RNA or DNA targets. The Ab05 and Ab16 beads were incubated with m6A and m5C RNA targets (SEQ ID NOs:

13 & 14) shown in Table 7. The Ab10 beads were incubated with m5C and I DNA targets (SEQ ID NOs: 15 & 16). RNA strands were allowed to bind to the beads, and washed to remove any unbound nucleic acid using phosphate-buffered saline (PBS). The bead was then suspended in a primer extension buffer with Klenow fragment.

Figure 24A:
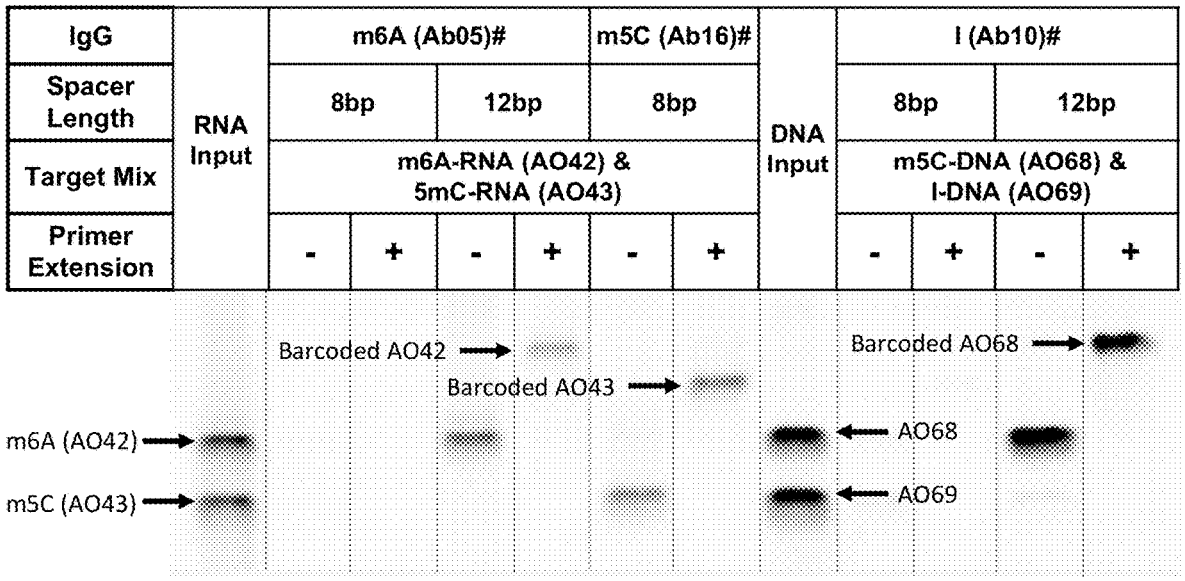
FIGS. 24A-24C show experimental results for barcoding DNA and RNA targets using nucleic acid binding molecules. The nucleic acid binding molecules comprise the RNA specific antibodies described in Example 1, conjugated to barcoded DNA adapters. Nucleic acid binding molecules are immobilized on protein G beads and incubated with an equimolar mixture of two nucleic acid targets.
Figure 24B:
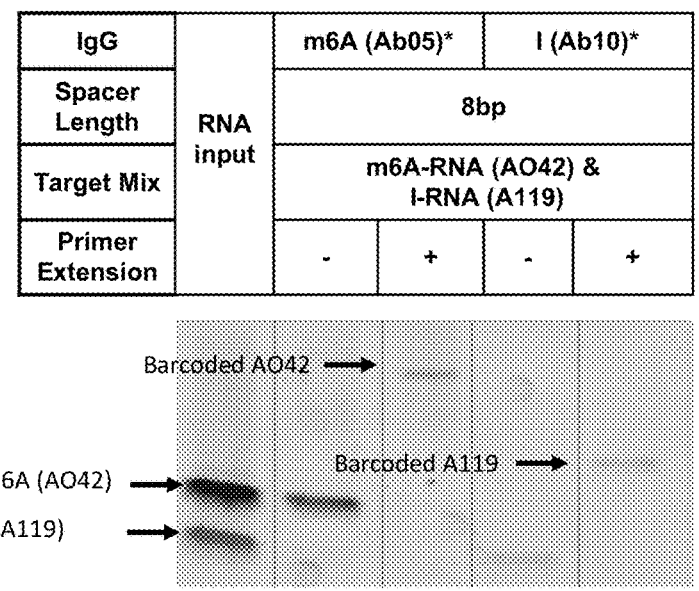

The resultant products (i.e., target RNAs extended by barcodes) were visualized on a 15% TBU gel, and the product lengths and quantities were analyzed (FIG. 24A). Ab16 with the 8b spacer primer extension adapter correctly barcoded the m5C RNA target. No background barcoding of the m6A target was detected, providing proof for the specificity of the reaction. Ab05 with the 12b spacer correctly barcoded the m6A RNA targets, however, the 8b spacer version failed to pull down any target. Knowing that the unlabeled Ab05 pulled down the m6A target easily, this suggested that labeling weakened the binding affinity to the extent that the additional stabilization of the 12b spacer is necessary to afford binding. Ab10 showed the same phenotype. The 12b spacer version pulled down target, whereas the 8b spacer version did not. However, Ab10 had completely lost specificity and the spacer interaction overpowered antibody selectivity. FIG. 24B shows that the activity of Ab05 and specificity of Ab10 were recovered using an 8b spacer and labeling the antibodies site selectively avoids impairment of the binding domain. In summary, the primer extension reactions work with high efficiency in the antibody-mediated format, but random labeling can weaken binding affinity (c.f. Ab05), or negatively impact specificity (c.f. Ab10) in the presence of a 12b spacer. Although primer extension in Example 7 suggests that a 12b spacer may be necessary to extend RNA, this data set clearly shows that the proximity effect accelerates the reaction and that 12b spacers are too long and can be associated with a lack of specificity. Thus, future nucleic acid binding molecules will be labeled with 8b spacer adapters, as demonstrated in FIG. 24B.

Figure 24C:
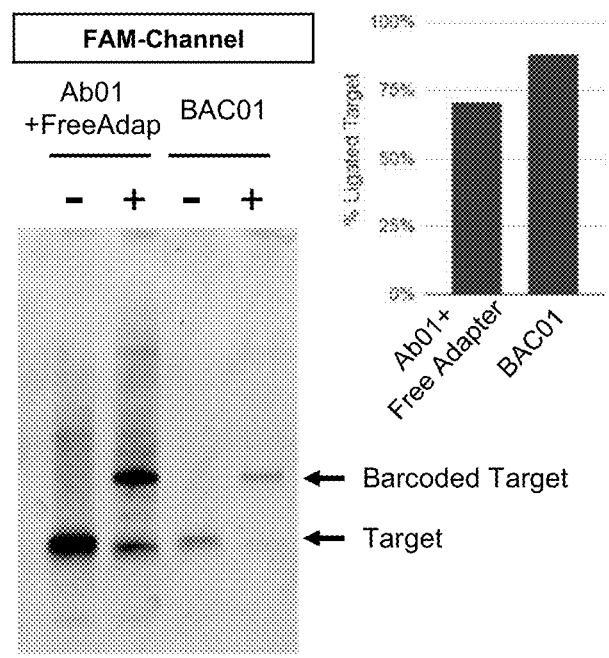

Barcoding by primer ligation was devoid of stabilizing spacer interactions. FIG. 24C shows the barcoding of a m6A-labeled RNA target (SEQ ID NO:17) by Ab01 labeled with a site-clicked adapter (SEQ ID NO: 39). Adapter sequences for barcoding by ligation and analysis by sequences had the following architecture: /5Phos/ACTAAT-TNNNAGATCGGAAGAGCACACGTCT/iSp18/T/3AmMO/; SEQ ID NO: 57 (5Phos=5'phosphate, bold=MBC, NNN=UMI, cursive=Illumina adapter, iSP18=PEG linker, 3AmMO=3' amine). The ligation conditions were the same as described in Example 6. The yield of the reaction was about 10% higher than the ligation of free adapter, again evidencing acceleration by proximity.

TABLE 7

Synthetic targets and adapters

| Description | Sequence | SEQ ID NO |
|---|---|---|
| Synthetic RNA target comprising m6A modification and an 8 bp DNA spacer | 5'-FAMrUrCrGrUrCrGrGrCrArGrCrGrUrCrArGrArUrGrCrArUrArArGrGrUrCr(m6A)rArUrArUrUrArArGrUrArUrArGACTGAGTG | 13 |
| Synthetic RNA target comprising m5C modification and an 8 bp DNA spacer | 5'-FAM-rUrCrGrUrCrGrGrCrArGrCrGrUrCrArGrArUrGrArUrArUrUr(m5C)rGrArArGrUrArUACTGAGTG | 14 |
| 50 base DNA target | 5'FAM-TCGTCGGCAGCGTCAGATGCATAATCTA(m5C)ATCTTAAGTATAGACTGAGTG | 15 |
| Synthetic DNA target comprising I modification | 5'-FAM-TCGTCGGCAGCGTCAGATGATACT(I)GCAGTATACTGAGTG | 16 |
| Synthetic RNA target comprising I modification | 5'FAMrUrCrGrUrCrGrGrCrArGrCrGrUrCrArGrArUrGrCrArUrArCr(I)rArCr CrCrArUrArGACTGAGTG | 41 |
| Synthetic RNA target comprising m6A label | 5'-FAM-rUrCrGrUrCrGrGrCrArGrCrGrUrCrArGrArUrGrCrArUrArArGrGrUr Cr(m6A)rArUrArUrUrArArGrUrArUrArGrGrArC | 17 |
| Site-clicked adapter | /5Phos/CGGACACAGACAGAGAATATUATATATA/iSp18/T/3AmMO/ | 39 |

Example 9: Preparation of Beads Comprising Nucleic Acid-Binding Molecules at Single Molecule Spacing While pulldown of nucleic acid targets by antibodies immobilized on protein A/G Dynabeads is a standard method in CHIP-Seq, the beads used in the instant example are custom tailored to provide multiple benefits: (i) false positives are avoided by improved surface passivation (a passivated surface avoids non-specific binding to the beads, so binding of modified nucleic acids is substantially via interaction with a nucleic-acid binding molecule); (ii) the density of nucleic acid-binding molecules on the bead surface is adjustable, for example to provide appropriate spatial separation between the molecules on the surface as required for barcoding according to FIG. 5B; (iii) the beads can be designed to facilitate capture and/or co-grafting of other recognition elements besides antibody Fc regions; (iv) the nucleic acid-binding molecules are covalently linked and do not co-elute during workflow steps; and (v) multiple types of nucleic acid-binding molecules can be present on the surface, which is relevant for some applications.

Carboxylated Dynabeads (Thermo) are surface coated with a binary mixture of Amino-PEG4-alcohol (Broadpharm, BP-20589) and Mal(maleimide)-PEG2-amine (Broadpharm, BP-23313). The Mal(maleimide)-PEG2-amine is used to couple cysteine-modified Spycatcher, whereas Amino-PEG-alcohol spaces out the nucleic acid-binding molecules and passivates the bead surface against nonspecific binding. The ratio of Amino-PEG4-alcohol to Mal-PEG2-amine (i.e., passivation:activation molecules) is adjusted to immobilize one Spycatcher molecule in approximately every 100 nm 2. This spatially separates the nucleic acid-binding molecules and sequesters them from other molecules when bound to target RNAs, thus enforcing intramolecular barcode transfer.

After washing the Dynabeads in 25 mM MES pH 5 (2-(N-morpholino)ethanesulfonic acid), 50 µL fresh EDC (N-(3-Dimethylaminopropyl)-N'-ethylcarbodiimide hydrochloride) and 50 µL NHS (N-Hydroxysuccinimide) in 25 mM MES pH 5 are added to a suspension of 100 µL beads. The reaction is allowed to proceed for 30 minutes at room temperature. The supernatant is then removed, and the beads are washed again. After the EDC/NHS step, the Dynabeads are coated with a binary mixture of Amino-PEG4-alcohol and MAL-PEG2-amine. The maleimide groups are covalently tethered to Spycatcher in the next step. Spycatcher is dissolved in 20 mM Tris pH 7 and the cysteine groups are reduced with TCEP (tris(2-carboxyethyl)phosphine). Maleimide-activated beads and Spycatcher protein are mixed and allowed to react for 2 hours at room temperature. After washing the beads, the number of Spycatcher proteins per bead is calculated by reacting Spycatcher protein with a Spytag-DNA conjugate and qPCR quantification of the conjugate. Spycatcher decorated beads are reacted with the spytag-binder-barcode conjugates described in Example 4.

Example 10: Preparation of Passivated Beads with Tunable Capture Probe Density

Targeted nucleic acid modification analysis according to FIG. 4C involves capturing nucleic acid sequences of interest on a bead followed by encoding of non-canonical features. Isolating the encoding complexes by precisely controlling their surface density prevents cross-talk between neighboring molecules. The following method describes the preparation of beads with a range of capture probe densities.

Porous NHS-activated Sepharose beads (Cytiva, cat. no. 17071601) were washed in 100% isopropanol and 1 mM HCl. To passivate and chemically functionalize the beads, they were incubated for 16 h at room temperature in 0.25M sodium bicarbonate buffer pH 8, 0.5M NaCl, 40 mM COOH-PEG4-Amine (passivating molecule; Broadpharm, cat. no. BP-20423) and variable amounts of mTet(tetrazine)-PEG4-amine (functionalizing molecule; Broadpharm, cat. no. BP-22435). Beads with mTet-PEG:carboxy-PEG ratios of 1:1,000, 1:10,000, 1:100,000 were prepared using 40, 400 and 4,000 µM mTet-PEG. A 100% carboxy-PEG bead was generated to measure the background. The 3' amine of a DNA capture probe (CATCTGACGCTGCCGACGAT-TTTTT/3AmMO/; SEQ ID NO: 20) was activated with NHS-PEG-TCO (trans-cyclooctene) (Broadpharm, cat. no. BP-22418) and anchored on the bead by reaction with mTet for 16 h at 22 C in 1×PBST (137 mM NaCl, 2.7 mM KCl, 10 mM Na2HPO4, 1.8 mM KH2PO4, 0.1% Tween® 20 detergent). The mTet/TCO pair is a well-studied inverse-demand Diels-Alder cycloaddition that occurs with a rate of >800 $M^{-1}$ $s^{-1}$ at physiological conditions, forming a dihydropyridazine bond.

The capture probe density was determined by qPCR after hybridizing an amplifiable tracer oligonucleotide (TCGTCGGCAGCGTCAGATGATTGTGT-TAGGCTAGTAAGTAGATGGATTAGACCGTC GAGT-GAGTAGAGTACGTAGTGCA, SEQ ID NO: 21) to the capture probes on the beads. The threshold cycle (Ct) values were converted into number of DNA molecules per bead based on a calibration curve (FIG. 25). Each 10-fold increase in mTet-PEG allowed for capturing 10-times more tracer oligonucleotides, consistent with the theoretical prediction. The mTet concentration that spaced out the encoding complexes at a distance that prevented neighbor interactions was determined experimentally (see Example 12). The background was low, with the number of DNA strands detected on the mTet-free bead corresponding to 0.1% of the molecules detected on the highest density bead.

Example 11: Proximity Barcoding in Solution Using a Model Nucleic Acid Binding Domain and Ligation The dissociation constant for streptavidin and biotin is on the order of ≈$10^{-14}$ mol/L, one of the strongest affinity interactions known in nature and orders of magnitudes stronger than the typical affinity of antibodies to modified RNA bases. A simple nucleic acid binding molecule was designed comprising streptavidin as a binding domain and biotinylated ligation adapters. The goal of this method is to transfer the barcode of a nucleic acid-binding molecule exclusively to the target RNA to which the molecule is bound using a binding domain of extraordinarily high affinity and specificity. Such a model system is invaluable as a process control and for exploring the ceiling of barcoding at quasi-infinite affinity of the nucleic acid binding molecule.

Streptavidin and biotin-adapter (SEQ ID NO: 33) were mixed at a ratio of 1:1, 1:2, 1:3 and 1:4 in a low ionic strength buffer (10 mM Tris pH 7.5, 50 mM NaCl, 1 mM EDTA, 0.05% Tween-20) and the resulting complexes were analyzed by electrophoresis using a native 8% TBE gel (FIG. 26A). Three out of the four biotin-binding pockets of streptavidin were loaded with increasing concentrations of biotin-adapter. The 1:2 ratio is best suited for encoding because unlabeled streptavidin is absent, and a binding pocket is available for binding of a biotinylated RNA target.

Figure 26B:
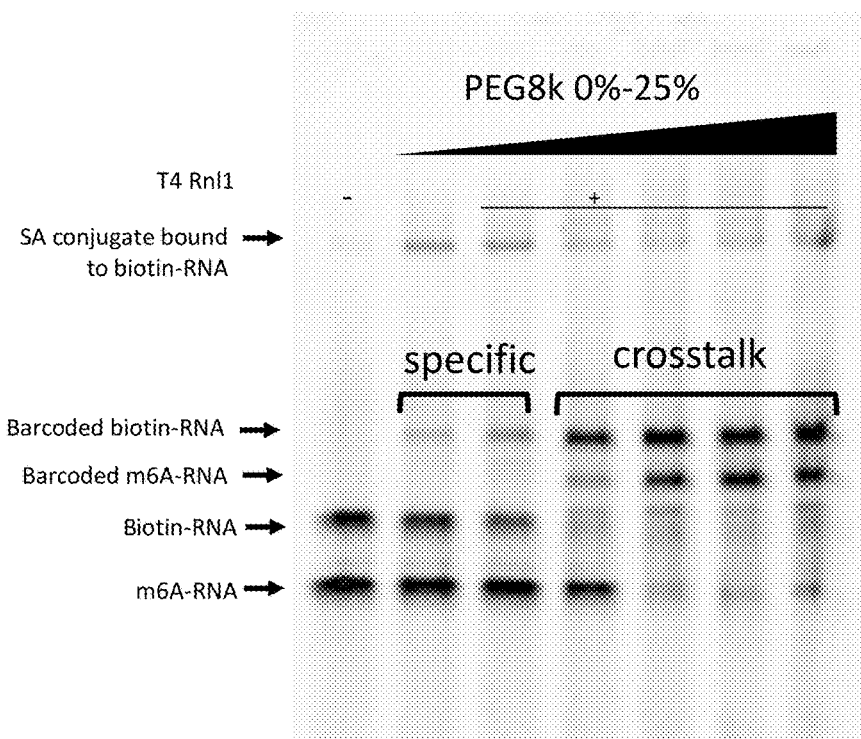
Figure 26C:
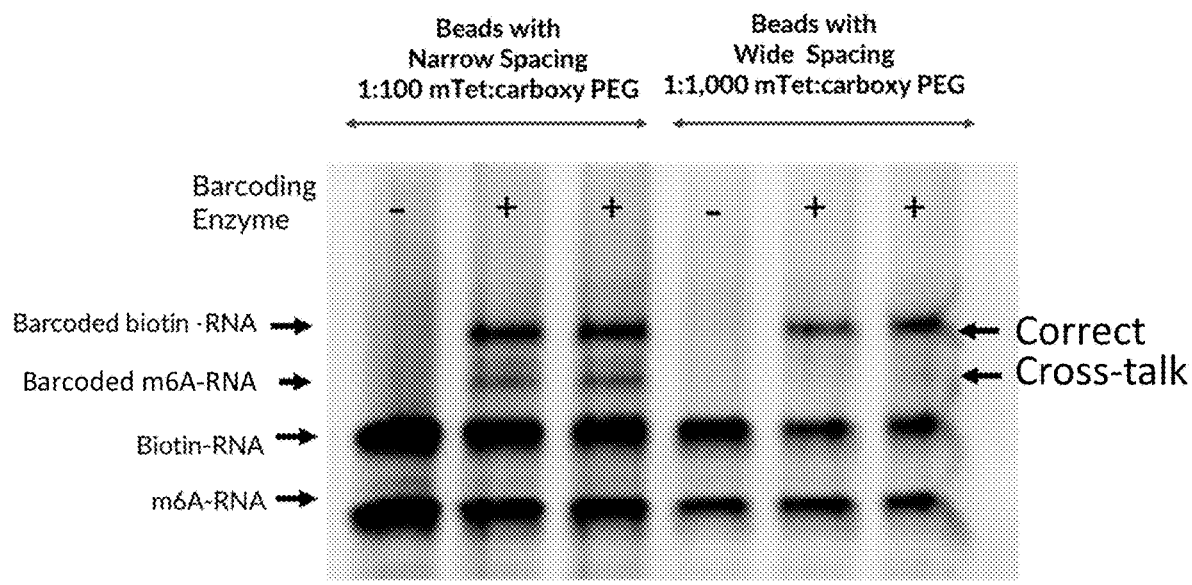

To demonstrate proximity encoding in solution, the streptavidin nucleic acid binding molecule was mixed with an equimolar mixture of m6A-modified RNA (off-target; SEQ ID NO: 32) and biotin-RNA (on-target; SEQ ID NO:40). The RNA strands were dye-labeled and differ in size to differentiate on- and off-target encoding by gel electrophoresis. Ligation was conducted for 1 hour at 22° C. in 50 mM Tris-HCl pH 7.5, 10 mM $MgCl_2$, 1 mM DTT, 0.5 mM ATP, 400 nM 1:2 streptavidin-biotin-adapter conjugate, and 100 nM of each RNA target. The PEG-8000 concentration in the ligation reaction was varied from 0 to 25% to modulate the average intermolecular spacing through molecular crowding. After ligation the streptavidin was disconnected from the adapter by cleaving the adapter at a single uracil with USER (NEB, cat. no. M5505L) to facilitate gel analysis. Molecular crowding decreased the volume available to the biomolecules, thus effectively increasing the concentration. The results were consistent with the theory that predicted specific barcoding at low PEG concentrations where the intermolecular spacing is large, whereas higher PEG concentrations condense the molecules and triggered crosstalk (FIG. 26B). The crosstalk observed in this example occurred when the streptavidin conjugate was bound to the correct biotin-RNA but barcoded another m6A RNA that was in close proximity but not bound. The example demonstrates that on-target barcoding in solution is possible, provided the average distance of the barcoding complexes is tightly controlled.

TABLE 8

Adapter and RNA sequences

| Description | Sequence | SEQ ID NO |
|---|---|---|
| m6A modified RNA | 5'-FAM-rUrCrGrUrCrGrGrCrArGrCrGrGrUrCrArGrArUrGrCrCrUrGrCrArArGr Gr (m6A)rCrUrGrCrUrUrUrGrArC | 32 |
| biotin-adapter | /5Phos/CGGACACAGACAGAGAATATUATATATA/iSp18/T/3BiotinTEG/ | 33 |
| Biotin-RNA | 5'-FAM-rGrGrCrArGrCrGrUrCrArGrArUrGrCrArUrCrArUrCrArUrArArGrGrUr Cr(biotin-U)rArUrArUrUrArArGrUrArUrArGrArC | 40 |

Example 12: Barcode Transfer by Sequence-Specific Capture of RNA on Single Molecule Beads and Barcoding Using a Model Nucleic Acid Binding Domain This example uses the same model binding domain derived from streptavidin and experimental design as described in Example 11. However, the ligation reaction was performed on immobilized beads that were prepared as described in Example 10. Two types of beads were used: Sepharose beads with a 1:100 ratio of mTet:carboxy-PEG or a 1:1000 ratio of mTet:carboxy-PEG.

Each reaction contains 2,000 1:100 mTET/carboxy or 20,000 1:1,000 mTET/carboxy beads decorated with capture DNA (SEQ ID NO: 20). The beads were incubated with a mixture of biotin (SEQ ID NO: 31) and m6A RNA (SEQ ID NO: 32) at 1.5 µM in 80 µL 5×SSC buffer with 0.1% Tween20 for 1 hour at 37° C. Both RNA targets exhibited a 21b region that is complementary to the capture probes on the beads. After completion of hybridization, unbound target was removed by two washes with 200 µL high salt PBST (PBS with 0.1% Tween20 and 360 mM NaCl) and one wash with 100 µL PBT (PBS with 0.1% Tween20 and 360 mM NaCl). The beads were incubated with streptavidin-adapter conjugate in high salt PBST for 20 min. Excess conjugate was washed away as described for the RNA targets. Ligation and analysis was performed as in Example 11. FIG. 26B shows specific barcoding of the biotin target with 1:1,000 mTET/carboxy beads, and crosstalk with 1:100 mTET/carboxy beads. In this example, crosstalk was a consequence of close packing of RNA targets on the surface at the greater density of 1:100 mTET/carboxy beads.

Example 13: Barcode Transfer in Solution Using Ligation and Primer Extension Measured by PCR The goal of the following method is to transfer the barcode of a nucleic acid-binding protein (i.e., a nucleic acid-binding protein as described in Examples 3 and 4) exclusively to a target RNA to which the molecule is bound.

Figure 18A:
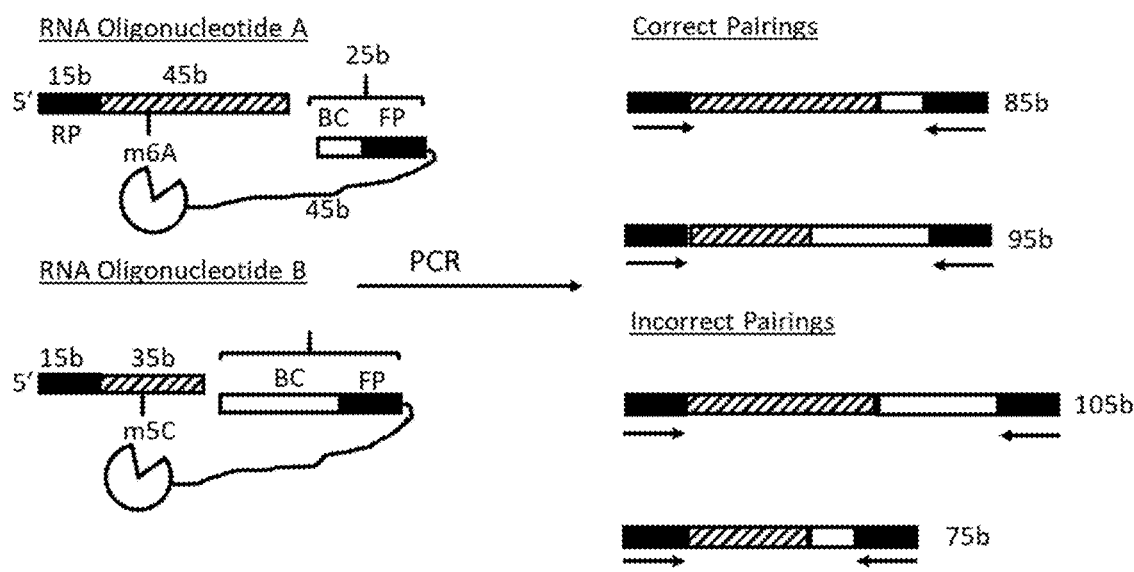
FIGS. 18A-18B are schematics showing illustrative methods for measuring barcode crosstalk in a model system.
Figure 18B:
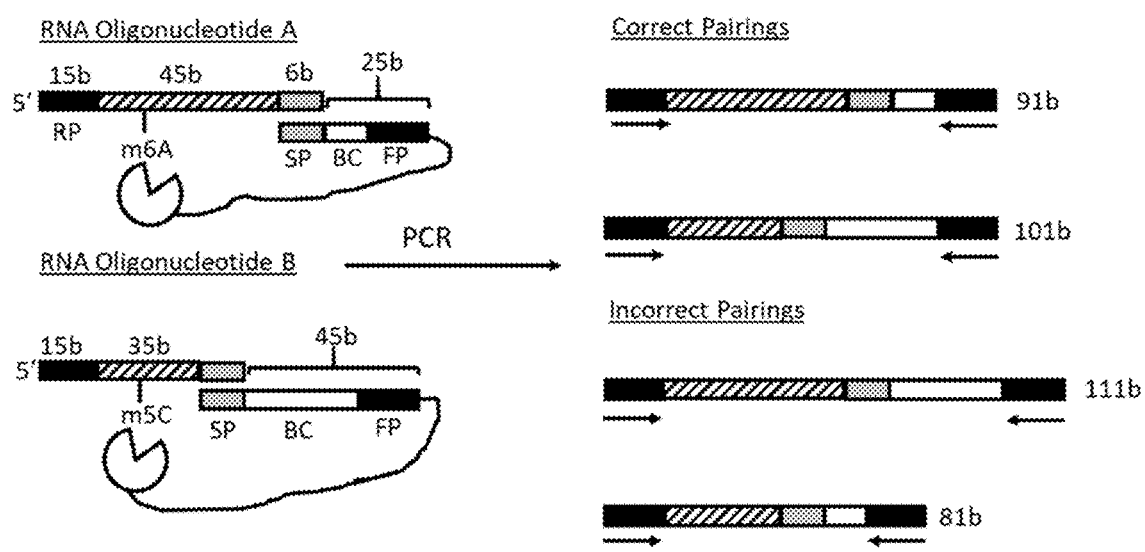

Both target RNAs with a m6A and m5C modification (FIGS. 18A and 18B) and their cognate nucleic acid-binding molecules are mixed and allowed to bind. Barcode transfer reactions are performed in solution, and the barcode transfer mechanism is either ligation or primer extension. For barcode transfer by ligation, the barcode is tethered to the binding domain of the nucleic acid-binding molecule (i.e., an antibody) via the 5' end, and the 3' end of the barcode is pre-adenylated. Ligation is initiated by addition of T4 RNA ligase II. For barcode transfer by primer extension, a short spacer sequence is added to the 3' end of the target RNA and the barcode contains a region that is complementary to the spacer. Spacer extension is conducted with a DNA polymerase, such as Klenow fragment, and dNTPs (deoxyribonucleotide triphosphates) at 37° C. for 5 min.

Barcode transfer efficiency, as well as off-target barcoding, is measured by PCR using a model oligonucleotide system. Correct and incorrect barcode pairings are determined based on the length of PCR products as described in FIGS. 18A and 18B Specifically, after completion of the barcode transfer reactions, the reaction products are PCR amplified and the size of the products is visualized by gel electrophoresis. Bands of unexpected size indicate the occurrence of off-target barcode transfer. This reaction scheme is used to optimize adapter architecture, choice of enzymes and reaction conditions for maximal barcode transfer efficiency and minimal off-target activity.

Example 14: Barcode Transfer by Sequence-Specific Capture of RNA

Barcode transfer may also be performed when a target RNA itself is coupled to the surface of a bead (FIG. 4C). The target RNA is captured on the bead surface by nucleic acid hybridization (i.e., capture of the target RNA on the bead surface does not depend on recognition of a modification of the target RNA by a nucleic acid-binding molecule). Target capture by nucleic acid hybridization enables the selective enrichment of genomic or transcriptomic regions of interest.

A bead displaying DNA capture probes is prepared according to Example 4; instead of cysteine-modified Spycatcher, thiolated DNA oligonucleotides are immobilized, wherein the sequence of the thiolated DNA oligonucleotides is complementary to a region of the target RNA. These capture oligonucleotides are present at less than 1 molecule per 100 nm 2 on the surface of the beads to ensure the specificity of the intramolecular barcode transfer reactions. The m6A and m5C model oligonucleotides (FIGS. 18A and 18B) are captured in hybridization buffer. After washing, a pool of nucleic acid-binding molecules capable of binding to m6A and m5C is added. Barcode transfer reactions are then performed by ligation or primer extension as described in Examples 6 and 7. Barcode transfer efficiency and specificity are measured by PCR.

Example 15: Preparation of Binding Domain-Cytosine Deaminase Conjugates and Measurement of Base Editing Cytosine deaminase catalyzes the hydrolytic deamination of cytosine to uracil (C-to-U mutation). The enzyme has been used for gene editing, wherein it is targeted to a gene region of interest by fusion to a catalytically inactive Cas9-guide RNA complex. In this example, cytosine deaminase was targeted to an RNA modification by a binding domain (e.g., by antibody binding). The goal was to engineer a binding domain-deaminase conjugate that restricted the deaminase activity to a window of a few bases at consistent proximity to the RNA modification.

Most cytosine deaminases act on single-stranded DNA. APOBEC1 and APOBEC3A are the only enzymes known to possess RNA editing activity, and rat APOBEC1 (Uniprot accession no. P38483) has been used successfully for targeted RNA editing mediated by catalytically inactive Cas9-guide RNA complex. Human YTHDF2 (Uniprot accession no. Q9Y5A9) is a native m6A reader protein that binds m6A with dissociation constants ranging from $K_D$=150-1200 nM, depending on sequence context. Two approaches were pursued to obtain an m6A-targeting binding domain-deaminase conjugate. One approach was to fuse APOBEC1 directly to YTHDF2 (Meyer, K. *Nature Methods* 16, 1275-1280 (2019)). The other approach was fusing Spytag to APOBEC1 and Spycatcher to YTHDF2 and letting them react to form a covalent conjugate as part of the assay workflow.

Figure 27:
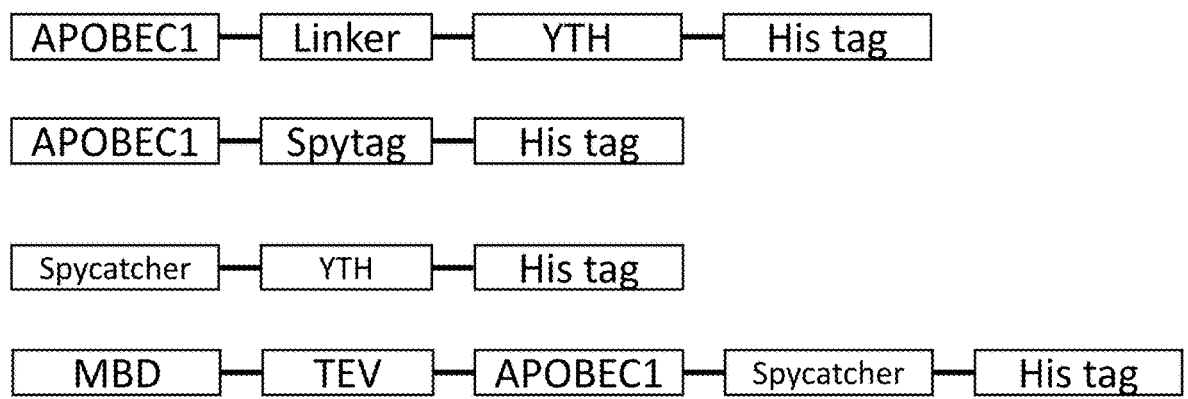
FIG. 27 is a schematic of the protein domain organization of fusion proteins designs for position marking of RNA modifications by targeted deamination. APOBEC1=cytidine deaminase, YTH=m6A reader protein, Spytag=peptide for covalent targeting, Spycatcher=protein for covalent targeting, TEV=cleavage site for TEV protease, His-tag=affinity tag for purification, MBD=maltose binding domain, a tag for affinity purification that improves protein solubility.

Initially, three fusion constructs were expressed in *E. coli* cells: (1) APOBEC1-YTH-His comprising rat APOBEC1 (aa 1-229) and the binding domain of YTHDF2 (aa 385-579) (FIG. 27 and SEQ ID NO: 34). (2) APOBEC1-Spytag-His comprising the same APOBEC1 and Spytag002 (FIG. 27 and SEQ ID NO: 35). (3) Spycatcher-YTH-His comprising the same YTHDF2 fragment and Spycatcher002 (FIG. 27 and SEQ ID NO: 36) as provided in Table 6. (4) MBD-TEV-APOBEC1-Spycatcher-His comprising a maltose binding domain (MBD), a TEV protease cleavage site (TEV), and APOBEC1 and Spycatcher as described above. Spytag002 and Spycatcher002 are the latest published versions of the Spy system exhibiting the fastest reaction rates ever reported for a covalent peptide tag. The genes were codon-optimized, synthesized, cloned into a pET-30a vector in frame with a C-terminal his-tag, and expressed in BL21 cells. FIG. 28 showed similar induction after 16 hours at 15° C. and 4 hours at 37° C. However, only Spycatcher-YTH-His was present in the soluble fraction, whereas the APOBEC containing proteins were mostly insoluble. To solve the APOBEC solubility problem, MBD-TEV-APOBEC1-Spycatcher-His was generated, which comprised APOBEC flanked by the maltose binding domain (MBD) and Spycatcher, both known for their excellent solubility. A TEV cleavage site was introduced to enable the removal of MBD. This construct produced soluble protein, particularly when expressed for 16 hours at 15° C. (FIG. 28). The cells were lysed in a high salt buffer to disrupt electrostatic interactions with nucleic acids and treated with nuclease (50 mM Tris, 500 mM NaCl, 1 mM TCEP, pH 8.0, Nuclease (Thermo Fisher, cat. no. 88700). Binding to MBD or Ni column were both moderate indicating that neither of the affinity tags were well accessible. Eluted fractions were pooled and subjected to a size exclusion purification (Superdex 200 column) (FIGS. 29A and 29B). Although the initial deaminase conjugates developed lacked solubility, these data demonstrate creation of a soluble protein tag-deaminase conjugate for application in restricting deaminase activity to close proximity with the target nucleotide modification of interest.

TABLE 6

Fusion Constructs

| Description | Sequence | SEQ ID NO |
|---|---|---|
| APOBEC1-linker-YTH-His<br>Bold = APOBEC1<br>Italics = linker<br>Underlined = YTH | MSSETGPVAVDPTLRRRIEPHEFEVFFDPRELRKETCLLYEI NWGGRHSIWRHTSQNTNKHVEVNFIEKFTTERYFCPNTRC SITWFLSWSPCGECSRAITEFLSRYPHVTLFIYIARLYHHAD PRNRQGLRDLISSGVTIQIMTEQESGYCWRNFVNYSPSNEA HWPRYPHLWVRLYVLELYCIILGLPPCLNILRRKQPQLTFF TIALQSCHYQRLPPHILWATGLK*GGSGGSGGSGGS*PHPVLEK LRSINNYNPKDFDWNLKHGRVFIIKSYSEDDIHRSIKYNIWCST EHGNKRLDAAYRSMNGKGPVYLLFSVNGSGHFCGVAEMKSA VDYNTCAGVWSQDKWKGRFDVRWIFVKDVPNSQLRHIRLEN NENKPVTNSRDTQEVPLEKAKQVLKIIASYKHTTSIFDDFSHYE KRQEEEESVKKERQGRGKHHHHHH | 34 |
| APOBEC1-Spytag-His<br>Bold = APOBEC1<br>Italics = linker<br>Underlined = Spytag | MSSETGPVAVDPTLRRRIEPHEFEVFFDPRELRKETCLLYEI NWGGRHSIWRHTSQNTNKHVEVNFIEKFTTERYFCPNTRC SITWFLSWSPCGECSRAITEFLSRYPHVTLFIYIARLYHHAD PRNRQGLRDLISSGVTIQIMTEQESGYCWRNFVNYSPSNEA HWPRYPHLWVRLYVLELYCIILGLPPCLNILRRKQPQLTFF TIALQSCHYQRLPPHILWATGLK*GGS*RGVPHIVMVDAYKRY KHHHHHH | 35 |

TABLE 6-continued

Fusion Constructs

| Description | Sequence | SEQ ID NO |
|---|---|---|
| Spycatcher-YTH-His<br>Bold = Spycatcher<br>Italics = linker<br>Underlined = YTH | MVTTLSGLSGEQGPSGDMTTEEDSATHIKFSKRDEDGRELA<br>GATMELRDSSGKTISTWISDGHVKDFYLYPGKYTFVETAAP<br>DGYEVATPIEFTVNEDGQVTVDGEATEGDAHT*GGGG*SPHPV<br>LEKLRSINNYNPKDFDWNLKHGRVFIIKSYSEDDIHRSIKYNIW<br>CSTEHGNKRLDAAYRSMNGKGPVYLLFSVNGSGHFCGVAEM<br>KSAVDYNTCAGVWSQDKWKGRFDVRWIFVKDVPNSQLRHIR<br>LENNENKPVTNSRDTQEVPLEKAKQVLKIIASYKHTTSIFDDFS<br>HYEKRQEEEESVKKERQGRGKHHHHHH | 36 |
| MBD-TEV-APOBEC1-Spycatcher-His<br>Bold = MBD<br>Italics & underlined = TEV site with linker<br>Bold & Italics = APOBEC1<br>Italics = linker<br>Underlined = Spy catcher | MKIEEGKLVIWINGDKGYNGLAEVGKKFEKDTGIKVTVE<br>HPDKLEEKFPQVAATGDGPDIIFWAHDRFGGYAQSGLLAE<br>ITPDKAFQDKLYPFTWDAVRYNGKLIAYPIAVEALSLIYNK<br>DLLPNPPKTWEEIPALDKELKAKGKSALMFNLQEPYFTWP<br>LIAADGGYAFKYENGKYDIKDVGVDNAGAKAGLTFLVDLI<br>KNKHMNADTDYSIAEAAFNKGETAMTINGPWAWSNIDTS<br>KVNYGVTVLPTFKGQPSKPFVGVLSAGINAASPNKELAKE<br>FLENYLLTDEGLEAVNKDKPLGAVALKSYEEELVKDPRIA<br>ATMENAQKGEIMPNIPQMSAFWYAVRTAVINAASGRQTV<br>DEALKDAQTN*SSSNNNNNNNNNNLGIEGRISHMGSGSSGSGENL*<br>*YFQGMSSETGPVAVDPTLRRRIEPHEFEVFFDPRELRKETCLL*<br>*YEINWGGRHSIWRHTSQNTNKHVEVNFIEKFTTERYFCPNTR*<br>*CSITWFLSWSPCGECSRAITEFLSRYPHVTLFIYIARLYHHADP*<br>*RNRQGLRDLISSGVTIQIMTEQESGYCWRNFVNYSPSNEAHW*<br>*PRYPHLWVRLYVLELYCIILGLPPCLNILRRKQPQLTFFTIALQ*<br>*SCHYQRLPPHILWATGLK**SGSETPGTSESATPESM*VTTLSGLSG<br>EQGPSGDMTTEEDSATHIKFSKRDEDGRELAGAT<u>MELRDSSG</u><br><u>KTISTWISDGHVKDFYLYPGKYTFVETAA</u>PDGYEVATPIEFTV<br>NEDGQVTVDGEATEGDAHT*GSSGS*HHHHHH | 37 |

Example 16: RNA Profiling by Barcoding, cDNA Truncation and Circularization

In this example, modifications on a target RNA are identified via recognition by a nucleic acid-binding molecule and subsequent transfer of the barcode to the RNA target. The position of the modification is revealed by the truncation of cDNA during reverse transcription (FIG. 8), either induced by cross-linking of the binding domain of the nucleic acid-binding molecule, or by a binding domain that is engineered accordingly.

Total Human Reference RNA (Thermo) is ribo-RNA depleted and fragmented to an average size of 100-150 nucleotides using incubation with magnesium ($Mg^{2+}$) ions at 95° C. The 3' ends of RNA are dephosphorylated using T4 polynucleotide kinase (NEB) and shrimp alkaline phosphatase (NEB). Control RNA oligonucleotides with N6-Methyladenosine (m6A), pseudouridine (Ψ) and 5-Methylcytosine (m5C) and analogous oligonucleotides without modification are spiked into the RNA sample at a known concentration as positive control.

Beads displaying nucleic acid binding molecules that recognize the RNA modifications m6A, Ψ or m5C are made using the methods described in Examples 4 & 5. Each bead type displays a single species of nucleic acid binding molecule. The design of the adapters is as described in FIG. 2B. The beads are mixed and incubated with the RNA sample in a binding buffer and subsequently crosslinked with UV light at 0.15 J $cm^{-2}$ (254 nm). The supernatant contains the unmodified RNA, whereas the modified RNA binds to the beads.

To measure the abundance and stoichiometry of RNA modifications, unmodified and modified RNA fractions are converted into RNA-Seq libraries using a split workflow (see FIG. 7). Barcoding of the unmodified RNA fraction is performed as follows: Type B adapters (FIG. 2B) are added to the supernatant and ligated to the 3' end of RNA with T4 RNA ligase. The adapters are not attached to nucleic acid binding molecules and all unmodified RNA strands receive the same adapter and barcode. Where necessary, the RNA is purified between assay steps using physical absorption to Dynabeads™ MyOne™ Silane (Thermo Fisher) in RLT buffer with ethanol (Qiagen). For the modified RNA, the barcodes are transferred from the bead-immobilized nucleic acid binding molecules to the RNA molecules. The RNA molecules are still bound to the beads via the nucleic acid binding molecules. After this step, all protocol steps are identical for unmodified and modified RNA. Universal primers are added and extended by Superscript III (Thermo), whereby cDNA is truncated at the modification sites. To form circular cDNA, intramolecular ligation is initiated by incubation with CircLigase II (Lucigen) at 60° C. After cleaving the adapter with a restriction enzyme between the UFP and URP regions (FIG. 2B) cDNA is converted into a library by PCR with sequencing adapters. Modified and unmodified fractions are combined before sequencing and sequenced at 20 million reads. The type, number and location of m6A, Ψ, m5C are informatically determined. The control oligonucleotides are used as a reference to account for inefficiencies during the parallel library preparations.

Example 17: Targeted Capture and Stranded RNA Library Preparation with Modification Profiling by Barcoding and Base Editing In this example, specific RNA sequences are enriched by hybridization and the strand information is retained during library preparation. Beads with capture probes at single molecule spacing are prepared as described in Example 10. Each bead type displays a capture probe for a specific RNA locus and bead types are pooled to address any number of RNA loci.

Fragmented RNA is incubated with the bead pool in hybridization buffer (5×saline sodium citrate (SSC), 40% formamide, 0.1% Tween-20 detergent) at 37° C. for 16-hours. RNA strands bind to the capture probes regardless of modification status. A pool of nucleic acid binding molecules directed against 10 different modifications is added. The nucleic acid binding molecules comprise modification-specific IgG antibodies with Spytag (SEQ ID NO: 10) genetically engineered onto the C-terminus of the light chain. For positional marking of the modification, a deaminase-spycatcher fusion protein is added, which rapidly reacts with spytag and marks the location of the modification with a C-to-U mutation. After removal of the protein conjugates a second ligation step with free adapters barcodes the unmodified fraction of RNA. For a given locus, the modification stoichiometry corresponds to the number of modification barcodes divided by all barcodes. First strand cDNA synthesis is then performed using standard methods and the second strand is synthesized in the presence of dUTP. Treating the resultant library with USER enzyme (NEB) removes the second strand, thus preserving strand information. DNA sequencing then identifies the location of the RNA modifications at all sites in the RNA sample.

Example 18: Profiling of DNA Modifications by Strand Separation, Barcoding and Base Editing In this example, covalent immobilization of adapter-ligated DNA to beads is used to force the retention of strand separation, enabling base editing by single-strand specific cytosine deaminase for the accurate location marking of non-canonical features (FIG. 9).

A DNA sample is fragmented using shear forces or other common methods known to those skilled in the art. After end-repair and A-tailing of the DNA strands, Y-shaped adapters are ligated to both termini. These adapters feature a 3'-azido modification, a widely available modification of synthetic oligonucleotides. Under conditions suitable for the denaturation (strand separation) of duplex DNA (e.g. in polar organic solvents such as ethanol and acetonitrile or in 95% aqueous solutions of formamide), a click reaction is used to covalently link the single DNA strands to the substrate at single molecule spacing. This click reaction can be a Cu(I)-catalyzed azide-alkyne cycloaddition between azido-DNA and a surface-tethered alkyne at low density, a strain-promoted azide-alkyne cycloaddition, or other variant on this Huisgen chemistry.

Following immobilization, the denaturing conditions are removed (e.g. by solvent change or solvent evaporation) and a buffered aqueous solution is introduced along with the nucleic acid binding molecules linked to their barcodes. Barcode transfer then takes place by splinted DNA ligation catalyzed by T4 DNA ligase, as determined by specific recognition of the non-canonical feature.

Following the completion of barcode transfer, a secondary antibody conjugated to a cytosine deaminase is introduced, which carries out C-to-U base editing in close proximity to the site of the non-canonical feature. Following base editing, the DNA strands are cleaved from the substrate using USER cleavage. A primer is then introduced and bound to the adapter, and a DNA polymerase is used for cDNA synthesis with truncation at the site of the uracil. Library preparation and DNA sequencing then identifies the location of the non-canonical feature at all sites in the DNA sample.

Figure 14A:
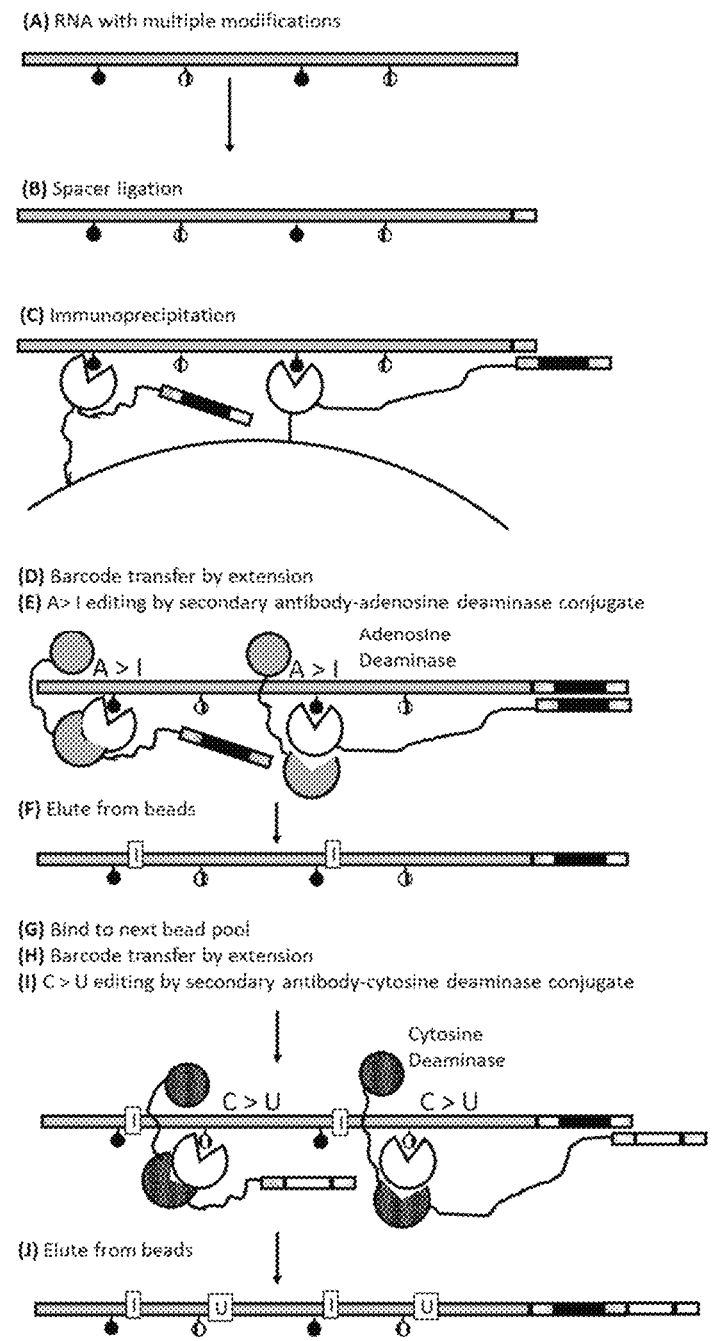
FIG. 14A is a schematic showing an illustrative method for cyclic profiling combining barcoding by primer extension and base editing.

Example 19: DNA Library Preparation with Two Cycles of RNA Modification Profiling and Base Editing In this example, multiple modifications and occurrences thereof are detected on the same RNA target strand. This is accomplished by two rounds of modification recognition by nucleic acid binding molecules and subsequent barcode transfer by primer extension (as depicted in FIGS. 14A and 14B). After each primer extension, the presence of multiple modifications of the same type is recorded by base editing.

To distinguish the editing cycles, base editing in the first cycle is performed by adenosine deaminase (A-to-I mutation) and in the second cyRNA is chemically fragmented to an average size of ~200-300 bp. To allow for barcode transfer by primer extension, a short 8 base spacer is ligated to the 3'end of RNA. The spacer serves as a hybridization site for the incoming barcode and a universal primer. The ligated RNA fragments are immunoprecipitated using one bead type and allowed to bind for about 2 hours. After washing the beads, barcode transfer is performed by incubating with Klenow fragments and dNTPs for about 5 minutes at 37° C. This step marks the type of bead the DNA target is bound to.

The position of the modifications is encoded by introducing A to I mutations near the modification sites. To this end, a secondary antibody-adenosine deaminase conjugate is added and allowed to react.

When editing is complete, the RNA is eluted and immunoprecipitated with a second bead type. Barcode transfer and base editing is repeated, but this time base editing is performed with cytosine deaminase introducing a C to U mutation. The barcode that is transferred in the second cycle contains a universal primer cap to make the DNA targets amplifiable. Adapter PCR with a DNA polymerase that tolerates uracil modifications generates a library for sequencing.

Example 20: Design of APOBEC-Spycatcher Fusion Proteins for In Vitro Translation and Functional Testing This example employs a cell-free in vitro translation system for the expression of deaminase enzymes designed for targeted deamination. The solubility and protein folding problems observed for the expression of APOBEC1 in *E. coli* were likely attributed to cell toxicity because APOBEC's DNA editing activity damages the host cell's genome. In vitro translation systems are commonly used for toxic and difficult to express protein. FIG. 30 shows the amino acid sequences for APOBEC1 and APOBEC3A (E109A) fused to Spycatcher via an XTEN linker (SEQ ID NOs: 42 and 43, respectively). In contrast to the genes used in Example 15, the his-tags for affinity purification and any unnecessary GS linkers were omitted to minimize structural perturbation of the enzymes. For the APOBEC1 fusion protein, the gene was PCR amplified from the plasmid expressing SEQ ID NO. 37, using a primer with a T7 promotor region. The APOBEC3A enzyme was constructed from the same plasmid by cloning in a gblock with the APOBEC3A(E109A) sequence (IDT). Both enzymes were expressed with and without the Spycatcher fusion using the PURExpress® In Vitro Protein Synthesis Kit (New England Biolabs). The reactions were assembled according to the manufacturer's protocol using 500 ng of each PCR-amplified gene as input. Protein expression was allowed to proceed at 37° C. for 5 hours.

Enzyme activity was measured by adding unpurified cell-free extract containing the enzymes of interest to a FAM-labeled DNA oligonucleotide that contains a single C in a central position. Cytidine deaminase activity converted the C to a U, which was subsequently cleaved by USER enzyme (NEB). FIG. 31 shows the cleavage products observed at decreasing concentrations of cell-free extract after incubating at 37° C. for 30 min. The most concentrated reaction contained 1.25 µL of cell-free extract in a 10 µL reaction volume (100 nM FAM-DNA, 10 mM Bis-Tris-Propane-HCl pH7, 10 mM $MgCl_2$, 100 µg/mL BSA). The cell-free extract was further diluted to 1:2, 1:4, 1:8, and 1:16. APOBEC1A exhibited weak deamination activity, which was enhanced in the presence of spycatcher protein. By comparison, APOBEC3A was at least 10-times more active than APOBEC1A, however, adding the spycatcher fusion had a mildly inhibitory effect.

These results confirm that it is possible to express catalytically active APOBEC1 and APOBEC3A fusion enzymes in an in vitro translation system.

Example 21: Targeted Deamination by APOBEC-Spycatcher Fusion Proteins

This example demonstrates that APOBEC-spycatcher fusion proteins can be targeted to a particular site of a DNA strand via the interaction of spycatcher and spytag. The covalent Spycatcher/Spytag reaction confines deaminase activity to a region near the attachment site.

Figure 32:
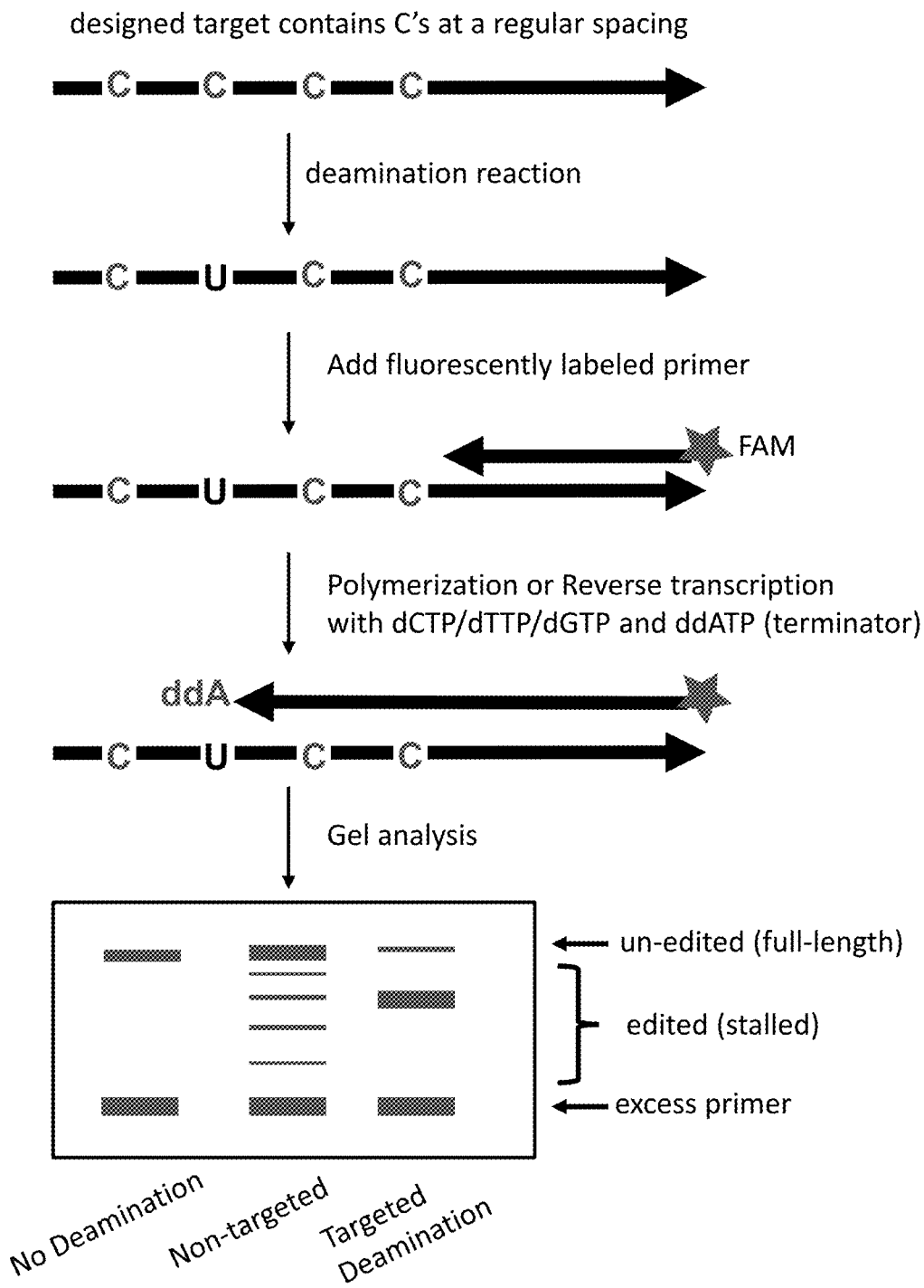
FIG. 32 is a schematic of a poisoned primer assay (PPA). The PPA assay is designed to measure the size of the deaminase activity window. The template used to probe the deaminase activity contains a series of cytidines separated by an AGAA sequence. "U"=uracil produced by deamination. Dashed gray line=polymerization or reverse transcription product extended from the primer oligo. "ddA"=dideoxyadenosine (reaction terminator). Dark gray bands in the schematic gel represents the expected gel analysis results.

FIG. 32 describes a poisoned primer assay (PPA) that was used to measure the size of the deaminase activity window. A DNA or RNA template containing several C's at a regular spacing were hybridized to a FAM-labeled primer. Primer extension was carried out in the presence of dCTP, dTTP, dGTP and ddATP and either a DNA polymerase (Klenow fragment for a DNA template) or reverse transcriptase (M-MLV for an RNA template) after treating the template with deaminase. The presence of C-to-U edits prompted the incorporation of ddATP, thus causing primer termination. The size distribution of the extension products was analyzed by denaturing gel electrophoresis to locate the sites of base editing.

Initially, the PPA assay was tested with a commercial version of APOBEC3A (New England Biolabs). FIG. 33 shows that APOBEC3A was highly active on a DNA template (U and C templates being SEQ ID NOs: 44 and 45, respectively) but had weak activity with RNA (U and C templates being SEQ ID NOs: 46 and 47, respectively). Thus, this enzyme is a suitable candidate for marking the position of non-canonical features in DNA.

To test the ability of targeting deaminase to a non-canonical feature as shown in FIG. 6C, a simplified model system was used (FIG. 34). Rather than employing a Spytag-labeled binding domain, Spytag peptide was directly tethered to a DNA strand (e.g. SEQ ID NO: 50) at a thymine position. Spytag peptide was either attached distally, 26b away from the first C (SEQ ID NO: 48) at thymine, or proximally, 2b away from the first C (SEQ ID NO: 49) at thymine.

FIG. 35 depicts the results of the targeted deamination assay conducted with APOBEC3A fusion proteins. 100 nM of DNA template (with or without SpyTag) was incubated with 7.6 µL of cell-free extract containing APOBEC3A and APOBEC3A-spycatcher in a total reaction volume of 42 µL in deamination buffer (10 mM Bis-Tris-Propane-HCl pH7, 10 mM $MgCl_2$, 100 µg/mL BSA). 8 µL time points were collected after 1, 3, 8, 15 minutes and deaminase was immediately heat deactivated at 95° C. 1 µL of Klenow DNA polymerase mix was added to the reactions to yield a final concentration of 10 µM dTTP, 10 µM dCTP, 10 µM dGTP, 200 µM ddATP, and 0.2 units/µL of Klenow DNA polymerase exo (–). The PPA reactions were allowed to proceed at 37° C. for 10 min, and analyzed by denaturing gel electrophoresis. A FAM labeled primer (SEQ ID NO: 51) was used to locate the position of the edit.

FIG. 35 shows a clear difference in the gel banding pattern observed for APOBEC3A with and without spycatcher fusion. Without spycatcher and spytag, each of the seven C's is equally edited as shown by the edited (stalled) bands of various size. In the presence of both, only the primer+2 and +7 bands accumulate over time, indicating the confined reach of the enzyme. The accumulation of these abortive products was more pronounced when Spytag is attached to the proximal position.

This example demonstrates the first example of forcing site-specific deamination by tethering APOBEC3A to a reaction site via Spytag/Spycatcher.

Example 22: Two-Plex Targeted Tagmentation of DNA/RNA Heteroduplexes

In this example, RNA modification specific barcoding is facilitated by targeted tagmentation. This is achieved by conjugating tagmentation capable mosaic end (ME) adapters to an RNA specific antibody. After binding of the antibody to an RNA modification, active transposomes are assembled in situ by loading Tn5 transposase onto the antibody tethered ME adapters. This targets transposase to the modification site and allows for site specific tagmentation, thereby inserting barcoded adapters adjacent to the modification.

Figure 36:
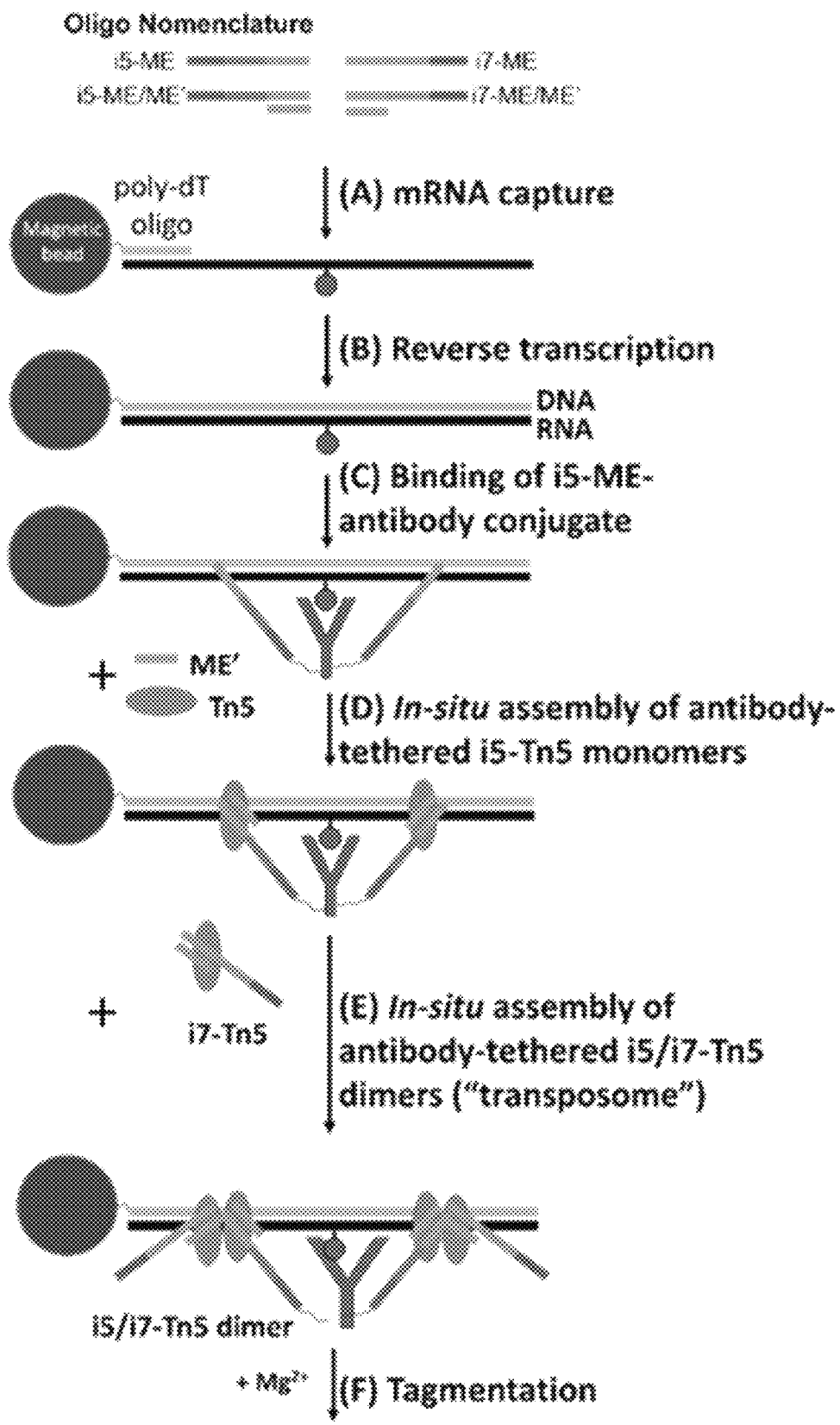
FIG. 36 Is a schematic showing barcoding facilitated by targeted tagmentation. Sequences are captured on magnetic beads via sequence specific hybridization probes (Step A). Captured RNA is reverse transcribed (Step B). Individual or a pool of differently barcoded i5-ME-antibody conjugates are added to immobilized RNA/DNA duplexes and incubated to reach saturated binding (Step C). Next, functional transposomes are assembled in situ: In a first step, antibody-tethered i5-Tn5 monomer is generated by adding free Tn5 transposase and ME' oligo to the surface bound i5-ME-antibody conjugates (Step D). Tn5 binds to the now double-stranded i5-ME/ME' adapter. In a second step, Tn5 preloaded with i7-ME/ME' adapter is added, resulting in i5-/i7-Tn5 dimers (Step E). After transposome assembly, tagmentation is initiated by adding an MgCl$_2$ containing buffer (Step F) and products with barcoded adapters are formed.

A m6A specific antibody is modified with two barcoded i5-ME sequences (i5-ME-BC1), and a m5C specific antibody is conjugated to two other i5-ME sequence (i5-ME-BC2) using site click chemistry (Example 4). Modified control RNA templates are generated by in vitro transcription of plasmid DNA with T7 RNA polymerase. A 2000 bp PCR amplicon of the PhiX genome (NEB, cat. no. N3023S) is transcribed in the presence of m6A triphosphate, and a 2000 bp PCR amplicon of M13mp18 Single-stranded DNA (NEB, cat. no. N4040S) is transcribed in the presence of m5C triphosphate. Both sequences are captured on magnetic beads via sequence specific hybridization probes (FIG. 36, Step A). Captured RNA is reverse transcribed using the capture probe as a primer for SuperScript II reverse transcriptase (FIG. 36, Step B). Individual or a pool of differently barcoded i5-ME-antibody conjugates are added to the immobilized RNA/DNA duplexes and incubated to reach saturated binding (FIG. 36, Step C). Next, functional transposomes are assembled in situ: In a first step, antibody-tethered i5-Tn5 monomer is generated by adding free Tn5 and ME' oligo to the surface bound i5-ME-antibody conjugates (FIG. 36, Step D). Tn5 binds to the now double-stranded i5-ME/ME' adapter. In a second step, Tn5 pre-loaded with i7-ME/ME' adapter is added, resulting in i5-/i7-Tn5 dimers (FIG. 36, Step E). After transposome assembly, tagmentation is initiated by adding an $MgCl_2$ containing buffer (FIG. 36, Step F) and products with barcoded adapters are formed as shown in FIG. 15A-15D. Tagmentation releases the RNA/DNA fragments from the bead and the size profile of the supernatant is analyzed by capillary electrophoresis before and after PCR. Sequencing and alignment of the obtained reads to the PhiX or the M13 genome confirms that m5C specific barcodes are correctly assigned to M13 reads, and m6A specific barcodes are correctly assigned to PhiX reads. Thus, this process allows for detection of one or more RNA modifications in a single reaction by means of targeted tagmentation.

NUMBERED EMBODIMENTS

Notwithstanding the appended claims, the following numbered embodiments also form part of the instant disclosure.

1. A nucleic acid-binding molecule comprising:
   i) a binding domain, and
   ii) an adapter,
   wherein the binding domain binds specifically to a non-canonical feature of a DNA or an RNA;
   wherein the adapter comprises a nucleic acid barcode sequence unique to the non-canonical feature bound specifically by the binding domain.
2. The nucleic acid-binding molecule of embodiment 1, wherein the binding domain comprises an antibody, a nanobody, an aptamer, a reader protein, a writer protein, an eraser protein, an engineered macromolecule scaffold, an engineered protein scaffold, or a selective covalent capture reagent, or a fragment or derivative thereof.
3. The nucleic acid-binding molecule of embodiment 2, wherein the reader protein is NUDT16 or YTHDC2, or a fragment or derivative thereof.
4. The nucleic acid-binding molecule of embodiment 2, wherein the writer protein is DNTM1, DNTM3A/B, NAT10, METTL3, METTL8, METTL14, METTL16, TRM, BMT, DUS2, PUS, or NSUN2, or a fragment or derivative thereof.
5. The nucleic acid-binding molecule of embodiment 2, wherein the eraser protein is FTO, ALKBH3, or ALKBH5, or a fragment or derivative thereof.
6. The nucleic acid-binding molecule of embodiment 2, wherein the binding domain does not have catalytic activity.
7. The nucleic acid-binding molecule of any one of embodiments 1-6, wherein the adapter is cleavable.
8. The nucleic acid-binding molecule of any one of embodiments 1-7, wherein the adapter comprises at least one of a universal forward primer (UFP) and a universal reverse primer (URP).
9. The nucleic acid-binding molecule of any one of embodiments 1-8, wherein the adapter comprises a unique molecular identifier (UMI).
10. The nucleic acid-binding molecule of any one of embodiments 1-9, wherein the non-canonical feature is a modified nucleoside.
11. The nucleic acid-binding molecule of embodiment 10, wherein the modified nucleoside is 3-methylcytidine (m3C), 5-methylcytidine (m5C), N4-acetylcytidine (ac4C), Pseudouridine (Ψ), 1-methyladenosine (m1A), N6-methyladenosine (m6A), Inosine (I), 7-methylguanosine (m7G), Dihydrouridine (D), 3-methyluridine (m3U), 5-methyluridine (m5U), 1-methylguanosine (m1G), N2-methylguanosine (m2G), 5-methyldeoxycytidine (m5dC), N4-methyldeoxycytidine, 5-hydroxymethylcytidine (5-hmC), 5-hydroxymethyldeoxycytidine (5hmdC), 5-carboxydeoxycytidine (5cadC), 5-formylcytidine (5fC), 5-formyldeoxycytidine (5fdC), 6-methyldeoxyadenosine, N7-methylguanosine (m7G), 2,7,2'-methylguanosine, or ribose methylation (Nm).
12. The nucleic acid-binding molecule of any one of embodiments 1-9, wherein the non-canonical feature is a nucleic acid lesion.
13. The method of embodiment 12, wherein the nucleic acid lesion results from an oxidative process or contact with ultra-violet light.
14. The method of embodiment 12, wherein the nucleic acid lesion results from bulky adduct formation or base alkylation by exogeneous agents.
15. The nucleic acid-binding molecule of embodiment 12, wherein the lesion is 8-oxo-guanine (8-oxoG), one or more abasic sites, cis-platin crosslinks, benzo(a)pyrene diol epoxide (BPDE)-adducts, cyclobutene pyrimidine dimers (CPD), pyrimidine-pyrimidone (6-4) photoproduct (6-4PP), 6-O-methylguanine ($O^6$-MedG), or O6-(Carboxymethyl)-2'-deoxyguanosine (O6-CMdG).
16. The nucleic acid-binding molecule of any one of embodiments 1-9, wherein the non-canonical feature is a structural element.
17. The nucleic acid-binding molecule of embodiment 16, wherein the structural element is a hairpin, loop, Z-DNA structure, G-quadruplex, triplex, i-motif, bulge, triplex, three-way junction, cruciform structure, tetraloop, ribose zipper, or pseudoknot.
18. The nucleic acid-binding molecule of any one of embodiments 1-17, wherein the binding domain contacts at least one-modified nucleoside.
19. The nucleic acid-binding molecule of any one of the embodiments 1-18, wherein the binding domain contacts a modified nucleoside and one or more nucleotides adjacent thereto.
20. The nucleic acid-binding molecule of anyone of embodiments 1-19, wherein the adapter comprises a linker, and the binding domain is coupled to the linker.
21. The nucleic acid-binding molecule of any one of embodiments 1-20, wherein the nucleic acid-binding molecule additionally comprises an enzyme or a catalytic fragment or derivative thereof.
22. The nucleic acid-binding molecule of embodiment 21, wherein the enzyme is a base editing enzyme.
23. The nucleic acid-binding molecule of embodiment 22, wherein the base editing enzyme is a cytosine deaminase or an adenosine deaminase.
24. The nucleic acid-binding molecule of embodiment 23, wherein in the base editing enzyme is APOBEC1 or APOBEC3A, or a catalytic fragment or derivative thereof.
25. The nucleic acid binding molecule of embodiment 23, wherein the enzyme is a DNA or RNA methylase or a pseudouridine synthase, or a catalytic fragment or derivative thereof.
26. The nucleic acid binding molecule of embodiment 21, wherein the enzyme is a DNA N-glycosylase or RNA N-glycosylase.
27. The nucleic acid-binding molecule of embodiment 21, wherein the enzyme is a transposase or an integrase.
28. The nucleic acid-binding molecule of embodiment 21, wherein the enzyme lacks catalytic activity.
29. A conjugate comprising a binding domain and an enzyme or fragment thereof, wherein the binding domain binds to the nucleic acid-binding molecule of any one of embodiments 1-28.
30. The conjugate of embodiment 29, wherein the binding domain and the enzyme of fragment thereof are covalently conjugated.
31. The conjugate of embodiment 29, wherein the binding domain and the enzyme or fragment thereof are non-covalently conjugated.
32. The conjugate of any one of embodiments 29-31, wherein the enzyme is Tn5 transposase.
33. The conjugate of embodiment 32, wherein the tagmentase is fused with protein A, G, or L.
34. A conjugate comprising (i) the nucleic acid binding molecule of any one of embodiments 1-28, further comprising a peptide tag, and (ii) an enzyme or fragment thereof fused to a protein tag that can covalently react with the peptide tag.

35. A conjugate comprising (i) the nucleic acid binding molecule of any one of embodiments 1-28, further comprising a protein tag, and (ii) an enzyme or fragment thereof fused to a peptide tag that can covalently react with the protein tag.

36. The conjugate of any one of embodiments 34-35, wherein the peptide tag is a Spytag.

37. The conjugate of any one of embodiments 34-36, wherein the enzyme is a deaminase and is fused to a Spycatcher protein.

38. A conjugate comprising (i) the nucleic acid binding molecule of any one of embodiments 1-28 and (ii) an enzyme or fragment thereof fused to a protein that can bind with high affinity to specific regions of the binding domain.

39. The conjugate of embodiment 38, wherein the binding domain is an IgG antibody or fragment thereof.

40. The conjugate of embodiment 39, wherein the enzyme is a deaminase fused to protein A, G or L.

41. A conjugate comprising (i) the nucleic acid binding molecule of any one of embodiments 1-28, further comprising a nucleic acid tag, and (ii) an enzyme or fragment thereof fused to a complementary nucleic acid tag that can hybridize to the nucleic acid tag of the nucleic acid binding molecule.

42. A complex comprising the nucleic acid-binding molecule of any one of embodiments 1-28 bound to a target nucleic acid.

43. The complex of embodiment 42, wherein the nucleic acid-binding molecule and the target nucleic acid are covalently linked.

44. A substrate coupled to the nucleic acid-binding molecule of any one of embodiments 1-28.

45. The substrate of embodiment 44, wherein the substrate is a bead, chip, plate, slide, dish, or 3-dimensional matrix.

46. The substrate of embodiment 45, wherein the nucleic acid-binding molecule is coupled to a surface of the substrate.

47. The substrate of embodiment 46, wherein the nucleic acid-binding molecule is coupled to the surface of the substrate indirectly via a capture molecule, wherein the capture molecule is coupled directly to the substrate.

48. The substrate of embodiment 47, wherein the capture molecule binds the nucleic acid-binding molecule.

49. The substrate of embodiment 47, wherein the capture molecule binds the target nucleic acid.

50. The substrate of embodiment 47, wherein the nucleic acid binding molecule binds to the target nucleic acid, which is bound to the capture molecule.

51. The substrate of any one of embodiments 44-50, wherein the nucleic acid-binding molecule is spatially separated from a second nucleic acid-binding molecule on a surface of the substrate.

52. A polymer coupled to the nucleic acid-binding molecule of any one of embodiments 1-28.

53. A method for making the nucleic acid-binding molecule of any one of embodiments 1-28, the method comprising coupling the binding domain to the adapter, to form a binding domain-adapter conjugate.

54. A method for analyzing a plurality of target nucleic acids, the method comprising:
(i) contacting the target nucleic acids with the nucleic acid-binding molecule of any one of embodiments 1-28;
(ii) either (a) transferring the nucleic acid barcode to the target nucleic acids to generate barcoded target nucleic acids, in an environment that substantially prevents off-target generation of barcoded nucleic acids, or (b) generating barcoded copies of the target nucleic acids;
(iii) modifying the barcoded target nucleic acids or the barcoded copies thereof, such that the position of the non-canonical feature is identifiable based on the primary nucleic acid sequence of the barcoded target nucleic acids, or the barcoded copies thereof; and
(iv) sequencing the barcoded target nucleic acids.

55. The method of embodiment 54, comprising appending a short nucleic acid sequence to the 3' end of the target nucleic acid before step (i) to facilitate barcode transfer.

56. The method of embodiment 54, wherein steps (i)-(iii) are repeated at least once.

57. The method of embodiment 56, wherein a different nucleic acid-binding molecule is used each time steps (i)-(iii) are repeated.

58. The method of embodiment 56, wherein the same nucleic acid-binding molecule is used each time steps (i)-(iii) are repeated.

59. The method of embodiment 21, wherein the nucleic acid barcode is transferred to the target nucleic acid enzymatically by single stranded ligation, splint ligation, primer extension, or double-stranded ligation.

60. The method of embodiment 59, wherein the nucleic acid barcode is transferred to the target nucleic acid by primer extension, wherein primer extension is preceded by ligating a nucleic acid with a universal sequence to the 3' end of the target nucleic acid.

61. The method of embodiment 60, wherein the nucleic acid barcode is transferred to the target RNA by primer extension, wherein primer extension is preceded by tailing the 3' end of the target nucleic acid enzymatically with *E. coli* poly (A) polymerase or poly(U) polymerase of *Schizosaccharomyces pombe* Cid1, in conjunction with one type of ribonucleotide and a competing complementary poly-dT, poly-dA, poly-dG, or poly-dC oligonucleotide.

62. The method of any one of embodiments 54-61, comprising amplifying the barcoded target nucleic acids or copies thereof prior to sequencing.

63. The method of any one of embodiments 54-61, wherein the target nucleic acids comprise DNAs, RNAs, or a mixture thereof.

64. The method of any one of embodiments 54-63, wherein the target nucleic acids comprise at least one non-canonical feature.

65. The method of embodiment 64, wherein the non-canonical feature is a modified nucleoside.

66. The method of embodiment 61, wherein the modified nucleoside is 3-methylcytidine (m3C), 5-methylcytidine (m5C), $N^4$-acetylcytidine (ac4C), Pseudouridine (Ψ), 1-methyladenosine (m1A), $N^6$-methyladenosine (m6A), Inosine (I), 7-methylguanosine (m7G), Dihydrouridine (D), 3-methyluridine (m3U), 5-methyluridine (m5U), 1-methylguanosine (m1G), $N^2$-methylguanosine (m2G), 5-methyldeoxycytidine (m5dC), $N^4$-methyldeoxycytidine, 5-hydroxymethylcytidine (5-hmC), 5-hydroxymethyldeoxycytidine (5hmdC), 5-carboxydeoxycytidine (5cadC), 5-formylcytidine (5fC), 5-formyldeoxycytidine (5fdC), 6-methyldeoxyadenosine, $N^7$-methylguanosine (m7G), 2,7,2'-methylguanosine, or ribose methylation (Nm).

67. The method of embodiment 64, wherein the non-canonical feature is a nucleic acid lesion.

68. The method of embodiment 67, wherein the nucleic acid lesion results from an oxidative process or contact with ultra-violet light.

69. The method of embodiment 67, wherein the nucleic acid lesion results from bulky adduct formation or base alkylation by exogeneous agents.

70. The nucleic acid-binding molecule of embodiment 64, wherein the lesion is 8-oxo-guanine (8-oxoG), one or more abasic sites, cis-platin crosslinks, benzo(a)pyrene diol epoxide (BPDE)-adducts, cyclobutene pyrimidine dimers (CPD), pyrimidine-pyrimidone (6-4) photoproduct (6-4PP), 6-O-methylguanine ($O^6$-MedG), or O6-(Carboxymethyl)-2'-deoxyguanosine (O6-CMdG).

71. The method of embodiment 64, wherein the non-canonical feature is a structural element.

72. The method of embodiment 71, wherein the structural element is a hairpin, loop, Z-DNA structure, G-quadruplex, triplex, i-motif, bulge, triplex, three-way junction, cruciform structure, tetraloop, ribose zipper, or pseudoknot.

73. The method of any one of embodiments 54-72, wherein the nucleic acid-binding molecule is coupled to the surface of a substrate and is spatially separated from other nucleic acid-binding molecules, such that each target nucleic acid can only contact one target nucleic acid-binding molecule.

74. The method of any one of embodiments 54-73, wherein the nucleic acid barcode is transferred to the target nucleic acid by covalently coupling the barcode or its complement to the 5' or 3' end of the target nucleic acid.

75. The method of any one of embodiments 54-73, wherein the nucleic acid barcode is transferred to the target nucleic acid enzymatically by single stranded ligation, splint ligation, primer extension, or double-stranded ligation.

76. The method of any one of embodiments 54-73, wherein the nucleic acid barcode is transferred to the target nucleic acid by chemical ligation.

77. The method of any one of embodiments 54-76, wherein the modifying comprises photochemically or chemically linking the nucleic acid-binding molecule to the target nucleic acid.

78. The method of any one of embodiments 54-77, wherein the binding domain displays a chemical cross-linking moiety in an orientation that facilitates covalent reaction with the nucleic acid target.

79. The method of any one of embodiments 54-77, wherein the modifying comprises editing a base at or near the site where the nucleic acid-binding molecule is bound to the target nucleic acid.

80. A method for detecting and or quantifying two or more non-canonical features in plurality of target nucleic acids, the method comprising:
  (i) contacting the target nucleic acids with at least two nucleic acid-binding molecules, wherein each nucleic acid-binding molecule comprises a binding domain and an adapter;
  wherein the binding domain of each nucleic acid-binding molecule binds to a different non-canonical feature of a DNA or an RNA; wherein the adapter comprises a nucleic acid barcode sequence unique to the non-canonical feature bound specifically by each binding domain;
  (ii) either (a) transferring the nucleic acid barcode to the target nucleic acids to generate barcoded target nucleic acids, in an environment that substantially prevents off-target generation of barcoded nucleic acids, or (b) generating barcoded copies of the target nucleic acids;
  (iii) modifying the barcoded target nucleic acids or the barcoded copies thereof, such that the position of the non-canonical feature is identifiable based on the primary nucleic acid sequence of the barcoded target nucleic acids, or the barcoded copies thereof; and
  (vi) sequencing the barcoded target nucleic acids.

81. The method of embodiment 80, comprising amplifying the barcoded target nucleic acids or copies thereof prior to sequencing.

82. The method of embodiment 80 or 81, wherein the target nucleic acids comprise DNAs, RNAs, or a mixture thereof.

83. The method of any one of embodiments 80-82, wherein at least one of the non-canonical features is a modified nucleoside.

84. The method of embodiment 83, wherein the modified nucleoside is 3-methylcytidine (m3C), 5-methylcytidine (m5C), $N^4$-acetylcytidine (ac4C), Pseudouridine (Ψ), 1-methyladenosine (m1A), $N^6$-methyladenosine (m6A), Inosine (I), 7-methylguanosine (m7G), Dihydrouridine (D), 3-methyluridine (m3U), 5-methyluridine (m5U), 1-methylguanosine (m1G), $N^2$-methylguanosine (m2G), 5-methyldeoxycytidine (m5dC), $N^4$-methyldeoxycytidine, 5-hydroxymethylcytidine (5-hmC), 5-hydroxymethyldeoxycytidine (5hmdC), 5-carboxydeoxycytidine (5cadC), 5-formylcytidine (5fC), 5-formyldeoxycytidine (5fdC), 6-methyldeoxyadenosine, $N^7$-methylguanosine (m7G), 2,7,2'-methylguanosine, or ribose methylation (Nm).

85. The method of embodiment 82, wherein the non-canonical feature is a nucleic acid lesion.

86. The method of embodiment 85, wherein the nucleic acid lesion results from an oxidative process or contact with ultra-violet light.

87. The method of embodiment 85, wherein the nucleic acid lesion results from bulky adduct formation or base alkylation by exogeneous agents.

88. The nucleic acid-binding molecule of embodiment 82, wherein the lesion is 8-oxo-guanine (8-oxoG), one or more abasic sites, cis-platin crosslinks, benzo(a)pyrene diol epoxide (BPDE)-adducts, cyclobutene pyrimidine dimers (CPD), pyrimidine-pyrimidone (6-4) photoproduct (6-4PP), 6-O-methylguanine ($O^6$-MedG), or O6-(Carboxymethyl)-2'-deoxyguanosine (O6-CMdG).

89. The method of any one of embodiments 80-82, wherein at least one of the non-canonical features is a structural element.

90. The method of embodiment 89, wherein the structural element is a hairpin, loop, Z-DNA structure, G-quadruplex, triplex, i-motif, bulge, triplex, three-way junction, cruciform structure, tetraloop, ribose zipper, or pseudoknot.

91. The method of any one of embodiments 80-90, wherein the nucleic acid-binding molecules are coupled to the surface of a substrate and are spatially separated such that each target nucleic acid can contact only one target nucleic acid-binding molecule.

92. The method of any one of embodiments 80-91, wherein the nucleic acid barcode is transferred to the target nucleic acids by covalently coupling the barcode or its complement to the 5' or 3' end of the target nucleic acids.

93. The method of any one of embodiments 80-91, wherein the nucleic acid barcode is transferred to the target nucleic acids enzymatically by single stranded ligation, splint ligation, primer extension, or double-stranded ligation.

94. The method of any one of embodiments 80-90, wherein the nucleic acid barcode is transferred to the target nucleic acids by chemical ligation.

95. The method of any one of embodiments 80-94, wherein the modifying comprises photochemically linking the nucleic acid-binding molecule to the target nucleic acids.

96. The method of any one of embodiments 80-94, wherein the modifying comprises editing a base at or near the site where the nucleic acid-binding molecule is bound to the target nucleic acids.

97. A method for detecting a non-canonical feature in a target nucleic acid, the method comprising:
(i) contacting the target nucleic acid with a nucleic acid-binding molecule of any one of embodiments 1-28;
(ii) either (a) transferring the nucleic acid barcode to the target nucleic acids to generate barcoded target nucleic acid, in an environment that substantially prevents off-target generation of barcoded nucleic acids; and
(iii) detecting the presence of the barcode in the target nucleic acid or copy thereof.

98. The method of embodiment 97, wherein the non-canonical feature is a modified nucleoside.

99. The method of embodiment 98, wherein the modified nucleoside is 3-methylcytidine (m3C), 5-methylcytidine (m5C), $N^4$-acetylcytidine (ac4C), Pseudouridine ($\Psi$), 1-methyladenosine (m1A), $N^6$-methyladenosine (m6A), Inosine (I), 7-methylguanosine (m7G), Dihydrouridine (D), 3-methyluridine (m3U), 5-methyluridine (m5U), 1-methylguanosine (m1G), $N^2$-methylguanosine (m2G), 5-methyldeoxycytidine (m5dC), $N^4$-methyldeoxycytidine, 5-hydroxymethylcytidine (5-hmC), 5-hydroxymethyldeoxycytidine (5hmdC), 5-carboxydeoxycytidine (5cadC), 5-formylcytidine (5fC), 5-formyldeoxycytidine (5fdC), 6-methyldeoxyadenosine, $N^7$-methylguanosine (m7G), 2,7,2'-methylguanosine, or ribose methylation (Nm).

100. The method of embodiment 97, wherein the non-canonical feature is a nucleic acid lesion.

101. The method of embodiment 100, wherein the nucleic acid lesion results from an oxidative process or contact with ultra-violet light.

102. The method of embodiment 100, wherein the nucleic acid lesion results from bulky adduct formation or base alkylation by exogeneous agents.

103. The method of embodiment 100, wherein the lesion is 8-oxo-guanine (8-oxoG), one or more abasic sites, cis-platin crosslinks, benzo(a)pyrene diol epoxide (BPDE)-adducts, cyclobutene pyrimidine dimers (CPD), pyrimidine-pyrimidone (6-4) photoproduct (6-4PP), 6-O-methylguanine ($O^6$-MedG), or O6-(Carboxymethyl)-2'-deoxyguanosine (O6-CMdG).

104. The method of embodiment 100, wherein the non-canonical feature is a structural element.

105. The method of claim 104, wherein the structural element is a hairpin, loop, Z-DNA structure, G-quadruplex, triplex, i-motif, bulge, triplex, three-way junction, cruciform structure, tetraloop, ribose zipper, or pseudoknot.

106. The method of any one of embodiments 97-105, wherein the transferring comprises covalently coupling the barcode or its complement to the 5' or 3' end of the target nucleic acid.

107. The method of any one of embodiments 97-105, wherein the nucleic acid barcode is transferred to the target nucleic acid by single stranded ligation, splint ligation, splint extension, template extension, or double-stranded ligation.

108. The method of any one of embodiments 97-105, wherein the nucleic acid barcode is transferred to the target nucleic acid by chemical ligation.

109. The method of any one of embodiments 97-108, wherein steps (i)-(iii) are repeated at least once.

110. The method of any one of embodiments 97-109, wherein detecting the presence of the barcode comprises modifying the barcoded target nucleic acids or the barcoded copy thereof.

111. The method of any one of embodiments 97-109, wherein detecting the presence of the barcode comprises amplifying the barcoded target nucleic acid or copy thereof.

112. The method of any one of embodiments 97-109, wherein detecting the presence of the barcode comprises sequencing the barcoded target nucleic acid.

113. A method for determining the location of a non-canonical feature in a target nucleic acid near or at a single base resolution, the method comprising:
(i) contacting the target nucleic acid with a nucleic acid-binding molecule of any one of embodiments 1-28;
(ii) transferring the nucleic acid barcode to the target nucleic acids to generate barcoded target nucleic acids, in an environment that substantially prevents off-target generation of barcoded nucleic acids; and
(iii) detecting the presence of the barcode in the target nucleic acid or copy thereof;
wherein the nucleic acid-binding molecule comprises a binding domain capable of one or more of the following:
(a) inducing a mutation in the target nucleic acid; or
(b) preventing polymerase bypass and therefore causing truncation during copying of the target nucleic acid.

114. The method of embodiment 113, wherein preventing polymerase bypass comprises chemically or photochemically linking the nucleic acid-binding molecule to the target nucleic acid.

115. The method of embodiment 113, wherein preventing polymerase bypass comprises chemically modifying the binding domain to induce truncation during copying of the target nucleic acid.

116. The method of any one of embodiments 113-115, wherein the non-canonical feature is a modified nucleoside.

117. The method of embodiment 116, wherein the modified nucleoside is 3-methylcytidine (m3C), 5-methylcytidine (m5C), $N^4$-acetylcytidine (ac4C), Pseudouridine ($\Psi$), 1-methyladenosine (m1A), $N^6$-methyladenosine (m6A), Inosine (I), 7-methylguanosine (m7G), Dihydrouridine (D), 3-methyluridine (m3U), 5-methyluridine (m5U), 1-methylguanosine (m1G), $N^2$-methylguanosine (m2G), 5-methyldeoxycytidine (m5dC), $N^4$-methyldeoxycytidine, 5-hydroxymethylcytidine (5-hmC), 5-hydroxymethyldeoxycytidine (5hmdC), 5-carboxydeoxycytidine (5cadC), 5-formylcytidine (5fC), 5-formyldeoxycytidine (5fdC), 6-methyldeoxyadenosine, $N^7$-methylguanosine (m7G), 2,7,2'-methylguanosine, or ribose methylation (Nm).

118. The method of any one of embodiments 113-115, wherein the non-canonical feature is a nucleic acid lesion.

119. The method of embodiment 118, wherein the nucleic acid lesion results from oxidative process or contact with ultra-violet light.

120. The method of embodiment 118, wherein the nucleic acid lesion results from bulky adduct formation or base alkylation by exogeneous agents.

121. The method of embodiment 118, wherein the lesion is 8-oxo-guanine (8-oxoG), one or more abasic sites, cis-platin crosslinks, benzo(a)pyrene diol epoxide (BPDE)-adducts, cyclobutene pyrimidine dimers (CPD), pyrimidine-pyrimidone (6-4) photoproduct (6-4PP), 6-O-methylguanine ($O^6$-MedG), or O6-(Carboxymethyl)-2'-deoxyguanosine (O6-CMdG).

122. The method of any one of embodiments 113-115, wherein the non-canonical feature is a structural element.

123. The method of embodiment 122, wherein the structural element is a hairpin, loop, Z-DNA structure, G-quadruplex, triplex, i-motif, bulge, triplex, three-way junction, cruciform structure, tetraloop, ribose zipper, or pseudoknot.

124. The method of any one of embodiments 113-123, wherein the transferring comprises covalently coupling the barcode or its complement to the 5' or 3' end of the target nucleic acid.

125. The method of any one of embodiments 113-123, wherein steps (i)-(iii) are repeated at least once.

126. The method of embodiment 124, wherein a different nucleic acid-binding molecule is used each time steps (i)-(iii) are repeated.

127. The method of embodiment 124, wherein the same nucleic acid-binding molecule is used each time steps (i)-(iii) are repeated.

128. The method of any one of embodiments 113-127, wherein detecting the presence of the barcode comprises modifying the barcoded target nucleic acid or the barcoded copy thereof.

129. The method of any one of embodiments 113-127, wherein detecting the presence of the barcode comprises amplifying the barcoded target nucleic acid or copy thereof.

130. The method of any one of embodiments 113-127, wherein detecting the presence of the barcode comprises sequencing the barcoded target nucleic acid.

131. The method of any one of embodiments 113-127, wherein detecting the presence of the barcode comprises sequencing the nucleic acid and the adapter of the nucleic acid-binding molecule.

132. The method of any one of embodiments 113-131, wherein transferring the nucleic acid barcode to the target nucleic acid comprises covalently coupling the barcode or its complement to the 5' or 3' end of the target nucleic acid.

What is claimed is:

1. A method for detecting one or more non-canonical features of RNA in a plurality of target nucleic acids, the method comprising:
   (a) contacting the target nucleic acids with a nucleic acid-binding molecule comprising:
      a binding domain, and
      an adapter,
   wherein the binding domain binds specifically to a non-canonical feature of an RNA; and
   wherein the adapter comprises a nucleic acid barcode sequence unique to the non-canonical feature bound specifically by the binding domain;
   (b) transferring the nucleic acid barcode of the adapter to the target nucleic acids to generate barcoded target nucleic acids, in an environment that substantially prevents off-target generation of barcoded nucleic acids; and
   (c) sequencing the barcoded target nucleic acids,
   wherein the nucleic acid-binding molecule is coupled to a surface of a substrate and is spatially separated from other nucleic acid-binding molecules, such that each target nucleic acid can only contact one nucleic acid-binding molecule, or wherein the target nucleic acids are coupled to the surface of the substrate and each coupled target nucleic acid is spatially separated from other target nucleic acids, such that each coupled target nucleic acid can only contact one nucleic acid-binding molecule, and
   wherein the nucleic acid barcode is transferred to the target nucleic acid enzymatically by single stranded ligation, splint ligation, primer extension, reverse transcription, or double-stranded ligation.

2. The method of claim 1, wherein the binding domain comprises an antibody, an aptamer, a reader protein, a writer protein, an eraser protein, an engineered macromolecule scaffold, an engineered protein scaffold, or a selective covalent capture reagent, or a fragment or derivative thereof.

3. The method of claim 2, wherein the antibody comprises an IgG antibody, an antigen-binding fragment (Fab), a single chain variable fragment (scFv), a heavy or light chain single domain (VH and VL), a heavy-chain antibody (hcAb), or the VHH domain of a hcAb (nanobody), and
   wherein the engineered protein scaffold comprises an adnectin, an affibody, an affilin, an anticalin, an atrimer, an avimer, a bicyclic peptide, a centyrin, a cys-knot, a darpin, a fynomer, a kunitz domain, an obody or a pronectin scaffold.

4. The method of claim 2, wherein the reader protein is selected from YTHDC1, YTHDC2, YTHDF1, YTHDF2, YTHDF3, or a combination thereof.

5. The method of claim 1, wherein the non-canonical feature of RNA is 3-methylcytidine (m3C), 5-methylcytidine (m5C), N4-acetylcytidine (ac4C), Pseudouridine (Ψ), 1-methyladenosine (m1A), N6-methyladenosine (m6A), Inosine (I), 7-methylguanosine (m7G), 7-methylguanosine (m7G)-Cap, Dihydrouridine (D), 3-methyluridine (m3U), 5-methyluridine (m5U), 1-methylguanosine (m1G), N2-methylguanosine (m2G), 5-methyldeoxycytidine (m5dC), N4-methyldeoxycytidine (4mdC), 5-hydroxymethylcytidine (5-hmC), 5-hydroxymethyldeoxycytidine (5hmdC), 5-carboxydeoxycytidine (5cadC), 5-carboxycytidine (5caC), 5-formylcytidine (5fC), 5-formyldeoxycytidine (5fdC), 6-methyldeoxyadenosine, N7-methylguanosine (m7G), 2,7,2'-methylguanosine, or ribose methylation (Nm), 2,N2-dimethyl guanosine (m22G), 5-carbamoylmethyl-2'-O-methyluridine (ncm5Um), 5-methoxycarbonylmethyluridine (ncm5mU), 5-methoxycarbonylmethyl-2-thiouridine (mcm5s2U), queuosine (Q), 2-thiouridine (s2U), 5-taurinomethyluridine (τm5U), 5-taurinomethyl-2-thiouridine (τm5s2U), N6-isopentenyladenosine (I6A), 2-methylthio-N6-threonyl carbamoyladenosine (ms2t6A).

6. A method for detecting one or more non-canonical features of RNA in a plurality of target nucleic acids, the method comprising:
   (a1) generating double-stranded DNA/RNA heteroduplexes by priming and reverse transcribing the plurality of target nucleic acids containing non-canonical features, wherein the reverse transcription is initiated by the addition of Mg2+, dNTPs and a reverse transcriptase;
   (b1) contacting the plurality of double-stranded DNA/RNA heteroduplexes with non-canonical features with one or more nucleic acid binding domain-transposase conjugates;
   (c1) transferring mosaic end adapters to the double-stranded DNA/RNA heteroduplexes by action of the transposases cutting the double-stranded DNA/RNA heteroduplexes and inserting two mosaic end adapters at the ends to generate barcoded target nucleic acids, wherein the barcoded target nucleic acids are generated in an environment that substantially prevents off-target generation of barcoded nucleic acids, wherein the transferring step is initiated by the addition of Mg2+; and
   (d1) sequencing the barcoded target nucleic acids;
   or
   (a2) contacting the plurality of target nucleic acids containing non-canonical features with one or more nucleic acid binding domain-transposase conjugates;
   (b2) generating double-stranded DNA/RNA heteroduplexes by priming and reverse transcribing the plurality of target nucleic acids containing non-canonical features, wherein the reverse transcription is initiated by the addition of Mg2+, dNTPs and a reverse transcriptase;

(c2) transferring mosaic end adapters to the double-stranded DNA/RNA heteroduplexes by action of the transposases cutting the double-stranded DNA/RNA heteroduplexes and inserting two mosaic end adapters at the ends to generate barcoded target nucleic acids, wherein the barcoded target nucleic acids are generated in an environment that substantially prevents off-target generation of barcoded nucleic acids, wherein the transferring step is initiated by the addition of Mg2+; and (d2) sequencing the barcoded target nucleic acids, wherein the nucleic acid binding domain-transposase conjugates are coupled to the surface of a substrate and are spatially separated from other nucleic acid binding domain-transposase conjugate molecules, such that each target nucleic acid can only contact one nucleic acid binding domain-transposase conjugate, and wherein the nucleic acid binding domain-transposase conjugates are not coupled to the surface of the substrate by a nucleic acid.

7. The method of claim 6, wherein the method comprises:
(i) steps (a1)-(d1) and (a2)-(d2) are conducted in the order specified;
(ii) steps (b2)-(c2) are conducted simultaneously and after step (a2); or
(iii) steps (a1)-(c1) are conducted simultaneously and steps (a2)-(c2) are conducted simultaneously.

8. The method of claim 6, wherein the binding domain comprises an antibody, an aptamer, a reader protein, a writer protein, an eraser protein, an engineered macromolecule scaffold, an engineered protein scaffold, or a selective covalent capture reagent, or a fragment or derivative thereof.

9. The method of claim 8, wherein the antibody comprises an IgG antibody, an antigen-binding fragment (Fab), a single chain variable fragment (scFv), a heavy or light chain single domain (VH and VL), a heavy-chain antibody (hcAb), or the VHH domain of a hcAb (nanobody), and wherein the engineered protein scaffold comprises an adnectin, an affibody, an affilin, an anticalin, an atrimer, an avimer, a bicyclic peptide, a centyrin, a cys-knot, a darpin, a fynomer, a kunitz domain, an obody or a pronectin scaffold.

10. The method of claim 8, wherein the reader protein is a protein selected from YTHDC1, YTHDC2, YTHDF1, YTHDF2, YTHDF3, or a combination thereof.

11. The method of claim 6, wherein the transposase molecules are covalently conjugated to the binding domain via genetic fusion, or via covalent peptide/protein tags.

12. The method of claim 6, wherein the transposase molecules are reversibly conjugated to the binding domain via a peptide linker comprising a protease cleavage site.

13. The method of claim 11, wherein the covalent peptide/protein tags are Spytag-Spycatcher.

14. The method of claim 6, where the plurality of target nucleic acids are derived from a single cell, or wherein the method for detecting one or more non-canonical features of RNA in a plurality of target nucleic acids takes place in permeated single cells or single cell nuclei.

15. The method of claim 6, wherein the non-canonical feature of RNA is 3-methylcytidine (m3C), 5-methylcytidine (m5C), N4-acetylcytidine (ac4C), Pseudouridine (Ψ), 1-methyladenosine (m1A), N6-methyladenosine (m6A), Inosine (I), 7-methylguanosine (m7G), 7-methylguanosine (m7G)-Cap, Dihydrouridine (D), 3-methyluridine (m3U), 5-methyluridine (m5U), 1-methylguanosine (m1G), N2-methylguanosine (m2G), 5-methyldeoxycytidine (m5dC), N4-methyldeoxycytidine (4mdC), 5-hydroxymethylcytidine (5-hmC), 5-hydroxymethyldeoxycytidine (5hmdC), 5-carboxydeoxycytidine (5cadC), 5-carboxycytidine (5caC), 5-formylcytidine (5fC), 5-formyldeoxycytidine (5fdC), 6-methyldeoxyadenosine, N7-methylguanosine (m7G), 2,7,2'-methylguanosine, or ribose methylation (Nm), 2,N2-dimethyl guanosine (m22G), 5-carbamoylmethyl-2'-O-methyluridine (ncm5Um), 5-methoxycarbonylmethyluridine (ncm5mU), 5-methoxycarbonylmethyl-2-thiouridine (mcm5s2U), queuosine (Q), 2-thiouridine (s2U), 5-taurinomethyluridine (Σm5U), 5-taurinomethyl-2-thiouridine (τm5s2U), N6-isopentenyladenosine (I6A), 2-methylthio-N6-threonyl carbamoyladenosine (ms2t6A).

* * * * *

```
                             SEQUENCE LISTING

Sequence total quantity: 60
SEQ ID NO: 1              moltype =    length =
SEQUENCE: 1
000

SEQ ID NO: 2              moltype =    length =
SEQUENCE: 2
000

SEQ ID NO: 3              moltype =    length =
SEQUENCE: 3
000

SEQ ID NO: 4              moltype =    length =
SEQUENCE: 4
000

SEQ ID NO: 5              moltype =    length =
SEQUENCE: 5
000

SEQ ID NO: 6              moltype = DNA  length = 21
FEATURE                   Location/Qualifiers
misc_feature              1
                          note = 5' preadenylation
modified_base             21
                          mod_base = OTHER
                          note = dideoxycytidine
source                    1..21
                          mol_type = other DNA
                          organism = synthetic construct
SEQUENCE: 6
agatcggaag agcggttcag n                                                    21

SEQ ID NO: 7              moltype =    length =
SEQUENCE: 7
000

SEQ ID NO: 8              moltype = DNA  length = 41
FEATURE                   Location/Qualifiers
misc_feature              1
                          note = 5' Phosphate
misc_difference           1..2
misc_difference           7..9
source                    1..41
                          mol_type = other DNA
                          organism = synthetic construct
SEQUENCE: 8
nnaaccnnna gatcggaaga gcgtcgtgga tcctgaaccg c                              41

SEQ ID NO: 9              moltype = DNA  length = 32
FEATURE                   Location/Qualifiers
```

```
misc_feature            1
                        note = PEG linker attached to 5' end
misc_feature            32
                        note = blocked 3' end
source                  1..32
                        mol_type = other DNA
                        organism = synthetic construct
SEQUENCE: 9
tataagagac agacacaggc cactcagtct at                                     32

SEQ ID NO: 10           moltype = AA  length = 13
FEATURE                 Location/Qualifiers
source                  1..13
                        mol_type = protein
                        organism = synthetic construct
SEQUENCE: 10
AHIVMVDAYK PTK                                                          13

SEQ ID NO: 11           moltype = AA  length = 6
FEATURE                 Location/Qualifiers
VARIANT                 3
VARIANT                 5
source                  1..6
                        mol_type = protein
                        organism = synthetic construct
SEQUENCE: 11
LCXPXR                                                                  6

SEQ ID NO: 12           moltype = AA  length = 139
FEATURE                 Location/Qualifiers
source                  1..139
                        mol_type = protein
                        organism = synthetic construct
SEQUENCE: 12
MSYYHHHHHH DYDIPTTENL YFQGAMVDTL SGLSSEQGQS GDMTIEEDSA THIKFSKRDE        60
DGKELAGATM ELRDSSGKTI STWISDGQVK DFYLYPGKYT FVETAAPDGY EVATAITFTV       120
NEQGQVTVNG KATKGDAHI                                                   139

SEQ ID NO: 13           moltype = DNA  length = 50
FEATURE                 Location/Qualifiers
misc_feature            1
                        note = FAM labelled
misc_feature            1..42
                        note = RNA
modified_base           29
                        mod_base = m6a
source                  1..50
                        mol_type = other DNA
                        organism = synthetic construct
misc_feature            43..50
                        note = DNA
SEQUENCE: 13
tcgtcggcag cgtcagatgc ataaggtcna tattaagtat agactgagtg                  50

SEQ ID NO: 14           moltype = DNA  length = 40
FEATURE                 Location/Qualifiers
misc_feature            1
                        note = FAM labelled
misc_feature            1..32
                        note = RNA
modified_base           25
                        mod_base = m5c
source                  1..40
                        mol_type = other DNA
                        organism = synthetic construct
misc_feature            33..40
                        note = DNA
SEQUENCE: 14
tcgtcggcag cgtcagatga tattngaagt atactgagtg                             40

SEQ ID NO: 15           moltype = DNA  length = 50
FEATURE                 Location/Qualifiers
misc_feature            1
                        note = FAM labelled
modified_base           29
                        mod_base = m5c
source                  1..50
                        mol_type = other DNA
                        organism = synthetic construct
```

```
SEQUENCE: 15
tcgtcggcag cgtcagatgc ataatctana tcttaagtat agactgagtg        50

SEQ ID NO: 16           moltype = DNA   length = 40
FEATURE                 Location/Qualifiers
misc_feature            1
                        note = FAM labelled
modified_base           25
                        mod_base = i
source                  1..40
                        mol_type = other DNA
                        organism = synthetic construct
SEQUENCE: 16
tcgtcggcag cgtcagatga tactngcagt atactgagtg                    40

SEQ ID NO: 17           moltype = RNA   length = 44
FEATURE                 Location/Qualifiers
misc_feature            1
                        note = FAM labelled
modified_base           29
                        mod_base = m6a
source                  1..44
                        mol_type = other RNA
                        organism = synthetic construct
SEQUENCE: 17
tcgtcggcag cgtcagatgc ataaggtcna tattaagtat agac               44

SEQ ID NO: 18           moltype = RNA   length = 34
FEATURE                 Location/Qualifiers
misc_feature            1
                        note = FAM labelled
modified_base           24
                        mod_base = m5c
source                  1..34
                        mol_type = other RNA
                        organism = synthetic construct
SEQUENCE: 18
cgtcggcagc gtcagatgat attngaagta tgac                          34

SEQ ID NO: 19           moltype =   length =
SEQUENCE: 19
000

SEQ ID NO: 20           moltype = DNA   length = 25
FEATURE                 Location/Qualifiers
misc_feature            25
                        note = 3' amine
source                  1..25
                        mol_type = other DNA
                        organism = synthetic construct
SEQUENCE: 20
catctgacgc tgccgacgat ttttt                                    25

SEQ ID NO: 21           moltype = DNA   length = 79
FEATURE                 Location/Qualifiers
source                  1..79
                        mol_type = other DNA
                        organism = synthetic construct
SEQUENCE: 21
tcgtcggcag cgtcagatga ttgtgttagg ctagtaagta gatggattag accgtcgagt   60
gagtagagta cgtagtgca                                            79

SEQ ID NO: 22           moltype = DNA   length = 32
FEATURE                 Location/Qualifiers
misc_feature            1
                        note = 5' phosphate modified
misc_feature            32
                        note = PEG linker attached to 3'end
source                  1..32
                        mol_type = other DNA
                        organism = synthetic construct
SEQUENCE: 22
tataagagac agacacaggc cactcagtct at                            32

SEQ ID NO: 23           moltype =   length =
SEQUENCE: 23
000

SEQ ID NO: 24           moltype = DNA   length = 18
```

```
FEATURE                 Location/Qualifiers
misc_feature            1
                        note = FAM labelled
misc_feature            1..10
                        note = RNA
source                  1..18
                        mol_type = other DNA
                        organism = synthetic construct
misc_feature            11..18
                        note = DNA
SEQUENCE: 24
ttaagtatag actgagtg                                                       18

SEQ ID NO: 25           moltype = DNA  length = 28
FEATURE                 Location/Qualifiers
misc_feature            1
                        note = PEG linker connected to 5' end
source                  1..28
                        mol_type = other DNA
                        organism = synthetic construct
SEQUENCE: 25
tataagagac agacacaggc cactcagt                                            28

SEQ ID NO: 26           moltype = DNA  length = 30
FEATURE                 Location/Qualifiers
misc_feature            1
                        note = PEG linker connected to 5' end
source                  1..30
                        mol_type = other DNA
                        organism = synthetic construct
SEQUENCE: 26
tataagagac agacacaggc cactcagtct                                          30

SEQ ID NO: 27           moltype = DNA  length = 32
FEATURE                 Location/Qualifiers
misc_feature            1
                        note = PEG linker connected to 5' end
source                  1..32
                        mol_type = other DNA
                        organism = synthetic construct
SEQUENCE: 27
tataagagac agacacaggc cactcagtct at                                       32

SEQ ID NO: 28           moltype =   length =
SEQUENCE: 28
000

SEQ ID NO: 29           moltype = DNA  length = 20
FEATURE                 Location/Qualifiers
misc_feature            1
                        note = 5' Phosphate
misc_difference         1..2
modified_base           20
                        mod_base = OTHER
                        note = dideoxycytidine
source                  1..20
                        mol_type = other DNA
                        organism = synthetic construct
SEQUENCE: 29
nnactgagtg gcctgtgtcn                                                     20

SEQ ID NO: 30           moltype = DNA  length = 30
FEATURE                 Location/Qualifiers
misc_feature            1
                        note = 5' Phosphate
misc_difference         1..2
modified_base           30
                        mod_base = OTHER
                        note = dideoxycytidine
source                  1..30
                        mol_type = other DNA
                        organism = synthetic construct
SEQUENCE: 30
nnactgagtg gcctgtgtct gtctcttatn                                          30

SEQ ID NO: 31           moltype = DNA  length = 52
FEATURE                 Location/Qualifiers
misc_feature            1
                        note = 5' Phosphate
```

```
misc_difference         1..2
modified_base           52
                        mod_base = OTHER
                        note = dideoxycytidine
source                  1..52
                        mol_type = other DNA
                        organism = synthetic construct
SEQUENCE: 31
nnactgagtg gcctgtgtct gtctcttata cacatctccg agcccacgag an        52

SEQ ID NO: 32           moltype = RNA  length = 40
FEATURE                 Location/Qualifiers
misc_feature            1
                        note = 5' FAM labelled
modified_base           30
                        mod_base = m6a
source                  1..40
                        mol_type = other RNA
                        organism = synthetic construct
SEQUENCE: 32
tcgtcggcag cgtcagatgc ctgcaaaggn ctgctttgac                      40

SEQ ID NO: 33           moltype = DNA  length = 28
FEATURE                 Location/Qualifiers
misc_feature            1
                        note = 5' Phosphate
misc_feature            21
                        note = RNA
misc_feature            28
                        note = PEG linker connected to 3' end
source                  1..28
                        mol_type = other DNA
                        organism = synthetic construct
misc_feature            1..20
                        note = DNA
misc_feature            22..28
                        note = DNA
SEQUENCE: 33
cggacacaga cagagaatat tatatata                                   28

SEQ ID NO: 34           moltype = AA  length = 442
FEATURE                 Location/Qualifiers
source                  1..442
                        mol_type = protein
                        organism = synthetic construct
SEQUENCE: 34
MSSETGPVAV DPTLRRRIEP HEFEVFFDPR ELRKETCLLY EINWGGRHSI WRHTSQNTNK  60
HVEVNFIEKF TTERYFCPNT RCSITWFLSW SPCGECSRAI TEFLSRYPHV TLFIYIARLY 120
HHADPRNRQG LRDLISSGVT IQIMTEQESG YCWRNFVNYS PSNEAHWPRY PHLWVRLYVL 180
ELYCIILGLP PCLNILRRKQ PQLTFFTIAL QSCHYQRLPP HILWATGLKG GSGGSGGSGG 240
SPHPVLEKLR SINNYNPKDF DWNLKHGRVF IIKSYSEDDI HRSIKYNIWC STEHGNKRLD 300
AAYRSMNGKG PVYLLFSVNG SGHFCGVAEM KSAVDYNTCA GVWSQDKWKG RFDVRWIFVK 360
DVPNSQLRHI RLENNENKPV TNSRDTQEVP LEKAKQVLKI IASYKHTTSI FDDFSHYEKR 420
QEEEESVKKE RQGRGKHHHH HH                                        442

SEQ ID NO: 35           moltype = AA  length = 254
FEATURE                 Location/Qualifiers
source                  1..254
                        mol_type = protein
                        organism = synthetic construct
SEQUENCE: 35
MSSETGPVAV DPTLRRRIEP HEFEVFFDPR ELRKETCLLY EINWGGRHSI WRHTSQNTNK  60
HVEVNFIEKF TTERYFCPNT RCSITWFLSW SPCGECSRAI TEFLSRYPHV TLFIYIARLY 120
HHADPRNRQG LRDLISSGVT IQIMTEQESG YCWRNFVNYS PSNEAHWPRY PHLWVRLYVL 180
ELYCIILGLP PCLNILRRKQ PQLTFFTIAL QSCHYQRLPP HILWATGLKG GSRGVPHIVM 240
VDAYKRYKHH HHHH                                                 254

SEQ ID NO: 36           moltype = AA  length = 320
FEATURE                 Location/Qualifiers
source                  1..320
                        mol_type = protein
                        organism = synthetic construct
SEQUENCE: 36
MVTTLSGLSG EQGPSGDMTT EEDSATHIKF SKRDEDGREL AGATMELRDS SGKTISTWIS  60
DGHVKDFYLY PGKYTFVETA APDGYEVATP IEFTVNEDGQ VTVDGEATEG DAHTGGGGSP 120
HPVLEKLRSI NNYNPKDFDW NLKHGRVFII KSYSEDDIHR SIKYNIWCST EHGNKRLDAA 180
YRSMNGKGPV YLLFSVNGSG HFCGVAEMKS AVDYNTCAGV WSQDKWKGRF DVRWIFVKDV 240
PNSQLRHIRL ENNENKPVTN SRDTQEVPLE KAKQVLKIIA SYKHTTSIFD DFSHYEKRQE 300
EEESVKKERQ GRGKHHHHHH                                           320
```

```
SEQ ID NO: 37            moltype = AA  length = 776
FEATURE                  Location/Qualifiers
source                   1..776
                         mol_type = protein
                         organism = synthetic construct
SEQUENCE: 37
MKIEEGKLVI WINGDKGYNG LAEVGKKFEK DTGIKVTVEH PDKLEEKFPQ VAATGDGPDI    60
IFWAHDRFGG YAQSGLLAEI TPDKAFQDKL YPFTWDAVRY NGKLIAYPIA VEALSLIYNK   120
DLLPNPPKTW EEIPALDKEL KAKGKSALMF NLQEPYFTWP LIAADGGYAF KYENGKYDIK   180
DVGVDNAGAK AGLTFLVDLI KNKHMNADTD YSIAEAAFNK GETAMTINGP WAWSNIDTSK   240
VNYGVTVLPT FKGQPSKPFV GVLSAGINAA SPNKELAKEF LENYLLTDEG LEAVNKDKPL   300
GAVALKSYEE ELVKDPRIAA TMENAQKGEI MPNIPQMSAF WYAVRTAVIN AASGRQTVDE   360
ALKDAQTNSS SNNNNNNNNN NLGIEGRISH MGSGSSGSGE NLYFQGMSSE TGPVAVDPTL   420
RRRIEPHEFE VFFDPRELRK ETCLLYEINW GGRHSIWRHT SQNTNKHVEV NFIEKFTTER   480
YFCPNTRCSI TWFLSWSPCG ECSRAITEFL SRYPHVTLFI YIARLYHHAD PRNRQGLRDL   540
ISSGVTIQIM TEQESGYCWR NFVNYSPSNE AHWPRYPHLW VRLYVLELYC IILGLPPCLN   600
ILRRKQPQLT FFTIALQSCH YQRLPPHILW ATGLKSGSET PGTSESATPE SMVTTLSGLS   660
GEQGPSGDMT TEEDSATHIK FSKRDEDGRE LAGATMELRD SSGKTISTWI SDGHVKDFYL   720
YPGKYTFVET AAPDGYEVAT PIEFTVNEDG QVTVDGEATE GDAHTGSSGS HHHHHH       776

SEQ ID NO: 38            moltype = DNA  length = 38
FEATURE                  Location/Qualifiers
misc_feature             1
                         note = PEG linker connected to 5' end
source                   1..38
                         mol_type = other DNA
                         organism = synthetic construct
SEQUENCE: 38
tataagagac agacacaggc cactcagtct atacttaa                            38

SEQ ID NO: 39            moltype = DNA  length = 28
FEATURE                  Location/Qualifiers
misc_feature             1
                         note = 5' Phosphate
misc_feature             21
                         note = RNA
misc_feature             28
                         note = PEG linker on 3' end
source                   1..28
                         mol_type = other DNA
                         organism = synthetic construct
misc_feature             1..20
                         note = DNA
misc_feature             22..28
                         note = DNA
SEQUENCE: 39
cggacacaga cagagaatat tatatata                                       28

SEQ ID NO: 40            moltype = RNA  length = 45
FEATURE                  Location/Qualifiers
misc_feature             1
                         note = 5' FAM labelled
misc_feature             30
                         note = biotinylated
source                   1..45
                         mol_type = other RNA
                         organism = synthetic construct
SEQUENCE: 40
ggcagcgtca gatgcatcat cataaggtct atattaagta tagac                    45

SEQ ID NO: 41            moltype = DNA  length = 41
FEATURE                  Location/Qualifiers
misc_feature             1
                         note = 5' FAM labelled
misc_feature             1..33
                         note = RNA
modified_base            25
                         mod_base = i
source                   1..41
                         mol_type = other DNA
                         organism = synthetic construct
misc_feature             34..41
                         note = DNA
SEQUENCE: 41
tcgtcggcag cgtcagatgc atacnaccca tagactgagt g                        41

SEQ ID NO: 42            moltype = AA  length = 359
FEATURE                  Location/Qualifiers
```

```
source                        1..359
                              mol_type = protein
                              organism = synthetic construct
SEQUENCE: 42
MSSETGPVAV DPTLRRRIEP HEFEVFFDPR ELRKETCLLY EINWGGRHSI WRHTSQNTNK      60
HVEVNFIEKF TTERYFCPNT RCSITWFLSW SPCGECSRAI TEFLSRYPHV TLFIYIARLY     120
HHADPRNRQG LRDLISSGVT IQIMTEQESG YCWRNFVNYS PSNEAHWPRY PHLWVRLYVL     180
ELYCIILGLP PCLNILRRKQ PQLTFFTIAL QSCHYQRLPP HILWATGLKS GSETPGTSES     240
ATPESMVTTL SGLSGEQGPS GDMTTEEDSA THIKFSKRDE DGRELAGATM ELRDSSGKTI     300
STWISDGHVK DFYLYPGKYT FVETAAPDGY EVATPIEFTV NEDGQVTVDG EATEGDAHT      359

SEQ ID NO: 43                 moltype = AA  length = 329
FEATURE                       Location/Qualifiers
source                        1..329
                              mol_type = protein
                              organism = synthetic construct
SEQUENCE: 43
MEASPASGPR HLMDPHIFTS NFNNGIGRHK TYLCYEVERL DNGTSVKMDQ HRGFLHNQAK      60
NLLCGFYGRH AELRFLDLVP SLQLDPAQIY RVTWFISWSP CFSWGCAGQV RAFLQENTHV    120
RLRIFAARIY DYDPLYKEAL QMLRDAGAQV SIMTYDEFKH CWDTFVDHQG CPFQPWDGLD    180
EHSQALSGRL RAILQNQGNS GSETPGTSES ATPESMVTTL SGLSGEQGPS GDMTTEEDSA    240
THIKFSKRDE DGRELAGATM ELRDSSGKTI STWISDGHVK DFYLYPGKYT FVETAAPDGY    300
EVATPIEFTV NEDGQVTVDG EATEGDAHT                                     329

SEQ ID NO: 44                 moltype = DNA  length = 41
FEATURE                       Location/Qualifiers
misc_feature                  15
                              note = RNA
source                        1..41
                              mol_type = other DNA
                              organism = synthetic construct
misc_feature                  1..14
                              note = DNA
misc_feature                  16..41
                              note = DNA
SEQUENCE: 44
agaacagaac agaatagatg ataggaagga tgaaggtgag t                          41

SEQ ID NO: 45                 moltype = DNA  length = 41
FEATURE                       Location/Qualifiers
source                        1..41
                              mol_type = other DNA
                              organism = synthetic construct
SEQUENCE: 45
agaagagaag agaacagatg ataggaagga tgaaggtgag t                          41

SEQ ID NO: 46                 moltype = RNA  length = 41
FEATURE                       Location/Qualifiers
source                        1..41
                              mol_type = other RNA
                              organism = synthetic construct
SEQUENCE: 46
agaacagaac agaatagatg ataggaagga tgaaggtgag t                          41

SEQ ID NO: 47                 moltype = RNA  length = 41
FEATURE                       Location/Qualifiers
source                        1..41
                              mol_type = other RNA
                              organism = synthetic construct
SEQUENCE: 47
agaacagaac agaacagatg ataggaagga tgaaggtgag t                          41

SEQ ID NO: 48                 moltype = DNA  length = 60
FEATURE                       Location/Qualifiers
source                        1..60
                              mol_type = other DNA
                              organism = synthetic construct
SEQUENCE: 48
gaacagaaca gaacagaaca gaacagaaca gaacagatga taggaaggat gaaggtgagt      60

SEQ ID NO: 49                 moltype = DNA  length = 60
FEATURE                       Location/Qualifiers
misc_feature                  60
                              note = SpyTag peptide attached
source                        1..60
                              mol_type = other DNA
                              organism = synthetic construct
SEQUENCE: 49
gaacagaaca gaacagaaca gaacagaaca gaacagatga taggaaggat gaaggtgagt      60
```

```
SEQ ID NO: 50          moltype = DNA  length = 60
FEATURE                Location/Qualifiers
misc_feature           38
                       note = SpyTag peptide attached
source                 1..60
                       mol_type = other DNA
                       organism = synthetic construct
SEQUENCE: 50
gaacagaaca gaacagaaca gaacagaaca gaacagatga taggaaggat gaaggtgagt    60

SEQ ID NO: 51          moltype = DNA  length = 25
FEATURE                Location/Qualifiers
misc_feature           25
                       note = 3' FAM labelled
source                 1..25
                       mol_type = other DNA
                       organism = synthetic construct
SEQUENCE: 51
ctactatcct tcctacttcc actca                                          25

SEQ ID NO: 52          moltype =   length =
SEQUENCE: 52
000

SEQ ID NO: 53          moltype =   length =
SEQUENCE: 53
000

SEQ ID NO: 54          moltype =   length =
SEQUENCE: 54
000

SEQ ID NO: 55          moltype =   length =
SEQUENCE: 55
000

SEQ ID NO: 56          moltype = DNA  length = 39
FEATURE                Location/Qualifiers
misc_feature           1
                       note = PEG linker attached to 5' end
misc_difference        22..24
misc_feature           39
                       note = blocked 3' end
source                 1..39
                       mol_type = other DNA
                       organism = synthetic construct
SEQUENCE: 56
agacgtgtgc tcttccgatc tnnnactaat tcactcagt                           39

SEQ ID NO: 57          moltype = DNA  length = 31
FEATURE                Location/Qualifiers
misc_feature           1
                       note = 5' phosphate
misc_difference        8..10
misc_feature           31
                       note = PEG linker attached to 3' end
source                 1..31
                       mol_type = other DNA
                       organism = synthetic construct
SEQUENCE: 57
actaattnnn agatcggaag agcacacgtc t                                   31

SEQ ID NO: 58          moltype = DNA  length = 19
FEATURE                Location/Qualifiers
source                 1..19
                       mol_type = other DNA
                       organism = synthetic construct
SEQUENCE: 58
ctgtctctta tacacatct                                                 19

SEQ ID NO: 59          moltype = DNA  length = 19
FEATURE                Location/Qualifiers
source                 1..19
                       mol_type = other DNA
                       organism = synthetic construct
SEQUENCE: 59
agatgtgtat aagagacag                                                 19
```

```
SEQ ID NO: 60           moltype = DNA   length = 59
FEATURE                 Location/Qualifiers
misc_feature            8
                        note = RNA
misc_difference         29..40
source                  1..59
                        mol_type = other DNA
                        organism = synthetic construct
misc_feature            1..7
                        note = DNA
misc_feature            9..59
                        note = DNA
SEQUENCE: 60
tttgtgatgc gatgaactca gagtgcttnn nnnnnnnnnn agatgtgtat aagagacag    59
```